US010213490B2

(12) United States Patent
Bromley et al.

(10) Patent No.: US 10,213,490 B2
(45) Date of Patent: Feb. 26, 2019

(54) COMPOSITIONS FOR PROVIDING AGENTS THAT DEGRADE IN WATER

(71) Applicant: VIRUN, INC., Pomona, CA (US)

(72) Inventors: Philip J. Bromley, Fullerton, CA (US); Nurruzana Rahim, Walnut, CA (US); Koon Zee Lam, Kuala Lumpur (MY)

(73) Assignee: Virun, Inc., Pomona, CA (US)

( * ) Notice: Subject to any disclaimer, the term of this patent is extended or adjusted under 35 U.S.C. 154(b) by 0 days.

(21) Appl. No.: 15/461,389

(22) Filed: Mar. 16, 2017

(65) Prior Publication Data

US 2017/0182133 A1 Jun. 29, 2017

Related U.S. Application Data

(63) Continuation-in-part of application No. PCT/US2016/052256, filed on Sep. 16, 2016.

(60) Provisional application No. 62/327,271, filed on Apr. 25, 2016, provisional application No. 62/220,957, filed on Sep. 18, 2015.

(51) Int. Cl.

| *A61K 9/127* | (2006.01) |
| *A61K 38/40* | (2006.01) |
| *A61K 9/107* | (2006.01) |
| *A61K 47/42* | (2017.01) |
| *A61K 9/16* | (2006.01) |
| *A61K 31/401* | (2006.01) |
| *A61K 35/744* | (2015.01) |
| *A61K 35/745* | (2015.01) |
| *A61K 35/747* | (2015.01) |
| *A61K 38/06* | (2006.01) |
| *A61K 38/22* | (2006.01) |
| *A61K 38/27* | (2006.01) |
| *A61K 47/10* | (2017.01) |
| *A61K 47/12* | (2006.01) |
| *A61K 47/14* | (2017.01) |
| *A61K 47/22* | (2006.01) |
| *A61K 47/24* | (2006.01) |
| *A61K 47/44* | (2017.01) |

(52) U.S. Cl.
CPC .............. *A61K 38/40* (2013.01); *A61K 9/107* (2013.01); *A61K 9/127* (2013.01); *A61K 9/1617* (2013.01); *A61K 9/1641* (2013.01); *A61K 31/401* (2013.01); *A61K 35/744* (2013.01); *A61K 35/745* (2013.01); *A61K 35/747* (2013.01); *A61K 38/063* (2013.01); *A61K 38/225* (2013.01); *A61K 38/27* (2013.01); *A61K 47/10* (2013.01); *A61K 47/12* (2013.01); *A61K 47/14* (2013.01); *A61K 47/22* (2013.01); *A61K 47/24* (2013.01); *A61K 47/42* (2013.01); *A61K 47/44* (2013.01)

(58) Field of Classification Search
None
See application file for complete search history.

(56) References Cited

U.S. PATENT DOCUMENTS

| 2,680,749 | A | 6/1954 | Cawley et al. ............... 549/410 |
| 3,538,119 | A | 11/1970 | Grant ............................ 549/410 |
| 4,665,204 | A | 5/1987 | Wirth ........................... 549/410 |
| 4,731,440 | A * | 3/1988 | Bentle .................. C07K 1/1133 |
| | | | 435/252.33 |
| 5,033,252 | A | 7/1991 | Carter ............................ 534/25 |
| 5,052,558 | A | 10/1991 | Carter ........................... 206/439 |
| 5,323,907 | A | 6/1994 | Kalvelage .................... 206/531 |
| 6,632,443 | B2 | 10/2003 | Borowy-Borowski et al. ............ |
| | | | 424/400 |
| 7,906,140 | B2 | 3/2011 | Bromley et al. ............. 424/450 |
| 8,252,323 | B2 | 8/2012 | Bromley ...................... 424/450 |
| 8,282,977 | B2 | 10/2012 | Bromley ......................... 426/72 |
| 8,414,914 | B2 | 4/2013 | Bromley et al. ............. 424/450 |
| 8,765,661 | B2 | 7/2014 | Bromley .......................... 514/1 |
| 9,320,295 | B2 | 4/2016 | Bromley ...................... 424/94.1 |
| 9,351,517 | B2 | 5/2016 | Bromley ...................... 424/94.1 |
| 9,788,564 | B2 | 10/2017 | Bromley .......................... 514/1 |
| 9,861,611 | B2 | 1/2018 | Bromley ...................... 424/456 |
| 10,016,363 | B2 | 7/2018 | Bromley ...................... 424/439 |
| 2005/0281772 | A1 | 12/2005 | Bromley et al. ........... 424/70.14 |
| 2009/0297491 | A1 | 12/2009 | Bromley ...................... 424/94.1 |
| 2009/0297665 | A1 * | 12/2009 | Bromley ............. A61K 9/1075 |
| | | | 426/72 |
| 2010/0041622 | A1 | 2/2010 | Bromley et al. ................ 514/52 |
| 2011/0117184 | A1 * | 5/2011 | Bromley ............. A61K 9/0043 |
| | | | 424/450 |
| 2011/0184194 | A1 | 7/2011 | Berl ............................ 549/410 |

(Continued)

FOREIGN PATENT DOCUMENTS

| CN | 103566376 A | 2/2014 |
| WO | WO 2014/151109 | 9/2014 |

(Continued)

OTHER PUBLICATIONS

U.S. Appl. No. 14/253,773, filed Apr. 15, 2014, 2014/0227242, Aug. 14, 2014.
U.S. Appl. No. 13/815,193, filed Feb. 8, 2013, US-2013-0309362, Nov. 21, 2013.
Letter/Written Disclosure of the Supplemental Information Disclosure Statement for the above-referenced application, filed herewith on Jul. 3, 2018, 2 pages.
Bailey et al., "Identification and Characterisation of an Iron-Responsive Candidate Probiotic," PLoS One, 6(10):e26507 (2011), 10 pages.
Daniells, S., "Virun develops shelf-stable, non-refrigerate probiotic powders, emulsions," Published on Nov. 16, 2016, Retrieved from: <URL:https://www.nutraingredients-usa.com/Article/2016/11/16/Virun-develops-self-stable-non-refrigerate-probiotic-powders-emulsions [retrieved on Nov. 20, 2017], 1 page.

(Continued)

*Primary Examiner* — Brian Gulledge
(74) *Attorney, Agent, or Firm* — Dentons US LLP; Stephanie Seidman

(57) ABSTRACT

Compositions and methods for mucosal delivery of agents are provided. The compositions are intended for administration to mucosal surface, such as oral, gastrointestinal and nasal mucosa. The compositions provided contain one or more mucoadhesive proteins and an agent to be delivered. Methods for delivery of agents using the compositions provided herein are also provided.

21 Claims, No Drawings

(56) References Cited

U.S. PATENT DOCUMENTS

| | | |
|---|---|---|
| 2011/0236364 A1 | 9/2011 | Bromley .................. 424/94.1 |
| 2012/0308644 A1 | 12/2012 | Bromley et al. ............. 424/450 |
| 2013/0017295 A1 | 1/2013 | Bromley .................. 426/66 |
| 2014/0242055 A1 | 8/2014 | Bromley .................. 424/94.1 |
| 2014/0271593 A1 | 9/2014 | Bromley .................. 424/94.1 |
| 2015/0110924 A1 | 4/2015 | Bromley .................. 426/72 |
| 2016/0081927 A1 | 3/2016 | Bromley .................. 424/439 |
| 2016/0081975 A1 | 3/2016 | Bromley .................. 424/464 |
| 2016/0081976 A1 | 3/2016 | Bromley .................. 424/456 |
| 2016/0193146 A1 | 7/2016 | Bromley .................. 424/94.1 |
| 2016/0227832 A1 | 8/2016 | Bromley .................. 424/94.1 |
| 2017/0273326 A1 | 9/2017 | Tsubota et al. ............. 424/93.4 |
| 2018/0042865 A1 | 2/2018 | Bromley .................. 426/72 |
| 2018/0098962 A1 | 4/2018 | Bromley .................. 424/456 |

FOREIGN PATENT DOCUMENTS

| | | |
|---|---|---|
| WO | WO 2016/032000 | 3/2016 |
| WO | WO 2017/049162 | 3/2017 |

OTHER PUBLICATIONS

Database GNPD [online] Mintel; Annonymous: "Innerbio-Formula," XP002776260, Retrieved from: <URL:www.gnpd.com, Database Accession No. 281180, 2 pages.

Response, filed Jul. 18, 2017, to International Search Report and Written Opinion, dated Mar. 8, 2017, in connection with corresponding International Patent Application No. PCT/US2016/052256, 33 pages.

Written Opinion, dated Aug. 30, 2017, in connection with corresponding International Patent Application No. PCT/US2016/052256, 6 pages.

Response, filed Oct. 27, 2017, to Written Opinion, dated Aug. 30, 2017, in connection with corresponding International Patent Application No. PCT/US2016/052256, 40 pages.

International Search Report and Written Opinion, dated Dec. 20, 2017, in connection with International Patent Application No. PCT/US2017/051923, 13 pages.

Office Action, dated Apr. 16, 2018, in connection with corresponding Great Britain Patent Application No. GB1804800.9, 4 pages.

Response, filed Jun. 14, 2018, to Examination Report, dated Apr. 16, 2018, in connection with corresponding United Kingdom Patent Application No. 1804800.9 [D2=CN 103566376], 9 pages.

Letter/Written Disclosure of the Information Disclosure Statement for the above-referenced application, dated Jun. 16, 2017, 2 pages.

Almeida et al., "Nasal delivery of vaccines," Journal of Drug Targeting 3:456-467 (1996).

Ansel, H., "Introduction to Pharmaceutical Dosage Forms," Fourth Edition, Philadelphia: Lea & Febiger, p. 126 (1985).

Bevnet website "Virun Releases Episode 2 of Probiotic and Omega Supplement Video Series," published on Feb. 13, 2017 [online] retrieved from <URL:bevnet.com/news/2017/virun-releases-episode-2-probiotic-omega-supplement-video-series [retrieved on Feb. 13, 2017], 2 pages.

Bromley, P., "Inside Virun: Manufacturing the next generation of supplements, foods and beverages," presented at the 2016 Beverage Innovation: Online Summit, Feb. 18, 2016, Retrieved from: <URL:vts.inxpo.com/scripts/Server.nxp?LASCmd=AI:1;S:17;F:QP!14100&EventKey=178592&EventAttendeeKey=14661401&RandomValue=1456260156563 [retrieved on Feb. 23, 2016], 70 pages.

Christiansen et al., "Investigating the stability of the nonionic surfactants tocopheryl polyethylene glycol succinate and sucrose laurate by HPLC-MS, DAD, and CAD," J. Pharm. Sci. 100(5):1773-1782 (2011).

Collnot et al., "Influence of vitamin E TPGS poly(ethylene glycol) chain length on apical efflux transporters in Caco-2 cell monolayers," J. Controlled Release 111:35-40 (2006).

Degnan, F.H., "The US Food and Drug Administration and Probiotics: Regulatory Categorization," Clin Infect Dis. 46 (Supplement 2):S133-S136 (2008).

Deschemin et al.,"The microbiota shifts the iron sensing of intestinal cells," FASEB J. 30(1):252-61 (2016).

English translation of abstract of Chinese Patent No. CN103566376 (A), published Feb. 12, 2014, accessed from Espacenet on May 31, 2017, 1 page.

Ferdousi et al., "Evaluation of Probiotic Survivability in Yogurt Exposed to Cold Chain Interruption," Iran. J. Pharm. Res. 12(Suppl):139-144 (2013).

Good, R., "Surface free energy of solids and liquids: Thermodynamics, molecular forces, and structure," Journal of Colloid and Interface Science 59(3):398-419 (1977).

Griffin, W., "Classification of surface-active agents by "HLB"," J. Soc. Cos. Chem. 1:311-326 (1949), 17 pages.

Iravani et al., "Technology and potential applications of probiotic encapsulation in fermented milk products," J. Food Sci. Technol. 52(8):4679-4696 (2015).

Kong et al., "Direct quantification of mono- and di-D-$\alpha$-tocopherol polyethylene glycol 1000 succinate by high performance liquid chromatography,." J. Chromatography A 1218:8664-8671 (2011).

Mitropoulou et al., "Immobilization Technologies in Probiotic Food Production," J. Nutr. Metab. 2013:716861 (2013), 15 pages.

Muthu et al., "Theranostic vitamin E TPGS micelles of transferrin conjugation for targeted co-delivery of docetaxel and ultra bright gold nanoclusters," Biomaterials 39:234-248 (2015).

NUTRAingredients-usa "Virun develops shelf-stable, non-refrigerate probiotic powders, emulsions," published on Nov. 16, 2016 [online], retrieved from: <URL:nutraingredients-usa.com/Suppliers2/Virun-develops-shelf-stable-non-refrigerate-probiotic-powders-emulsions [retrieved on Feb. 13, 2017], 2 pages.

Nutritional Outlook "Virun Unveils New Shelf-Stable Probiotic Powders, Emulsions," published on Nov. 17, 2016 [online], retrieved from: <URL:nutritionaloutlook.com/digestive-health/virun-unveils-new-shelf-stable-probiotic-powders-emulsions [retrieved on Feb. 13, 2017], 2 pages.

Press Release: "DSM: 'Consumers are searching for new ways to add omega-3s into their diet'," Published on Jul. 27, 2015 [online], retrieved from: <URL:nutraingredients-usa.com/content/view/print/1145391 [retrieved on Nov. 4, 2015], 2 pages.

Press Release: "We All Want to Live in a Yellow Submarine at Virun's SupplySide West Booth," Published on Sep. 15, 2016 [online], retrieved from <URL: pr.com/press-release/687560 [retrieved on Nov. 22, 2016], 3 pages.

Press Release: "Virun® Launches a Line of Shelf-Stable Probiotic Multi-Serving Powders and Emulsions," Published on Nov. 15, 2016 [online], retrieved from <URL: pr.com/press-release/695282 [retrieved on Nov. 22, 2016], 3 pages.

Press Release: "Virun® Releases Static Episode 2 While Under the Influence of Sulfur Hexaflouride, and New Probiotic Technology Makes Wholefoods Take Notice," Published on Feb. 14, 2017 [online], retrieved from <URL: pr.com/press-release/705384 [retrieved on Mar. 15, 2017], 3 pages.

Saarela et al., "Improving the storage stability of Bifidobacterium breve in low pH fruit juice," Int J Food Microbiol. 149(1):106-10 (2011).

Scientific Panel of the European Food Safety Authority, "Opinion of the Scientific Panel on Food Additives, Flavourings, Processing Aids and Materials in Contact with Food on a request from the Commission related to D-alpha-tocopheryl polyethylene glycol 1000 succinate (TPGS) in use for food for particular nutritional purposes," EFSA J. 490:1-20 (2007), 20 pages.

Shah et al., "Improving the Stability of Probiotic Bacteria in Model Fruit Juices Using Vitamins and Antioxidants," J. Food Sci. 75(5):M278-82 (2010).

Sherman et al., "Neonatal small bowel epithelia: enhancing antibacterial defense with lactoferrin and Lactobacillus GG," Biometals 17(3):285-289 (2004).

Smart et al., "An in-vitro investigation of mucosa-adhesive materials for use in controlled drug delivery," J. Pharm. Pharmacol. 36:295-299 (1984).

Smart et al., "In vitro techiniques for measuring mucoadhesion," J. Pharm. Pharmacol. 34:70P (1982).

(56) References Cited

OTHER PUBLICATIONS

Sreeja and Prajapati, "Probiotic Formulations: Application and Status as Pharmaceuticals—A Review," Probiotics and Antimicro. Prot. 5(2):81-91 (2013).
Tabor et al., "Surface forces and surface interactions," Journal of Colloid and Interface Science 58(1):2-13 (1977).
Tian et al., "Influence of bovine lactoferrin on selected probiotic bacteria and intestinal pathogens," Biometals 23(3):593-596 (2010).
Ex Parte Reexamination Certificate, issued Apr. 14, 2017, in connection with U.S. Reexamination No. 90/012,700, 2 pages.
Vighi et al., "Allergy and the gastrointestinal system," 153(Suppl 1): 3-6 (2008).
Virun Esolv technology Webpage, found at: http://www.virun.com/omega2.htm [accessed Jun. 2, 2014], 1 page.
Virun Esolv—functional beverages cognitive ingredients, Product Pamphlet, Published on Feb. 10, 2016 [online], retrieved from: <URL:vts.inxpo.com/scripts/Server.nxp?LASCmd= AI:1;S:41008;F:LBSATTACH!V&AttachmentKey=1309416 [retrieved on Feb. 23, 2016], 4 pages.
Virun Facebook Page [online], retrieved from: <URL: facebook.com/Virun-168007462662/?fref=ts [retrieved on May 31, 2016], 6 pages.
Virun Facebook Page [online], retrieved from: <URL: facebook.com/viruninnovations/ [retrieved on Dec. 14, 2016], 25 pages.
Virun Facebook Page [online], retrieved from: <URL: facebook.com/viruninnovations/ [retrieved on Mar. 15, 2017], 14 pages.
Virun News, "Probiferrin Debuts at Ingredient Marketplace, New Website for Virun, and Static 3 Underway," email newsletter received on May 2, 2017, 5 pages.
Virun Static blog, "Three Separations of Product Brands and Distribution from a Developer," Published on Nov. 8, 2016 [online] Retreived from <URL: virun.com/blog [retrieved on Nov. 22, 2016], 2 pages.
Virun Static blog, "Not all Probiotics are Created Equal—How Industry is Fooling the Consumer," Published on Mar. 22, 2017 [online], retrieved from <URL: virun.com/blog [retrieved on Mar. 24, 2017], 5 pages.
Virun Static Episode 1 Transcript, "Uncovering 'The Good, the Bad & the Ugly' of Nutritional Products," Published Sep. 22, 2016, retrieved from <URL: youtube.com/watch?v=3zEhTdurefM, 6 pages.
Virun Static Episode 2 Transcript, "Under the Influence," Published Feb. 7, 2017, retrieved from <URL: youtube.com/watch?v=VvrhuZNUD-8, 6 pages.
Brief of Appellant, filed Feb. 1, 2016, in connection with U.S. Reexamination No. 90/012,700, 78 pages.
Brief of Appellee, filed Apr. 22, 2016, in connection with U.S. Reexamination No. 90/012,700, 52 pages.
Appellant's Reply Brief, filed Jun. 8, 2016, in connection with U.S. Reexamination No. 90/012,700, 42 pages.
Judgment, issued Nov. 10, 2016, in connection with U.S. Reexamination No. 90/012,700, U.S. Court of Appeals for the Federal Circuit, Appeal No. 16-1280, in re: Virun, Inc., 5 pages.
Notice of Intent to Issue Ex Parte Reexamination Certificate, issued Mar. 10, 2017, in connection with U.S. Reexamination No. 90/012,700, 5 pages.
International Search Report and Written Opinion, dated Mar. 8, 2017, in connection with International Patent Application No. PCT/US2016/052256, 19 pages.
Letter/Written Disclosure of the Supplemental Information Disclosure Statement for the above-referenced application, filed herewith on Aug. 22, 2018, 2 pages.
International Preliminary Report on Patentability, dated Jan. 19, 2018, in connection with corresponding International Patent Application No. PCT/US2016/052256, 8 pages.
Letter/Written Disclosure of the Supplemental Information Disclosure Statement for the above-referenced application, filed herewith on Sep. 14, 2018, 2 pages.
Examination Report, dated Aug. 17, 2018, in connection with Great Britain Patent Application No. 1804800.9, 3 pages.

* cited by examiner

COMPOSITIONS FOR PROVIDING AGENTS THAT DEGRADE IN WATER

RELATED APPLICATIONS

This application is a continuation-in-part of PCT/US2016/052256, filed Sep. 16, 2016, entitled "COMPOSITIONS FOR PROVIDING AGENTS THAT DEGRADE IN WATER," to Philip J. Bromley, Nurruzana Rahim and Koon Zee Lam, which claims the benefit of priority to U.S. provisional application Ser. No. 62/327,271, filed Apr. 25, 2016, to Philip J. Bromley, Nurruzana Rahim, and Koon Zee Lam, entitled "COMPOSITIONS FOR PROVIDING AGENTS THAT DEGRADE IN WATER," and to U.S. provisional application Ser. No. 62/220,957, filed Sep. 18, 2015, to Philip J. Bromley, Nurruzana Rahim, and Koon Zee Lam, entitled "COMPOSITIONS FOR PROVIDING AGENTS THAT DEGRADE IN WATER." The subject matter of each of these applications is incorporated by reference in its entirety.

FIELD OF THE INVENTION

Provided are pharmaceutical compositions for delivery of biologically active agents, such as sulfur-containing proteins and probiotics, that are inactivated in the presence of water. The compositions can be formulated as emulsions for mucosal delivery. Also provided are methods for preparing powders of compositions containing temperature-sensitive proteins, such as transferrins, including lactoferrin.

BACKGROUND

Numerous pharmaceutical substances are available for administration to animals, including humans, for a variety of purposes. These substances include, for example, therapeutic agents, such as drugs; dietary supplements, such as vitamins; prophylactic agents, such as antigens for use in vaccines; and diagnostic agents, such as labeled imaging agents. Administration of these substances can be via a number of routes including intramuscular, subcutaneous and oral administration. Intramuscular and subcutaneous administration of the substance suffer from disadvantages. For example, specialized skills are required to administer the pharmaceutical; large scale administration can be difficult to perform; it is expensive; and a number of side reactions can occur to the substance administered. There are biologically active agents, for example certain dietary supplements, drugs, hormones and immunogens, whose efficacy almost totally is lost upon oral administration. Included among those agents that cannot be effectively orally administered are polypeptide agents. Oral delivery of certain protein and polypeptide drugs and other biological agents is complicated by the presence of proteolytic digestive enzymes in the stomach and intestines. Unprotected proteins, which are administered orally, are largely degraded by such enzymes before they are passed through the enteric wall and enter blood circulation. Many such agents cannot be formulated in water; there are numerous agents that, upon exposure to water, are not stable. Thus, there continues to be a need for the development of compositions and methods for delivery of such substances to animals, including humans.

SUMMARY

Among the objects herein is provision of compositions and methods for delivery of polypeptides and other biological agents that cannot be delivered orally and that are sensitive to exposure to water. U.S. Pat. Nos. 8,252,323, 7,906,140 and 8,414,914 describe mucosal adhesive penetrating technology (MAPT) for mucosal delivery of agents, such as therapeutic proteins. The prior MAPT formulations, however, generally include water, and, thus, can result in problems with stability of formulations that contain agents that are susceptible to degradation in water.

Provided herein are compositions and methods for formulation of the compositions for mucosal delivery of agents susceptible to degradation in the presence of water. These agents include, for example, sulfur-containing proteins, such as glutathione, probiotics, peptides, such as growth hormone releasing hexapeptide (GHRP-6) and calcitonin, which degrade in the presence of water. The agents also include probiotics. The compositions and methods for administering such substances to animals, including humans, employ a carrier that facilitates entry of the substance via the mucosa in a non-specific manner. The MAPT compositions provided herein include those that contain no water, but are free-flowing liquids that contain water-sensitive agents, such as glutathione, probiotics, peptides, such as growth hormone releasing hexapeptide (GHRP-6), calcitonin and probiotics, that previously were not provided as a liquid in view of their water-sensitivity.

While MAPT generally includes water in the formulations, water is not ideal for formulations that contain agents that are susceptible to degradation in water. Provided herein is a modification of the MAPT technology providing compositions that are substantially free of water or are free of water, whereby the biologically active agent, such as a sulfur containing protein or probiotic, is stable. Included among the compositions are those that contain glutathione and/or probiotics. The resulting compositions are stable compared to prior art compositions, and, those that contain sulfur-containing proteins, do not have a sulfur taste or odor. In compositions provided herein, non-aqueous polar protic solvents are employed in the compositions in place of water. Such non-aqueous polar solvents include, for example, glycerin, and other such biocompatible polar alcohol solvents, including propylene glycol and diethylene glycol. The resulting compositions are emulsions that are formed from a polar phase that contains the non-aqueous polar solvent, such as glycerin, as the solvent, the mucoadhesive protein(s), such as lactoferrin, and other components soluble in the polar protic solvents, and an oil phase that contains oils, oil soluble agents, surfactants, such PEG-derivative of vitamin E, particularly d-alpha tocopheryl polyethylene glycol succinate (TPGS), sucrose fatty acid esters, and polysorbates, such as polysorbate 80, and an optional co-solvent, which can be glycerin. The phases are mixed to form the resulting MAPT compositions that do not contain water.

Also provided are methods for spray-drying compositions and the resulting powders that contain temperature-sensitive mucoadhesive proteins, such as the transferrins, such as lactoferrin, and also methods for spray drying MAPT compositions that include water and water-sensitive agents. The resulting powders are soluble in aqueous media, such as water and other beverages for consumption. These powders also permit formulation of the water-sensitive agents in the presence of water. The compositions are formulated in water, and then spray-dried after formulation before the agents degrade. They then can be reconstituted in water. The compositions for spray-drying include lactoferrin and a PEG-derivative of vitamin E, such as d-alpha tocopheryl polyethylene glycol succinate (TPGS), which encapsulates or associates with the agents and lactoferrin to protect them from degradation when heated for spray drying. The lactoferrin provides for mucosal delivery of the agents when the powders are ingested or diluted into water.

Compositions herein, thus, are similar to those described in U.S. Pat. Nos. 8,252,323, 7,906,140 and 8,414,914, but are modified to advantageously permit formulation of water-sensitive agents or agents degraded in water, such as sulfur-containing proteins and probiotics. The compositions do not contain any water, and thus, can be used for provision of agents that are not stable in water, such as glutathione. Glycerin or other such polar protic solvent is employed in place of the water in the polar (water) phase of the MAPT. While the MAPT can include glycerin, it is employed as a co-solvent, which is included in the oil phase during formulation, not in the polar phase during formation or preparation of the resulting emulsion. In the instant compositions, glycerin, in addition to its use an optional co-solvent in the oil phase, is employed as the solvent in the polar phase. No water is included in either phase. This permits formulation of agents, such as glutathione, growth hormone releasing hexapeptide (GHRP-6), calcitonin, biologics, such as probiotics and other agents, that degrade in or are sensitive to water. For example, in general the use of L-glutathione in food and beverage products has been self-limiting because of its sour taste and sulfur odor. In contrast, in the compositions and powders provided herein, the glutathione is 100% stable, even when added diluted into a beverage, such as a flavored water at pH 3.2. Thus, the compositions and powders provided herein solve a problem in the art.

The compositions provided herein have a mucoadhesive property whereby the composition, when administered either orally or nasally, adheres to and/or anchors to a subject's mucous membranes in the mouth, nose and/or gastrointestinal tract, for a period of time sufficient to quantitatively deliver the agent, such as glutathione, to be delivered to the subject. The compositions contain a mucoadhesive substance that imparts the composition a property of adhering or anchoring to a mucosal membrane thereby effecting absorption of the agent through the mucosal membrane. The mucoadhesive protein is present in an amount sufficient to confer mucoadhesive property to the composition. Such mucosal absorption allows entry of the agent being delivered into the systemic circulation without first passing through the liver or digestive tract, and thus alleviates the loss of activity upon passage through the liver.

The mucoadhesive substances for use herein include, but are not limited to natural or synthetic proteins, polypeptides or fragments thereof that have the property of adhering or penetrating into a mucus membrane for a period of time sufficient to achieve quantitative delivery of an agent to be delivered. The compositions are designed for mucosal delivery, particularly orally by contacting mucosal surfaces of the mouth, throat and digestive system, of a therapeutically-effective amount of a sulfur-containing agent to the subject. The mucoadhesive protein is generally dissolved in the polar phase. For compositions herein, the polar phase is not water. In certain embodiments the mucoadhesive protein can be dissolved in the oil phase. The mucoadhesive protein is typically anchored to polar head groups of the delivery vehicles in the emulsion.

In certain embodiments, the compositions provided herein are formulated to contact the mucosal membrane from about 5-24 hours or even longer, in some embodiments about 5, 10, 12, 14, 16, 18, 20, 22 or up to 24 hours. In some embodiments, the compositions provided herein are formulated to contact the mucosal membrane from about 1 minute up to about 180, 120, 100, 60, 40, 30, 20, 10, 5, 4, 3, or 2 minutes. In certain embodiments, the compositions provided herein are formulated to adhere or penetrate into the mucosal membrane from about 5-24 hours or even longer, in some embodiments for about 5, 10, 12, 14, 16, 18, 20, 22 or up to 24 hours. In some embodiments, the compositions provided herein are formulated to adhere or penetrate into the mucosal membrane from about 1 minute up to about 180, 120, 100, 60, 40, 30, 20, 10, 5, 4, 3, or 2 minutes. In other embodiments, the compositions provided herein are formulated to adhere and penetrate into the mucosal membrane from about 5-24 hours or even longer, in some embodiments, for about 5, 10, 12, 14, 16, 18, 20, 22 or up to 24 hours. In some embodiments, the compositions provided herein are formulated to adhere and penetrate into the mucosal membrane from about 1 minute up to about 180, 120, 100, 60, 40, 30, 20, 10, 5, 4, 3, or 2 minutes. In certain embodiments, the compositions provided herein are formulated to adhere to the mucosal membrane from about 5-24 hours or even longer, in some embodiments for about 5, 10, 12, 14, 16, 18, 20, 22 or up to 24 hours. In some embodiments, the compositions provided herein are formulated to adhere to the mucosal membrane from about 1 minute up to about 180, 120, 100, 60, 40, 30, 20, 10, 5, 4, 3, or 2 minutes. In certain embodiments, the compositions provided herein are formulated to penetrate into the mucosal membrane from about 5-24 hours or even longer, in some embodiments for about 5, 10, 12, 14, 16, 18, 20, 22 or up to 24 hours. In some embodiments, the compositions are formulated to penetrate into the mucosal membrane from about 1 minute up to about 180, 120, 100, 60, 40, 30, 20, 10, 5, 4, 3, or 2 minutes.

Compositions provided herein can have a wide range of viscosities, typically in a range that assists retention of the composition on a mucosal surface. Generally, the viscosity ranges from an oil like viscosity, honey like viscosity, ketchup like (50,000 to 100,000 cps) viscosity, chocolate syrup like viscosity to peanut butter (about 250,000 cps) like or butter like viscosity, such as 50,000 cps to 300,000 cps, 100,000 cps to 350,000 cps, or 50,000 cps to 500,000 cps. The viscosity of the compositions can be measured by methods known to those of skill in the art, including measurement by using a viscometer such as Brookfield LVDV-I+ viscometer and T spindles with a heliopath adapter. The viscosity of the compositions provided can range, for example, from at least 10 cps, 100 cps, 1000 cps, 10,000 cps, 100,000 cps, or 200,000 cps up to more than 500,000 cps, such as to 100,000 cps, 150,000 cps, 200,000 cps, or 250,000 cps at 72° F. (room temperature), such as 10,000 cps to 50,000 cps or 100,000 cps, 100,000 cps to 250,000 cps; or 1000 cps to 50,000 cps.

The compositions provided herein are formulated to remain stable over a relatively long period of time so that the formulated agents remain active, such as at least 10%, 20%, 30%, 40%, 50%, 60%, 70%, 80%, 85%, 90%, or 95%, generally more than 85%, or more activity is retained after formulation for more than a week, typically a month or more. For example, the compositions provided herein are stored at room temperature, and remain stable for more than 1 day, 1 week, 1 month and in certain embodiments up to more than 1 year. In certain embodiments, the compositions provided herein are delivered to the oral mucosa or nasal mucosa. In certain embodiments, the compositions are delivered to intestinal mucosa or oral and intestinal mucosa.

Also provided herein are methods of using the compositions. In certain embodiments, the methods provided herein are used for delivery of one or more agents to be delivered including, but not limited to biologically active agents such as water-sensitive minerals, vitamins, synthetic or natural compounds, pharmaceutical drugs, nutritional supplements, herbs and hormones and, which when introduced into the body cause a desired biological response, such as altering body function at the cellular, tissue or organ level and/or altering cosmetic appearance. In particular, the compositions are for formulation of water-sensitive agents, such as glutathione, calcitonin, growth hormone releasing hexapeptide (GHRP-6), and various probiotics and other such agents. The compositions can be ingested directly or diluted into a beverage, such as water. As described herein, the powders are formulated so that they can be diluted into water, but the water-sensitive agent is protected from degradation by virtue of the formulation with the PEG-derivative of vitamin E, such as TPGS.

In certain embodiments, the methods are used to deliver a biological agent, wherein the agent is a drug or other pharmaceutical ingredient that is water sensitive, and that has significant loss of activity in the lumen of the gastrointestinal tract or in the tissues of the gastrointestinal tract during absorption process or upon passage through the liver after absorption in the intestinal tract. The compositions and methods provided herein are useful for delivery of sulfur containing therapeutics used in treatment of various disorders and as dietary supplements.

Methods of making the compositions also are provided. The compositions provided herein are prepared by mixing an oil phase with a polar phase at a mixing speed that does not degrade and disintegrate any of the active ingredients of the composition. The mixing speed can range from about 100 RPM up to about 60,000 RPM. The temperature, pressure, and pH conditions during the mixing step are maintained so that all the components in the oil and polar protic solvent, other than water, phase are dissolved and the active ingredients are not degraded in any way. A suitable temperature during the mixing step can be determined empirically for a particular combination of ingredients in the composition. Typically, the temperature is maintained at about 100-120° F., in some embodiments at about 115° F. The pressure during the mixing is maintained at about 25 PSI (pounds per square inch). The pH during the mixing step is a function of the particular mucoadhesive protein and the agent to be delivered in the composition. Typically the pH is basic or neutral.

The compositions can be prepared by mixing the polar phase with an oil phase to form a polar protic solvent (other than water)-in-oil emulsion. The agent to be delivered can be dissolved in the oil phase or in the polar protic solvent, other than water, phase. Typically, a mucoadhesive protein is present in the polar protic solvent, other than water, phase in an amount sufficient to confer mucoadhesive property to the composition. In certain embodiments, the compositions adhere or anchor to the mucosal surface for an amount of time sufficient to achieve quantitative delivery of the agent to be delivered. The compositions provided herein can also include one or more surface active agent, and one or more additives, such as a polymer, a cosolvent, an antioxidant, an antiseptic, a buffering agent, a chelating agent, a colorant, a flavorant, an odorant, an osmotic modifier, a preservative, a solubilizer, a tonicifier, a trace element, a viscomodulator, or a mixture thereof. Such additives are known to those of skill in the art and are described herein.

Articles of manufacture, containing packaging material for a composition for mucosal delivery and administration, a composition for mucosal delivery of biologically active agents and a label that indicates that the composition is for achieving a desired biological response, such as altering body function or altering cosmetic appearance. In certain embodiments, the articles of manufacture, contain a packaging material, a composition for mucosal delivery of biologically active agents and a label that indicates that the composition is useful for treatment, prevention or amelioration of one or more symptoms of diseases or disorders contemplated herein.

Also provided are methods for spray drying compositions and the resulting compositions, which contain temperature sensitive ingredients, such as the mucoadhesive proteins, such as lactoferrin, as well as other products, such as probiotics. The compositions are formulated with a PEG-derivative of vitamin E, such as TPGS, particularly a high dimer TPGS, and then spray-dried. This combination of ingredients, PEG-derivative of vitamin E, such as the TPGS, with the mucoadhesive protein renders the mucoadhesive protein resistant or less sensitive to heat so that it can be spray dried without denaturing. The resulting powders can be provided as capsules, tablets or other such forms, and/or can be reconstituted in water.

DETAILED DESCRIPTION

Outline

A. Definitions
B. Compositions
1. Mucosal delivery
2. MAPT Compositions
  a. Mucoadhesive proteins
  b. Oils
  c. Surface Active Agents
  d. PEG-derivatives of vitamin E
    1) Vitamin E
    2) Polyalkylene glycol derivatives of vitamin E
      a) Tocopherols and tocotrienols
      b) Linkers
      c) PEG moieties
    3) Synthesis
  e. Agents for delivery
  f. Polymers
  g. Cosolvent
  h. Other additives
  i. Exemplary Compositions
  j. Probiotic compositions
3. Compositions for Spray-drying and Spray Dried Powders
C. Methods of Manufacturing The MAPT Compositions
1. Equipment used in exemplary procedures provided herein include:
  a. Tanks
  b. Mixers
  c. Heating apparatus
2. Exemplary procedures for preparing the compositions
  a. Procedure A
    1) Oil phase
    2) Polar protic solvent phase
    3) Formation of Emulsion
  b. Procedure B
    1) Oil phase
    2) Polar protic solvent phase
    3) Formation of Emulsion
  c. Procedure C
    1) Oil phase
    2) Polar protic solvent phase
    3) Formation of Emulsion D. Formulations
E. Methods of use of the compositions
F. Articles of manufacture

EXAMPLES

A. Definitions

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, mucosa or mucus membrane refers to epithelial tissue that lines the internal cavities of the body, such as oral cavity, the respiratory tract, the gastrointestinal tract, the lungs, and the genitalia. The mucous membrane or mucosa protects the body from foreign matter and pathogens and is permeable to a certain extent. Agents delivered through the mucosa enter circulation in hours or for as long as about 24 hours after administration (i.e. about 4-24 hours for insulin). Entry of the agent to be delivered is a function of the drug and the mucoadhesive protein selected. The compositions provided herein exploit the limited permeability of the mucosa and generally are formulated for delivery through the oral and nasal mucosa, although they can be formulated for delivery through any mucosal surface, including the mouth, nasal passages, gastrointestinal tract, lungs and the mucosal layer of other tissues and organs.

As used herein, mucosal delivery refers to delivery of an agent in which the agent is introduced to the body across a mucous membrane which allows for the avoidance of the gastrointestinal tract and first pass liver metabolism and consequently allows the agent to directly enter into circulation. This can include passage through the gastrointestinal tract as by oral ingestion, but refers to delivery through the mucosa of such locus.

As used herein, "contact to a mucosal surface" or "contact with a mucosal surface" refers to contact of the composition into the mucosal surface for an amount of time sufficient to achieve quantitative delivery of the composition. Contact of the composition can result in adhesion and/or penetration of the composition into the mucosal surface. The compositions provided herein can contact the mucosal surface from 30 seconds up to about 24 hours. In certain embodiments, the composition contacts the mucosal surface for at least about 5, 10, 12, 14, 16, 18, 20, 22 or up to 24 hours. In some embodiments, the compositions provided herein contact the mucosal membrane from about 1 minute up to about 180, 120, 100, 60, 40, 30, 20, 10, 5, 4, 3, or 2 minutes.

As used herein, mucoadhesive property refers to a property whereby a natural or synthetic substance, such as a protein, when applied to a mucosal epithelium adheres to or penetrates a subject's mucous membrane for a period of time sufficient to quantitatively deliver a composition provided herein to the subject. The composition can anchor in and/or penetrate into a mucosal surface. Adhesion of mucoadhesives to a mucous membrane occurs generally, although not necessarily or exclusively, via secondary chemical bonds, such as hydrogen bonding and Van der Waal forces (Tabor et al., 1977 J. Colloid Interface Sci. 58:213 and Good, 1977 J. Colloid Interface Sci. 59:398-419). Parameters, such as mechanical binding to mucous membrane per se or the degree of biological effect of an agent delivered can be used as a measurement parameter to detect and quantitate mucoadhesion.

As used herein, mucoadhesive compositions are viscous aqueous solutions. Their mucoadhesive (or penetrative) properties can be assessed by comparison to a control composition that does not contain the mucoadhesive protein(s) added to the mucoadhesive composition. At similar viscosities, the emulsion prepared with a mucoadhesive protein or protein binds to a mucosal surface more strongly (i.e. more is bound or penetrates or is delivered) compared to a control emulsion without the mucoadhesive protein or protein(s). Such increase in delivery or binding or penetration is at least about 10%, 20%, 30%, 40%, 50%, 60%, 70%, 80%, 90% or 100% greater mucosal binding than a control emulsion.

As used herein, mucoadhesive proteins refer to any natural or synthetic proteins, polypeptides or fragments thereof that possess the mucoadhesive property. Non-limiting examples of mucoadhesive proteins include mucin proteins and transferrins. In certain embodiments, the protein for use in the compositions and methods provided herein is lactoferrin. In certain embodiments, the mucoadhesive protein present in a composition provided herein is in an amount sufficient to confer a mucoadhesive property to the composition.

As used herein, a "solvent" is an ingredient that can be used to dissolve another ingredient. Solvents include polar and non-polar solvents. Non-polar solvents include oils and other non-polar ingredients that dissolve non-polar compounds. Typically, the non-polar solvent is an oil that is included in the concentrates or liquid dilution compositions provided herein in addition to the non-polar compound. The non-polar solvent typically is not the non-polar compound itself, i.e., is distinct from the non-polar compound. More than one non-polar solvent can be used. Certain compounds, for example, flaxseed oil and safflower oil, can be non-polar solvents and non-polar active ingredients. Typically, the non-polar solvent contains one or more oils, typically oils other than the non-polar active ingredient or oil(s) not contained in the active ingredient. Exemplary non-polar solvents include, but are not limited to, oils (in addition to the non-polar active ingredient), for example, vitamin E oil, flaxseed oil, CLA, borage oil, rice bran oil, D-limonene, canola oil, corn oil, MCT (medium chain triglycerides) oil and oat oil. Other oils also can be used.

As used herein, MCT oil is comprised of primarily caprylic and capric fatty acids, and is a light-yellow, odorless, translucent liquid at room temperature. MCT oil occurs naturally in coconut oil and other foods.

As used herein, "polar solvent" refers to a solvent that is readily miscible with water and other polar solvents. Polar solvents are well-known and can be assessed by measuring any parameter known to those of skill in the art, including dielectric constant, polarity index and dipole moment (see, e.g., Przybitek (1980) "High Purity Solvent Guide," Burdick and Jackson Laboratories, Inc.). For example, polar solvents generally have high dielectric constants, such as greater than or about 15, generally have high polarity indices, typically greater than or about 3, and generally large dipole moments, for example, greater than or about 1.4 Debye. Polar solvents include polar protic solvents and polar aprotic solvents.

As used herein, a "polar protic solvent" is a polar protic solvent containing a hydrogen atom attached to an electronegative atom, such that the hydrogen has a proton-like character and/or the bond between the hydrogen and electronegative atom is polarized. Exemplary polar protic solvents include, but are not limited to, water, alcohols, including monohydric, dihydric and trihydric alcohols, including, but not limited to, methanol, ethanol, glycerin and propylene glycol.

As used herein, glycerin is interchangeable with glycerine and glycerol (IUPAC name propane-1,2,3-triol) and has the formula: $HO-CH_2CH(OH)CH_2.OH$.

As used herein, "biologically compatible substance" refers to a substance that, when administered to a subject, such as a human, does not produce undesired or toxic effects.

As used herein, "an agent" is any substance that can be delivered via compositions provided herein to a mucosal surface of a subject. Generally for purposes herein, the agent is one that is susceptible to degradation in the presence of water or is unstable in the presence of water or moisture.

As used herein, "a biologically active agent," "a biological agent," or "an agent" is any substance which when introduced into the body causes a desired biological response, such as altering body function at the cellular, tissue or organ level and/or altering cosmetic appearance. Such substance can be any synthetic or natural element or compound, protein, cell, or tissue including a pharmaceutical, drug, therapeutic, nutritional supplement, herb, hormone, or the like, or any combinations thereof. The terms also encompass pharmaceutically acceptable, pharmacologically active derivatives of those active agents specifically mentioned herein, including, but not limited to, salts, esters, amides, prodrugs, active metabolites, isomers, fragments and analogs. When the terms "biologically active agent," "biological agent" and "agent" are used, then, or when an active agent is specifically identified, it is intended to include the active agent per se as well as pharmaceutically acceptable, pharmacologically active salts, esters, amides, prodrugs, active metabolites, isomers, fragments and analogs.

As used herein, a subject is defined as an animal, including a mammal, typically a human.

As used herein, quantitative delivery refers to delivery of a substantial portion of the amount administered, and is typically, greater than 50%, 60%, 70%, 80%, 85%, 90%, 91%, 92%, 93%, 94%, 95%, 96%, 97%, 98%, or 99%.

As used herein, therapeutically effective amount refers to an amount of the active agent for a desired therapeutic, prophylactic, or other biological effect or response when a composition is administered to a subject in a single dosage form. The particular amount of active agent in a dosage will vary widely according to conditions such as the nature of the active agent, the nature of the condition being treated, the age and size of the subject.

As used herein, an emulsion is defined as a colloidal dispersion of two immiscible liquids, such as oil and water, in the form of droplets. The emulsions are generally stabilized by an interfacial film of surface active agents or surfactant molecules, such as polysorbate-80 and the stability of an emulsion can be determined by well known routine methods.

As used herein, surfactants (or "surface-active agents") are chemical or naturally occurring entities which, when dissolved in an aqueous solution, reduce the surface tension of the solution or the interfacial tension between the aqueous phase and the oil phase, to form a stable oil in polar protic solvent, other than water, or polar protic solvent, other than water, in oil emulsion. The surfactant molecules are amphiphilic and contain hydrophilic head groups and hydrophobic tails. The surfactant molecules form various macro-molecular structures in an emulsion, such as micelles, inverse micelles, lipid bilayers (liposomes) and cubosomes. The exact macromolecular structure which is formed depends on the relative sizes of the hydrophilic and hydrophobic regions of the surface active molecules.

Micelle formation is favored when the cross sectional area of the hydrophilic region of the surface active molecule is greater than that of the hydrophobic part of the molecule. For example, sodium palmitate contains a hydrocarbon chain (the hydrophobic portion of the molecule) and an ionic base (the hydrophilic portion of the molecule), and acts as an emulsifying agent that binds certain polar compounds and oil phases. It allows oil and water to be broken into tiny droplets suspended or dispersed in water as spherical micelles, whereby the hydrophilic head groups arrange at the periphery of the sphere and hydrophobic tails are at the center.

When the cross sectional area of the hydrophobic region of the molecule is greater than that of the hydrophilic part of the molecule, the formation of hexagonal phase structures, sometimes referred to as an inverse micelle is favored, e.g., dimyristoyl-phosphatidylethanolamine (DMPE).

For surface active molecules in which the cross sectional area of the hydrophilic region of the molecule is slightly less than, or equal to, that of the hydrophobic part of the molecule, such as many phospholipids (which are amphipathic type of lipids that contain phosphate, that is, molecules containing one phosphate, a glycerol and one or more fatty acids), the formation of bilayers is favored, x., dipalmitoyl-phosphatidylcholine (DPPC). These bilayers are two dimensional sheets in which all of the hydrophobic portions, e.g., acyl side chains, are shielded from interaction with water except those at the ends of the sheet. An energetically unfavorable interaction of the acyl chains with water results in the folding of the bilayers to form three-dimensional vesicles. These vesicles are referred to as "liposomes." Liposomes may be formed as a single bilayer enclosing a single aqueous space (small unilamellar vesicles; SUVS) or may be composed of concentric bilayers with many aqueous spaces alternating with the bilayers (multilamellar vesicles; MLVS). Liposomes can be used to encapsulate both hydrophobic and hydrophilic active agents. Hydrophobic active agents are typically partitioned within the bilayers whereas hydrophilic active agents are typically trapped within the aqueous compartments. The advantages of using liposomes as a carrier/encapsulation system is that they are stable and can protect the active agents from degradation, e.g., by oxygen and digestive enzymes.

As used herein, a "peptide" refers to a protein that is from 2 to about or 40 amino acids in length.

As used herein, a polypeptide refers to a linear organic polymer containing a large number of amino-acid residues bonded together in a chain, forming part of (or the whole of) a protein molecule. Polypeptides include peptides. Proteins are polypeptides.

As used herein, glutathione is a tripeptide containing the three amino acids cysteine, glutamic acid, and glycine.

As used herein, a "delivery vehicle" refers to macromolecular structures in an emulsion, such as micelles, inverse micelles, lipid bilayers (liposomes) and cubosomes or a mixture thereof.

As used herein, "protein is associated with a delivery vehicle" means the mucoadhesive protein is associated with a delivery vehicle via chemical or physical interaction, such as hydrogen bond or van der Waal's forces. The mucoadhesive protein, such as lactoferrin can be for example, associated with the polar head groups of the delivery vehicles, such as micelles via a chemical interaction, such as a hydrogen bond.

As used herein, "agent is associated with a delivery vehicle" means the delivery vehicle contains the agent to be delivered. The agent can be for example, encapsulated in a micelle or encapsulated in the liposome bilayers.

As used herein, viscosity refers to a physical property of fluids that determines the internal resistance to shear forces and is expressed in centipoise (cp).

As used herein, medium chain represents a hydrocarbon chain of $C_8$ to $C_{12}$ and short chain is a hydrocarbon chain of less than $C_8$ and long chain means a hydrocarbon chain of more than $C_{12}$. The polar protic solvent, other than water, phase in the emulsion can be water, aqueous solutions, alcohols and alcohol solutions.

As used herein, the stability of a composition provided herein refers to the length of time at a given temperature that greater than 10%, 20%, 30%, 40%, 50%, 60%, 70%, 80%, 85%, 90%, 91%, 92%, 93%, 94%, 95%, 96%, 97%, 98% or 99% of the initial amount of the agent to be delivered, e.g., glutathione, is present in the composition. Thus, for example, a composition that is stable for 30 days at 25° C. would have greater than 10%, 20%, 30%, 40%, 50%, 60%, 70%, 80%, 85%, 90%, 91%, 92%, 93%, 94%, 95%, 96%, 97%, 98% or 99% of the initial amount of active ingredient present in the composition at 30 days following storage at 25° C.

As used herein, pharmaceutically acceptable derivatives of a compound include salts, esters, enol ethers, enol esters, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

As used herein, pharmaceutically acceptable solvates and hydrates are complexes of a compound with one or more polar protic solvent molecule, in certain embodiments 1 to about 100, in other embodiments 1 to about 10, in further embodiments one to about 2, 3 or 4, solvent molecules.

As used herein, treatment means any manner in which one or more of the symptoms of a condition, disorder or disease are ameliorated or otherwise beneficially altered. Treatment also encompasses any pharmaceutical use of the compositions herein, such as use for treating diabetes.

As used herein, amelioration of the symptoms of a particular disorder by administration of a particular pharmaceutical composition refers to any lessening, whether permanent or temporary, lasting or transient that can be attributed to or associated with administration of the composition.

As used herein, a composition is a mixture of two or more ingredients.

As used herein, "co-surfactant" is used to refer to a surfactant that is used in the provided compositions in combination with the primary surfactant, for example, the water-soluble vitamin E derivative mixtures (compositions) described herein, for example, to improve the emulsification of the provided compositions and/or compounds, for example, to emulsify the ingredients. In one example, the provided compositions can contain at least one surfactant and at least one co-surfactant. Typically, the co-surfactant represents a lower percent, by weight (w/w), of the provided compositions, compared to the surfactant. Thus, the provided compositions typically have a lower concentration of the co-surfactant(s) than of the surfactant.

As used herein, "HLB" refers to a value that is used to index and describe a surfactant according to its relative hydrophobicity/hydrophilicity, relative to other surfactants. A surfactant's HLB value is an indication of the molecular balance of the hydrophobic and hydrophilic portions of the surfactant, which is an amphipathic molecule. Each surfactant and mixture of surfactants (and/or co-surfactants) has an HLB value that is a numerical representation of the relative weight percent of hydrophobic and hydrophilic portions of the surfactant molecule(s). HLB values are derived from a semi-empirical formula. The relative weight percentages of the hydrophobic and hydrophilic groups are indicative of surfactant properties, including the molecular structure, for example, the types of aggregates the surfactants form and the solubility of the surfactant. See, for example, Griffin (1949) J. Soc. Cos. Chem. 1:311. Surfactant HLB values range from 1-45, while the range for non-ionic surfactants typically is from 1-20. The more lipophilic a surfactant is, the lower its HLB value. Conversely, the more hydrophilic a surfactant is, the higher its HLB value.

As used herein, "vitamin E" refers to any naturally occurring or synthetic form of vitamin E, for example, tocopherols and tocotrienols, and can refer to a single form of the compound or a mixture of forms.

As used herein, "water-soluble vitamin E derivative composition," "water-soluble vitamin E derivative," "water-soluble vitamin E derivative surfactant," "water-soluble vitamin E surfactant," and "water-soluble derivative of vitamin E mixture," which are used interchangeably, refer to compositions that contain mixtures of water-soluble forms of vitamin E (vitamin E derivatized with moieties, such as polyalkylene glycol that increase the water solubility of the water-insoluble vitamin E). The mixtures contain dimers and monomers of the vitamin E derivatives. The water-soluble vitamin E derivative mixtures (compositions) include vitamin E (natural or synthetic forms of vitamin E), such as tocopherol derivatives and tocotrienol derivatives. Derivatives of vitamin E, such as polyethylene glycol (PEG)-derivatives previously produced, are manufactured to contain as much monomer form as possible, and to contain minimal amounts of any dimer form (see, e.g., Christiansen et al. (2011) J. Pharm. Sci. 100(5):1773-1782).

In contrast, the high dimer-containing vitamin E derivative mixtures, such as PEG-derivative of vitamin E compositions (also referred to herein as high dimer PEG-derivatives of vitamin E mixtures) employed herein, are manufactured to contain dimer forms. The mixtures described herein contain at least 13%, particularly at least or at least about 20%, 25%, 29%, or more, dimer form of the water-soluble vitamin E derivative. In particular, the water-soluble vitamin E derivative mixtures (compositions) are manufactured to contain between or between about 13 wt % and about or up to 95%, 90%, 85%, 80%, or 75 wt %, particularly at least 29% to 75% or 80%, inclusive, of the water-soluble vitamin E dimer. In general, the high dimer-containing derivatives, such as PEG-derivatives of vitamin E mixtures, such as a high dimer TPGS composition, contain 30%-60%, particularly 35%-52%, dimer, and the remainder is the monomer form and present in less than 5%, generally 3%, 2%, or 1%, are other trace components, such as unreacted reagents, such as vitamin E and the hydrophilic derivatizing moiety.

In general, the high dimer mixtures contain at least 13% of the dimer form and up to 87% monomer form, particularly at least 25% of the dimer form and up to 70% of the monomer form, such as between or between about 25 wt % and 69%, inclusive, of the monomer. Hence, the water-soluble vitamin E derivative mixtures (compositions) (high dimer containing compositions) contain a substantial amount (i.e., 13% or more, particularly 25%, 29%, 35%, 48%, 52%, or more) of the dimer form compared to commercially available forms that are manufactured to provide the monomer form.

As manufactured, the high dimer containing mixtures can include other forms and unreacted components, hence the total amount of dimer and monomer do not necessarily total 100%, by weight, of the composition. It is shown herein that inclusion of at least 13%, 20%, 25%, 29%, or more of the dimer form, and some monomer form, about less than 87%, 69%, 65%, 60%, 55%, or 50% of the monomer with at least 13% dimer, confers advantageous properties on these water-soluble vitamin E derivative mixtures (compositions) not possessed by such compositions that contain lower amounts of the dimer form.

Examples of water-soluble vitamin E derivatives are those formed by covalently attaching a vitamin E moiety, e.g., a tocopherol or tocotrienol, to a hydrophilic moiety, for example, an alkylene glycol, such as a polyethylene glycol (PEG) moiety, via a linker. The compositions as provided herein are manufactured so that the resulting water-soluble vitamin E derivative mixtures (compositions) include a mixture of monomers and dimers of the water-soluble vitamin E derivatives, and contain a substantial amount (compared to prior art preparations), i.e., 13% to 95%, inclusive, such as at least 13%, 20%, 25%, or 29%, up to as much as 75%, 80%, 85%, 90%, 95%, by weight, of the dimer form and generally less than 70%, 65%, 63%, 62%, 61% or 60%, or less of the monomer form. Water-soluble vitamin E derivative mixtures (compositions) include, for example, polyalkylene glycol derivatives of tocopherol, e.g., polyethylene glycol (PEG) derivatives of tocopherol, and polyalkylene glycol derivatives of tocotrienol, e.g., polyethylene glycol (PEG) derivatives of tocotrienol. The water-soluble vitamin E derivatives can include, for example, vitamin E TPGS (D-α-tocopheryl polyethylene glycol succinate), TPGS analogs, TPGS homologs and TPGS derivatives.

As used herein, "tocopherol" and "tocotrienol" refer to any naturally occurring or synthetic form of vitamin E, and can refer to a single compound or a mixture of tocopherols and tocotrienols. Examples of tocopherols include, for example, α-tocopherol, D-α-tocopherol, β-tocopherol, γ-tocopherol and δ-tocopherol. Examples of tocotrienols include, for example, α-tocotrienol, β-tocotrienol, γ-tocotrienol and δ-tocotrienol.

As used herein, a "PEG derivative of vitamin E" or "vitamin E-PEG conjugate" or "vitamin E-PEG derivative," is a compound containing one or more vitamin E moieties (e.g., a tocopherol or tocotrienol) joined by a covalent bond, for example, an ester, ether, amide or thioester bond, to one or more polyethylene glycol (PEG) moieties, via a linker, such as a dicarboxylic or tricarboxylic acid. Exemplary of PEG derivatives of vitamin E are D-α-tocopheryl polyethylene glycol succinate (TPGS), TPGS analogs, TPGS homologs and TPGS derivatives.

As used herein, "tocopheryl polyethylene glycol succinate," "TPGS," "tocopheryl polyethylene glycol succinate surfactant" and "TPGS surfactant" refer to tocopheryl polyethylene glycol conjugates that are formed by covalently joining tocopherol succinate, an ester formed through esterification of tocopherol and succinic acid, to a polyethylene glycol (PEG) moiety via an esterification reaction. The PEG moiety of the TPGS surfactant can be any PEG moiety, for example, a PEG moiety with a molecular weight of between or between about 200 Da to 20,000 Da or about 20,000 Da, for example, PEG moieties having a molecular weight of or about 200, 300, 400, 500, 600, 800, 1000, 3000, 5000, 6000, 8000, 10,000, 20,000 Da, or more; or PEG analogs, including, for example, PEG-NHS (N-hydroxysuccinimide), PEG-aldehyde, PEG-SH, PEG-$NH_2$, PEG-$CO_2H$, and branched PEGs.

As used herein, "TPGS monomer" is a single vitamin E moiety, i.e., D-α-tocopherol, covalently joined to a water-soluble moiety, such as a polyethylene glycol, through a succinate linker. "TPGS monomer" can also refer to TPGS analogs, homologs or derivatives, including any other water-soluble vitamin E derivatives described herein. A "TPGS dimer" is made up of two vitamin E moieties, i.e., D-α-tocopherol, covalently joined to a water-soluble moiety, such as a polyethylene glycol, through one or more succinate linkers (shown below). "TPGS dimer" can also refer to TPGS analogs, homologs or derivatives, including any other water-soluble vitamin E derivatives described herein. The esterification reaction between the vitamin E moiety, for example, D-α-tocopheryl succinate, and PEG results in a highly complex crude product that contains a mixture of TPGS monomer, unreacted PEG, unreacted vitamin E (e.g., D-α-tocopheryl succinate), catalyst, and TPGS dimer, formed when a second molecule of the vitamin E moiety reacts with the terminal hydroxyl group of a PEG moiety already conjugated to TPGS monomer via a linker. For purposes herein, mixtures are produced by performing the reaction under conditions that result in higher amounts of the TPGS dimer being produced as compared to prior art preparations. In addition, the TPGS dimer can be purified and the amounts increased. The water-soluble vitamin E derivative mixtures (compositions) where the vitamin E derivative is TPGS, as described herein, contain a mixture of TPGS monomer and TPGS dimer, and contain more than 12%, but generally at least 20%, 25%, 29%, 35%, or more, TPGS dimer, up to as much as 95% or about 95% TPGS dimer, but typically up to about 75%. The remainder of the composition contains the TPGS monomer and can contain unreacted starting materials and catalyst. Similarly, water-soluble vitamin E derivative mixtures (compositions) containing vitamin E derivatives other than TPGS contain mixtures of dimer and monomer.

As used herein, probiotics are microorganisms that are sold to provide and/or confer health benefits when consumed. Probiotics include bacteria of the *Bifidobacterium* and *Lactobacillus* genera.

B. Compositions

Provided are MAPT compositions for mucosal delivery. Also provided are MAPT compositions that do not contain any water; these compositions contain a polar protic solvent, such as glycerin, for the polar phase. These compositions contain agents for delivery that are sensitive to water or degraded by water that generally are provided as dry powders. These MAPT compositions, provide a flowing liquid form of such agents. Such agents include sulfur-containing proteins and probiotics.

Among the compositions are MAPT compositions that contain a PEG-derivative of vitamin E, formulated by addition to the polar phase. In particular, the PEG-derivative of vitamin E is a high dimer mixture, as described herein. The remaining ingredients for such compositions can be the same as those described in U.S. Pat. Nos. 8,252,323, 7,906,140 and 8,414,914.

Also provided are powders that contain a PEG-derivative of vitamin E, such as TPGS, and a mucoadhesive protein, such as lactoferrin, and optionally other ingredients. Probiotics are among such ingredients. The probiotics are formulated in the oil phase with the lactoferrin.

1. Mucosal Delivery

Provided herein are compositions and methods for mucosal delivery of agents, particularly agents that are normally difficult to administer or ineffective when administered orally or nasally. The compositions provided herein contain one or more mucoadhesive proteins that impart a mucoadhesive property to the composition. Contacting a mucosal surface in a subject with a composition results in delivery of the composition, including active and inactive components into circulation. The compositions provided herein are for delivery of agents, such as biologically active agents, through mucosa, such as oral, nasal or intestinal mucosa.

Mucosal delivery systems offer benefits over other methods of delivery. For example, absorption through the mucous membrane leads the delivered active agent directly into the circulatory system. This allows such agents, in certain embodiments, to bypass the gastrointestinal tract as well as first pass liver metabolism. Secondly, the biologically active agents such as drugs directly enter the circulatory system, which allows the therapeutic to be rapidly transported to the site of need. The faster the drug reaches its target area, the faster it can begin to elicit its desired effect. Further, the avoidance of the gastrointestinal tract and first pass metabolism means that much less of the drug can be administered to achieve the same effect, allowing for lower dosages to be administered and fewer side effects.

Modes of mucosal administration include oral and nasal administrations. Those of skill in the art are familiar with a variety of modes of administration (see, e.g., Almeida et al. Journal of Drug Targeting 3, 456-467 (1996), which provides a review of mucosal administration of vaccines in general, and nasal administration of vaccines in particular). The compositions upon contacting with the mucosal surface, adhere thereto or penetrate through the mucosal surface, for an amount of time sufficient to achieve quantitative delivery of the composition, including, but not limited to less than 1 minute up to more than 3 hours. Various parameters known in the art can be used for measurement of mucoadhesion. Such parameters include, but are not limited to, mechanical binding to mucous membrane per se or the degree of biological effect of an agent delivered. The compositions are formulated to adhere to or penetrate into the mucosal surface for at least about 30 sec or 1, 2, 3, 4, 5, 10, 15, 20, 25, 30, 35, 40, 50, 60, 70, 80, 90, 100, 120, or 150 minutes or up to more than 180 minutes after being delivered to the mucosa. In certain embodiments, compositions are formulated to adhere to or penetrate into the mucosal surface for about 1, 2, 3, 4, 5, 6, 7, 8, 9, 10, 12, 14, 16, 18, 20, 22, 24 or more hours.

Mucosal delivery of agents can be effected either in the absence or in the presence of a carrier. Mucosal administration in the presence of a carrier serves various purposes, such as controlled release of biologically active molecules, targeting of biologically active molecules to specific tissues, and facilitating penetration into the mucosal layer.

2. MAPT Compositions

The compositions provided herein, which provide mucosal delivery of agents, are formulated as emulsions, including oil in polar protic solvent, other than water, and polar protic solvent, other than water, in oil emulsions. The MAPT compositions do not contain water, but instead contain a polar protic solvent, such as glycerin, permitting liquid formulation of water-sensitive agents.

In preparing the compositions, an agent to be delivered is dissolved either in the oil phase or the polar protic solvent, other than water, phase prior to forming an emulsion. Typically the polar protic solvent is glycerin. Other polar protic solvents include, for example, methanol, ethanol, glycerin and propylene glycol. To prepare the compositions the oil phase and polar protic solvent phases are prepared separately. The polar protic solvent in this phase is typically 30% to 95%, such as 40%-80%, such 60%-70%, by weight of the final composition. The polar protic phase includes the mucoadhesive protein, such as the lactoferrin in an amount that is about 2% or 3% to 10%, 11%, or 12% by weight of the final composition. Components soluble in oil are added to the oil phase and components soluble in polar solvents are added to the polar protic solvent phase. The oil phase also can include a co-solvent; co-solvents include glycerin, in an amount that is typically about 2% or 3% to 8% by weight of the final emulsion composition. Thus, the emulsion compositions can include the glycerin from the polar protic phase and the glycerin that is included in the oil phase as co-solvent. The compositions optionally include additional ingredients, such as surface active agents for stabilizing the emulsions. The oil phase also includes surfactants, such as a PEG-derivative of vitamin E, such as d-alpha tocopheryl polyethylene glycol succinate (TPGS), and/or other surfactants, such as sucrose fatty acid ester surfactants and polysorbates, such as polysorbate 80. The surfactants can be included in the polar protic solvent phase. In particular, the compositions include PEG-derivative of vitamin E, such as d-alpha tocopheryl polyethylene glycol succinate (TPGS), and particularly the high dimer TPGS, particularly high dimer TPGS-1000, as described herein and in U.S. Publication No. US-2014-0271593, and published International PCT Publication No. WO 2014/151109. The powder formulations and formulations for spray drying, described below, also include TPGS, which, as shown herein, protects the mucoadhesive protein, such as lactoferrin from heat during spray drying, thereby advantageously permitting preparation of powders.

The total amount of surfactant, which can be a mixture, such as TPGS and polysorbate 80, can be between about or at 3%-15% by weight of the composition, particularly between about 5-15% or 3% to 10% by weight of the composition, such as 3-10% TPGS in the oil phase, and 1-3% other surfactant, such as polysorbate 80, in the polar protic solvent phase.

The agent for delivery is added to the phase in which it is most soluble, and in an amount that will deliver the desired dosage when ingested. Typically, the agent for delivery is included in an amount between about 0.1 to 15%, by weight, such as, at least 1%, 2,%, 3%, 4%, 5%, 6%, 7%, 8%, 9%, 10%, 11%, 11.1%, 11.5%, 12%, or 15%, such as 6-12%, 7-12%, 8-12%, 8-11.5, or 8-11.1% by weight.

MAPT compositions provided herein can have a wide range of viscosities, typically ranging from about 1 cps; 10 cps; 50 cps; 100 cps; 300 cps; 500 cps; 750 cps; 1000 cps; 3000 cps; 6000 cps; 8000 cps; 10,000 cps; 20,000 cps; 30,000 cps; 40,000 cps; 50,000 cps; 60,000 cps; 70,000 cps; 80,000 cps; 90,000 cps; 100,000 cps; 150,000 cps; 200,000 cps; 130,000 cps; 250,000 cps; or 280,000 cps up to 100,000 cps, 150,000 cps, 200,000 cps, 250,000 cps or more than 500,000 cps at 72° F. (room temperature). The viscosity of the compositions can be measured by methods known to those of skill in the art, including measurement by using a viscometer such as Brookfield LVDV-I+ viscometer and T spindles with a heliopath adapter.

In the MAPT compositions provided herein, oil phase, aqueous phase and emulsifier can be used in a wide range of ratios to make the emulsions. The oil-in-polar protic solvent, other than water, emulsions contain, by weight, at least 25% of polar protic solvent, other than water, by weight, in one embodiment between 30% and 80% and in another embodiment between 40% and 95%, and particularly 50% to 70%, such as 60%-65%, by weight. In particular, the polar protic solvent is glycerin. The oil phase, in the oil in polar protic solvent, other than water, emulsions, constitutes at least 1%, 2%, 3%, 4%, 5%, 6%, 7%, 8%, 9%, 10%, 15%, 20%, 25%, 30% or more by weight of the emulsion. The emulsifier or surfactant in the emulsions is at least 0.5%, 1%, 2%, 3%, 4%, 5%, 6%, 7%, 8%, 9%, 10%, 15%, 20%, or 25% by weight of the emulsion. The oil phase also can include a co-solvent, which can be glycerin (additional to the glycerin used is the protic solvent), in an amount up to about 10%, by weight, such as 3% to 8%, whereby the total amount of glycerin in the final composition is between about or at 35% to 95%, such as 60% to 80%, particularly, 65% to 70%, or 65% to 75% or 70% to 75%.

The water-in-oil emulsions contain at least 25% of oil by weight, in one embodiment between 30% and 80% and in another embodiment between 40% and 95% of oil by weight. The polar protic solvent, other than water, phase in the polar protic solvent, other than water, in oil emulsions is at least 1%, 2%, 3%, 4%, 5%, 6%, 7%, 8%, 9%, 10%, 15%, 20%, 25%, 30% or more by weight of the emulsion. The emulsifier or surfactant in the emulsions is at least 0.5%, 1%, 2%, 3%, 4%, 5%, 6%, 7%, 8%, 9%, 10%, 15%, 20%, or 25% by weight of the emulsion.

The compositions provided herein also can include one or more other additives, such as a polymer, a cosolvent, an antioxidant, an antiseptic, a buffering agent, a chelating agent, a colorant, a flavorant, an odorant, an osmotic modifier, a preservative, a solubilizer, a tonicifier, a trace element, a viscomodulator and a mixture thereof. Such additional additives can be present in the oil phase, the aqueous phase or both. As noted above, cosolvents include glycerin, which can be included in the oil phase to facilitate dissolution of ingredients. This glycerin is in addition to the polar protic solvent that constitutes the polar phase of the emulsion in which the water-soluble and polar components are provided.

a. Mucoadhesive Proteins

The compositions contain one or more mucoadhesive proteins. The mucoadhesive proteins for use in the compositions and methods provided herein include any protein that imparts a mucoadhesive property to the composition whereby the composition when administered to a subject's mucosal surface, such as oral or nasal mucosa, adheres or penetrates into the mucosal epithelium of the subject for a period of time sufficient to achieve quantitative delivery of an agent to be delivered. In certain embodiments, the compositions adhere to or penetrate through the mucosal membrane for a period of time sufficient to locally deliver a therapeutically-effective amount of an active agent in the composition. Adhesion of mucoadhesive protein to the mucous membrane occurs primarily via secondary chemical bonds, such as hydrogen bonding and Van der Waal forces.

Any mucoadhesive protein that is biologically compatible can be employed. Mucoadhesive proteins for use herein include, but are not limited to natural or synthetic proteins, polypeptides or fragments thereof that possess the mucoadhesive property. Mucoadhesive proteins can be screened for their ability to be used as mucoadhesives for mucosal delivery of compositions provided herein according to the methodology described in Smart et al., 1982 *J. Pharm. Pharmacol.* 34:70P and Smart et al., 1984 *J. Pharm. Pharmacol.* 36:295. The methodology involves estimating values of adhesive strength between the mucoadhesive protein and the mucous membrane.

In certain embodiments, the mucoadhesive proteins are selected from a family of mucin proteins and transferrins. In certain embodiments, the mucoadhesive protein is from the transferrin family and is selected from bovine lactoferrin, human lactoferrin, lactoferrin binding proteins, recombinant human lactoferrin, lactoferricin, lactoferricin b, transferrin binding proteins, bovine transferrin, ovotransferrin, neutrophil granules, apo-lactoferrin and lanthanide-lactoferrin. In certain embodiments, the mucoadhesive proteins are selected from among lactoferrin, lactoferrin binding proteins, recombinant lactoferrin, lactoferricin, lactoferricin b, transferrin binding proteins, transferrin, ovotransferrin, neutrophil granules, apo-lactoferrin, immunoglobulin, albumin and lanthanide-lactoferrin. In certain embodiments, the mucoadhesive protein is selected from albumin, immunoglobulin and lactoferrin.

In certain embodiments, the mucoadhesive protein for use in the compositions and methods provided herein is lactoferrin. In certain embodiments, the compositions contain one, two or three mucoadhesive proteins. In certain embodiments, the compositions contain one mucoadhesive protein. In certain embodiments, the mucoadhesive protein in the compositions provided herein is present in an amount sufficient to confer a mucoadhesive property to the composition.

The mucoadhesive proteins can associate with the delivery vehicle via chemical or physical interaction. For example, the mucoadhesive protein can be hydrogen bonded with polar head groups of the micelles or the liposomes or other vehicles that are present in the emulsion in the compositions provided herein. Such compositions when administered either orally or nasally, to a subject in need thereof, adhere to or penetrate through the mucosal membrane via chemical or physical bond, such as secondary chemical bonds, including hydrogen bonding and Van der Waal forces, thereby providing sustained or prolonged coating of the composition on the epithelium of the oral cavity or nasal cavity depending on the mode of administration. The sustained coating of the composition allows for increased contact time between the composition and the epithelial layer, which in turn results in enhanced absorption of the active agent in to the mucosal layer.

The amount of mucoadhesive protein in the compositions provided herein, is an amount that results in quantitative delivery of an agent formulated therewith. The amount to be added can vary depending upon the agent delivered and other components of a composition, but it can be determined empirically by formulating compositions and testing them for delivery using any suitable assay known to those of skill in the art or as described herein.

Typically, the mucoadhesive protein is present at a concentration of about 0.05% by weight up to about 80%, generally at least 0.1, 0.2, 0.3, 0.4, 0.5, 1, 2, 3, 4, 5, 6, 7, 8, 9, 10, 11, 12, 13, 14, 15, 20, 25, 30, or 40% by weight up to about 50% by weight, such as 1-12%, 2-12%, 5-13%, 6-13%, 1-20%, or 5-15%, of the total weight of the composition. In other embodiments, the mucoadhesive protein is present at a concentration of about 0.1% by weight up to about 30% by weight of the total weight of the composition. In other embodiments, the mucoadhesive protein is present at a concentration of about 0.1% by weight up to about 20% by weight of the total weight of the composition. In other embodiments, the mucoadhesive protein is present at a concentration of about 0.05% by weight up to about 15% by weight of the total weight of the composition. In other embodiments, the mucoadhesive protein is present at a concentration of about 0.05% by weight up to about 12% by weight of the total weight of the composition. In other embodiments, the mucoadhesive protein is present at a concentration of about 0.05% by weight up to about 10% by weight of the total weight of the composition. In other embodiments, the mucoadhesive protein is present at a concentration of about 0.05% by weight up to about 8% by weight of the total weight of the composition. In other embodiments, the mucoadhesive protein is present at a concentration of about 0.05% by weight up to about 5% by weight of the total weight of the composition. In other embodiments, the mucoadhesive protein is present at a concentration of about 8% by weight up to about 12%, by weight of the total weight of the composition. In other embodiments, the mucoadhesive protein is present at a concentration of at least about 3%, by weight, to about 5%, by weight, about 9% by weight up to about 10% by weight of the total weight of the composition. In other embodiments, the mucoadhesive protein is present at a concentration of up to about 15% by weight, such a 0.5% or 1% up to 15%, such as 3% to 5%, by weight, of the total weight of the composition. In other embodiments, the mucoadhesive protein is present at a concentration of about 12% by weight of the total weight of the composition. In other embodiments, the mucoadhesive protein is present at a concentration of about 10% by weight of the total weight of the composition. In other embodiments, the mucoadhesive protein is present at a concentration of about 9.5% by weight of the total weight of the composition. In other embodiments, the mucoadhesive protein is present at a concentration of about 9% by weight of the total weight of the composition. In other embodiments, the mucoadhesive protein is present at a concentration of about 8% by weight of the total weight of the composition. In other embodiments, the mucoadhesive protein is present at a concentration of about 6% by weight of the total weight of the composition. In other embodiments, the mucoadhesive protein is present at a concentration of about 4% by weight of the total weight of the composition. In other embodiments, the mucoadhesive protein is present at a concentration of about 2% by weight of the total weight of the composition. In other embodiments, the mucoadhesive protein is present at a concentration of about 1% by weight of the total weight of the composition. In other embodiments, the mucoadhesive protein is present at a concentration of about 0.8% by weight of the total weight of the composition. In other embodiments, the mucoadhesive protein is present at a concentration of about 0.6% by weight of the total weight of the composition. In other embodiments, the mucoadhesive protein is present at a concentration of about 0.4% by weight of the total weight of the composition. In other embodiments, the mucoadhesive protein is present at a concentration of about 0.1% by weight of the total weight of the composition. In other embodiments, the mucoadhesive protein is present at a concentration of about 0.05% by weight of the total weight of the composition.

b. Oils

The oils for use in the compositions include any oil obtained from a natural or synthetic source that is suitable for consumption by a subject. Oils suitable for administration to subjects, including humans, are known. Any such oil can be used. The oil can be of vegetable or animal origin. The oil phase also can be synthetic or semisynthetic oils that are nontoxic to a subject. Exemplary of oils for use herein include, but are not limited to mono-, di- and triglycerides, fatty acids, such as oleic, linoleic, palmitic, stearic, conjugated forms thereof and their esters, ethers and esters of propylene glycol and other polyols. The oil phase in the emulsion provided herein can contain any nontoxic oil, biocompatible oil, which includes, but is not limited to mono-, di- and triglycerides, fatty acids and their esters, ethers and esters of propylene glycol or other polyols. The fatty acids and esters (used as such or where they form part of a glyceride) can be short chain, medium chain or long chain. Exemplary oils include, but are not limited to, vitamin E oil, flaxseed oil, CLA, borage oil, rice bran oil, d-limonene, canola oil, corn oil, MCT oil, and oat oil. Other oils also can be used.

In certain embodiments, the oils are short, medium or long chain triglycerides. In certain embodiments, the oils are medium chain triglycerides (MCTs). In certain embodiments, the MCT is tricaprylic triglyceride ester (also known as Neobee® M5). Exemplary sources for oils contemplated herein include, but are not limited to All Spice, Almond, Anise, Apple, Apricot, Avocado, Basil, Bayberry, Benzoin, Bergamot, Borage Seed, Cajeput, Calendula, Canola, Carnation, Carrot seed, Cassia bark, Castor, Cayenne, Cedarwood, Chamomile, Cinnamon, Citronella, Conjugated Linolenic Acid, Clary sage, Clove bud, Coconut, Cod Liver, Corn, Cranberry, Cypress, Evening Primrose, Eucalyptus, Evergreen, Fir, Fish 18:12, Flax Seed, Frangipani, Frankincense, Freesia, Gardenia, Ginger, Grape Seed, Grapefruit, Heather, Honeysuckle, Hyacinth, Jasmine, Jojoba, Juniper berry, Lavender, Lecithin, Lemon, Lemon balm, Lemon, verbena, Lemongrass, Lilac, Lily of the valley, Lime, Magnolia, MCT, Menthol, Mulberry, Musk, Myrrh Oat, Olive, Orange, Oregano, Palm, Patchouli, Peach, Pennyroyal, Peppermint, Petitgrain, Pine, Pumpkin Seed, Rice Bran, Rose, Rosemary, Rosewood, Safflower, Sage, Salmon, Sandalwood, Sesame, Shark Liver, Soy Bean, Spearmint, Squalene, Strawberry, Sunflower, Tangerine, Tea tree, Thuja (Cedar leaf), Thyme, Tuna, Vanilla, Vitamin E, Wheat Germ, Wintergreen and Ylang ylang. In certain embodiments, the oil phase contains oat oil and tri caprylic triglyceride ester (also known as Neobee® M5).

The oil is present in an amount sufficient to dissolve the oil soluble ingredients in the composition. The amount generally is a function of the locus of administration, the agent to be administered and other such parameters and can be empirically determined. For example, in some embodiments, the oil is present at a concentration of about 1%, 2%, 3%, 4%, 5%, 10%, 20%, 25%, 30%, 35%, 40%, 45%, 50%, 55%, 60%, 65%, 70%, 75%, 80%, 85%, 90%, 95% or more by weight. Thus, in certain embodiments, the oil is present at about 3, 4, or 5% by weight up to about 90% by weight of the total weight of the composition. In other embodiments, the oil is present at a concentration of about 3%, 4%, or 5% by weight up to about 85% by weight of the total weight of the composition. In other embodiments, the oil is present at a concentration of about 5% by weight up to about 70% by weight of the total weight of the composition. In other embodiments, the oil is present at a concentration of about 5% by weight up to about 50% by weight of the total weight of the composition. In other embodiments, the oil is present at a concentration of about 5% by weight up to about 45% by weight of the total weight of the composition. In other embodiments, the oil is present at a concentration of about 5% by weight up to about 40% by weight of the total weight of the composition. In other embodiments, the oil is present at a concentration of about 5% by weight up to about 35% by weight of the total weight of the composition. In other embodiments, the oil is present at a concentration of about 5% by weight up to about 30% by weight of the total weight of the composition. In other embodiments, the oil is present at a concentration of about 5% by weight up to about 20% by weight of the total weight of the composition. In other embodiments, the oil is present at a concentration of about 45% by weight of the total weight of the composition. In other embodiments, the oil is present at a concentration of about 40% by weight of the total weight of the composition. In other embodiments, the oil is present at a concentration of about 35% by weight of the total weight of the composition. In other embodiments, the oil is present at a concentration of about 30% by weight of the total weight of the composition. In other embodiments, the oil is present at a concentration of about 20% by weight of the total weight of the composition. In other embodiments, the oil is present at a concentration of about 10% by weight of the total weight of the composition. In other embodiments, the oil is present at a concentration of about 7% by weight of the total weight of the composition. In other embodiments, the oil is present at a concentration of about 5% by weight of the total weight of the composition.

c. Surface Active Agents

The compositions provided herein can contain one or more surface active agents that are added in an amount sufficient to form a stable emulsion or facilitate such formation. The appropriate amount of surface active agent is a function of the agent for delivery and other components present in the emulsion, since some agents can have self-emulsifying properties and other agents and components affect surface tension.

The surface active agents for use herein are substances which, when dissolved in an aqueous solution, reduce the surface tension of the solution or the interfacial tension between the aqueous phase and the oil phase, to form a stable oil in polar protic solvent, other than water, or polar protic solvent, other than water, in oil emulsion. The surfactant molecules are amphiphilic and contain hydrophilic head groups and hydrophobic tails. The surfactant molecules form various macro-molecular structures in an emulsion, such as micelles, inverse micelles, lipid bilayers (liposomes) and cubosomes. The exact macromolecular structure which is formed depends on the relative sizes of the hydrophilic and hydrophobic regions of the surface active molecule. In certain embodiments, the surface active agent is selected from sodium lauryl sulfate; sorbitan laurate, sorbitan palmitate, sorbitan stearate (available under the tradename Span® 20, 40, 60 etc.); polysorbates such as polyoxyethylene (20) sorbitan monolaurate, polyoxyethylene (20) sorbitan monopalmitate, polyoxyethylene (20) sorbitan monostearate (available under the tradename TWEENS® 20, 40, 60 etc.); benzalkonium chloride, mixed chain phospholipids, cationic lipids, oligolipids, phospholipids, carnitines, sphingosines, sphingomyelins, ceramides, glycolipids, lipoproteins, apoproteins, amphiphilic proteins, amphiphilic peptides, amphiphilic synthetic polymers, and combinations thereof. Other exemplary surface active agents for use herein include, but are not limited to:

i) Natural lipids, i.e. Cholesterol, Sphingosine and Derivatives, Gangliosides, Sphingosine derivatives (Soy Bean), Phytosphingosine and derivatives (Yeast), Choline (Phosphatidylcholine), Ethanolamine (Phosphatidylethanolamine), Glycerol (Phosphatidyl-DL-glycerol), Inositol (Phosphatidylinositol), Serine (Phosphatidylserine (Sodium Salt)), Cardiolipin, Phosphatidic Acid, Egg Derived, Lyso (Mono Acyl) Derivatives, (Lysophosphatides), Hydrogenated Phospholipids, Lipid Tissue Extracts, ii) Synthetic lipids, i.e. Asymmetric Fatty Acid, Symmetric Fatty Acid—Saturated Series, Symmetric Fatty Acid—Unsaturated Series, Acyl Coenzyme A (Acetoyl Coenzyme A, Butanoyl Coenzyme A, Crotanoyl Coenzyme A, Hexanoyl Coenzyme A, Octanoyl Coenzyme A, Decanoyl Coenzyme A, Lauroyl Coenzyme A, Myristoyl Coenzyme A, Palmitoyl Coenzyme A, Stearoyl Coenzyme A, Oleoyl Coenzyme A, Arachidoyl Coenzyme A, Arachidonoyl Coenzyme A, Behenoyl Coenzyme A, Tricosanoyl Coenzyme A, Lignoceroyl Coenzyme A, Nervonoyl Coenzyme A, Hexacosanoyl Coenzyme A, iii) Sphingolipids, i.e. D-erythro (C-18) Derivatives (Sphingosine, such as: D-erythro Sphingosine (synthetic), Sphingosine-1-Phosphate, N,N Dimethylsphingosine, N,N,N-Trimethylsphingosine, Sphingosylphosphorylcholine, Sphingomyelin and Glycosylated Sphingosine), Ceramide Derivatives (Ceramides, D-erythro Ceramide-1-Phosphate, Glycosulated Ceramides), Sphinganine (Dihydrosphingosine) (Sphinganine-1-Phosphate, Sphinganine (C20), D-erythro Sphinganine, N-Acyl-Sphinganine C2, N-Acyl-Sphinganine C8, N-acyl-Sphinganine C16, N-Acyl-Sphinganine C18, N-Acyl-Sphinganine C24, N-Acyl-Sphinganine C24:1), Glycosylated (C18) Sphingosine and Phospholipid Derivatives (Glycosylated—Sphingosine) (Sphingosine, β D-Glucosyl, Sphingosine, g D-Galactosyl, Sphingosine, βD-Lactosyl), Glycosylated—Ceramide (D-Glucosyl-β1-1' Ceramide (C8), D-Galactosyl-β1-1' Ceramide (C8), D-Lactosyl-β1-1' Ceramide (C8), D-Glucosyl-β1-1' Ceramide (C12), D-Galactosyl-β1-1' Ceramide (C12), D-Lactosyl-β1-1' Ceramide (C12)), Glycosylated—Phosphatidylethanolamine (1,2-Dioleoyl-sn-Glycero-3-Phosphoethanolamine-N-Lactose), D-erythro (C17) Derivatives (D-erythro Sphingosine, D-erythro Sphingosine-1-phosphate), D-erythro (C20) Derivatives (D-erythro Sphingosine), L-threo (C18) Derivatives (L-threo Sphingosine, Safingol (L-threo Dihydrosphingosine)), Sphingosine Derivatives (Egg, Brain & Milk) (D-erythro-Sphingosine, Sphingomyelin, Ceramides, Cerebrosides, Brain Sulfatides), Gangliosides (Gangliosides Structures, Gangliosides—Ovine Brain, Gangliosides—Porcine Brain), Sphingosine Derivatives (Soy Bean) (Glucosylceramide), Phytosphingosine Derivatives (Yeast) (Phytosphingosine, D-ribo-Phytosphingosine-1-Phosphate, N-Acyl Phytosphingosine C2, N-Acyl Phytosphingosine C8, N-Acyl Phytosphingosine C18, iv) Acyl coenzyme A, i.e. Acetoyl Coenzyme A (Ammonium Salt), Butanoyl Coenzyme A (Ammonium Salt), Crotanoyl Coenzyme A (Ammonium Salt), Hexanoyl Coenzyme A (Ammonium Salt), Octanoyl Coenzyme A (Ammonium Salt), Decanoyl Coenzyme A (Ammonium Salt), Lauroyl Coenzyme A (Ammonium Salt), Myristoyl Coenzyme A (Ammonium Salt), Palmitoyl Coenzyme A (Ammonium Salt), Stearoyl Coenzyme A (Ammonium Salt), Oleoyl Coenzyme A (Ammonium Salt), Arachidoyl Coenzyme A (Ammonium Salt), Arachidonoyl Coenzyme A (Ammonium Salt), Behenoyl Coenzyme A (Ammonium Salt), Tricosanoyl Coenzyme A (Ammonium Salt), Lignoceroyl Coenzyme A (Ammonium Salt), Nervonoyl Coenzyme A (Ammonium Salt), Hexacosanoyl Coenzyme A (Ammonium Salt), Docosahexaenoyl Coenzyme A (Ammonium Salt), v) Oxidized lipids, i.e. 1-Palmitoyl-2-Azelaoyl-sn-Glycero-3-Phosphocholine, 1-O-Hexadecyl-2-Azelaoyl-sn-Glycero-3-Phosphocholine, 1-Palmitoyl-2-Glutaroyl-sn-Glycero-3-Phosphocholine (PGPC), 1-Palmitoyl-2-(9'-oxo-Nonanoyl)-sn-Glycero-3-Phosphocholine, 1-Palmitoyl-2-(5'-oxo-Valeroyl)-sn-Glycero-3-Phosphocholine, vi) Ether lipids, i.e.: Diether Lipids (Dialkyl Phosphatidylcholine, Diphytanyl Ether Lipids), Alkyl Phosphocholine (D odedylphosphocholine), O-Alkyl diacylphosphatidylcholinium (1,2-Diacyl-sn-Glycero-3-Ethylphosphocholine), Synthetic PAF & Derivatives (1-Alkyl-2-Acyl-Glycero-3-Phosphocholine & Derivatives), vii) Fluorescent lipids, i.e.: Glycerol Based (Phosphatidylcholine (NBD), Phosphatidic Acid (NBD), Phosphatidylethanolamine (NBD), Phosphatidylglycerol (NBD), Phosphatidylserine (NBD)), Sphingosine Based (Ceramide (NBD), Sphingomyelin (NBD), Phytosphingosine (NBD), Galactosyl Cerebroside (NBD)), Headgroup Labeled Lipids (Glycerol Based) (Phosphatidylethanolamine (NBD), Phosphatidylethanolamine (Lissamine Rhodamine B), Dioleoyl Phosphatidylethanolamine (Dansyl, Pyrene, Fluorescein), Phosphatidylserine (NBD), Phosphatidylserine (Dansyl)), 25-NBD-Cholesterol, viii) Other lipids including, but not limited to Lecithin, Ultralec-P (ADM), Soy powder, and ix) Surfactants including, but not limited to polyethylene glycol 400; sodium lauryl sulfate; sorbitan laurate, sorbitan palmitate, sorbitan stearate (available under the tradename Span® 20-40-60 etc.); polysorbates such as polyoxyethylene (20) sorbitan monolaurate, polyoxyethylene (20) sorbitan monopalmitate, polyoxyethylene (20) sorbitan monostearate (available under the tradename TWEENS® 20-40-60 etc.); benzalkonium chloride.

In certain embodiments, the phospholipids for use are phosphatidylcholines, phosphatidylethanolamines, phosphatidylserines, phosphatidylglycerols, phosphatidylinositols, phosphatidic acids, mixed chain phospholipids, lysophospholipids, hydrogenated phospholipids, partially hydrogenated phospholipids, and mixtures thereof.

In certain embodiments, the surface active agent is selected from polysorbate-80, lecithin and phosphatidylcholine. The surface active agents are present in an amount sufficient to form a stable emulsion.

The amount of surface active agent can be empirically determined and is a function of the agent selected and the desired form of the resulting composition. The amount include can be from less than 0.1% by weight up to 35% or more. In certain embodiments, the surface active agent is present at a concentration of about 1%, 2%, 3%, 4%, 5%, 6%, 7%, 8%, 9%, 10%, 15%, 20% or 25% by weight up to about 30% by weight of the total weight of the composition. In certain embodiments, the surface active agent is present at a concentration of about 1% by weight up to about 20% by weight of the total weight of the composition. In certain embodiments, the surface active agent is present at a concentration of about 1% by weight up to about 15% by weight of the total weight of the composition. In other embodiments, the surface active agent is present at a concentration of about 1% by weight up to about 10% by weight of the total weight of the composition. In other embodiments, the surface active agent is present at a concentration of about 1% by weight up to about 8% by weight of the total weight of the composition. In other embodiments, the surface active agent is present at a concentration of about 1% by weight up to about 6% by weight of the total weight of the composition. In other embodiments, the surface active agent is present at a concentration of about 1% by weight up to about 4% by weight of the total weight of the composition. In other embodiments, the surface active agent is present at a concentration of about 20% by weight of the total weight of the composition. In other embodiments, the surface active agent is present at a concentration of about 15% by weight of the total weight of the composition. In other embodiments, the surface active agent is present at a concentration of about 13% by weight of the total weight of the composition. In other embodiments, the surface active agent is present at a concentration of about 11% by weight of the total weight of the composition. In other embodiments, the surface active agent is present at a concentration of about 8% by weight of the total weight of the composition. In other embodiments, the surface active agent is present at a concentration of about 6% by weight of the total weight of the composition. In other embodiments, the surface active agent is present at a concentration of about 4% by weight of the total weight of the composition. In other embodiments, the surface active agent is present at a concentration of about 2% by weight of the total weight of the composition. In other embodiments, the surface active agent is present at a concentration of about 1% by weight of the total weight of the composition.

The stable emulsions provided herein can contain one or more delivery vehicles selected from among micelles, liposomes and cubosomes and mixtures thereof, that encapsulate the active agent. The delivery vehicles encapsulating the active agent are then absorbed in the epithelium where the active agent is delivered.

d. PEG-Derivatives of Vitamin E

PEG-derivatives of vitamin E, which are surface active agents are contemplated for use in the MAPT compositions herein, and also in the compositions for spray drying compositions that contain mucoadhesive proteins, such as transferrin, such as lactoferrin. It is shown herein that the PEG-derivatives of vitamin E, such as TPGS, protect the mucoadhesive proteins, from degradation in elevated temperatures, such as those that occur during spray drying.

In particular, TPGS is employed. TPGS includes the TPGS that is commercially available, which is manufactured to maximize the concentration of monomer (such as those sold by Eastman), and those that are manufactured so that the resulting water-soluble vitamin E derivative mixtures (compositions) include a mixture of monomers and dimers of the water-soluble vitamin E derivatives (see, e.g., U.S. patent application Ser. No. 14/207,310, and International Application No. PCT/US2014/25006, now published U.S.

Patent Publication No. US-2014-0271593-A1, and published International Publication No. WO 2014/151109, respectively). Thus, this includes the high dimer PEG-derivatives of vitamin E, and includes TPGS compositions, as described and exemplified herein and provided and described in detail in U.S. Publication No. US-2014-0271593, and published International PCT Publication No. WO 2014/151109. This high dimer PEG-derivative of vitamin E compositions can be used in any of the compositions and powders provided herein as well as in the emulsion compositions described in U.S. Pat. Nos. 8,252,323, 7,906,140 and 8,414,914, which describe MAPT compositions, including MAPT compositions that contain a surface active agent. The high dimer PEG-derivatives of vitamin E, particularly the TPGS high dimer mixture, can be used in those MAPT compositions as the surface active agent in accord with the description in U.S. Pat. Nos. 8,252,323, 7,906,140 and 8,414,914. Any composition described in these patents can be modified to include a high dimer PEG-derivative of vitamin E mixture, particularly a high dimer TPGS mixture, as the surface active agent in the compositions.

Water-soluble vitamin E derivatives can be formed by covalently attaching the vitamin E moiety, a hydrophobic moiety, to another moiety, such as a hydrophilic moiety, for example, a polyalkylene glycol moiety, e.g., a polyethylene glycol (PEG) moiety, via a linker. For example, the vitamin E derivative compositions can include, but are not limited to, polyalkylene glycol derivatives of tocopherol, e.g., polyethylene glycol (PEG) derivatives of tocopherol, and polyalkylene glycol derivatives of tocotrienol, e.g., polyethylene glycol (PEG) derivatives of tocotrienol, and any other derivatized water-soluble form of vitamin E, such as those described in U.S. Publication No. 2011/0184194. The water-soluble vitamin E derivatives include, for example, vitamin E TPGS (D-α-tocopheryl polyethylene glycol succinate), TPGS analogs, TPGS homologs and TPGS derivatives.

Polyethylene glycol derivatives of vitamin E, such as vitamin E TPGS (D-α-tocopheryl polyethylene glycol succinate), are known. Compositions of PEG derivatives of vitamin E, for example, TPGS compositions, typically contain a mixture of monomers and dimers, where a monomer is a single vitamin E molecule covalently joined to a water-soluble moiety, such as a polyethylene glycol, through a linker, where the water-soluble moiety, e.g., PEG, has a free, unreacted, terminal reactive group, e.g., a free terminal hydroxyl group. A dimer is made up of two vitamin E molecules covalently joined to a water-soluble moiety, such as a polyethylene glycol, through one or more linkers, where both ends of the water-soluble moiety, e.g., both terminal hydroxyl groups of a PEG moiety, have reacted with a linker that is joined to a vitamin E molecule so that there are no free terminal reactive groups, e.g., hydroxyl groups. For example, the monomer and dimer are formed during the esterification reaction between the acid moiety of vitamin E succinate and the terminal hydroxyl groups of a polyethylene glycol to produce TPGS. Known TPGS compositions contain primarily TPGS monomer, e.g., between 70 wt % and 87 wt %, or higher, TPGS monomer. The monomer has been considered the effective component and the dimer considered to be a byproduct, thus the amounts of dimer are minimal, e.g., less than 12 wt %.

Included among the water-soluble vitamin E derivative mixtures (compositions) employed in the compositions provided herein are those, referred to herein as high dimer mixtures, that are prepared so that they contain significantly more dimer, i.e., more than 12%, particularly at least 20%, 25%, 29%, or more, generally between about 29-55%, 35%-55%, or more such as up to 75%, 80%, 85%, 90% or 95% dimer, and contain some monomer, i.e., less than 70 wt % monomer. For example, described herein are TPGS compositions that contain less TPGS monomer, i.e., less than 70 wt % TPGS monomer, and more TPGS dimer, i.e., more than 12 wt % TPGS dimer, such as at least 20%, 25%, 29%, or more, up to 75%, 80%, 85%, 90% or 95% dimer.

The water-soluble vitamin E derivative mixtures (compositions) have advantageous properties compared to vitamin E derivative compositions that contain higher concentrations (i.e., greater than 70%) monomer. In particular, the vitamin E derivative compositions that contain more dimer form are more effective in solubilizing non-polar additives (non-polar compounds) than compositions that contain the monomer form and very little dimer form. In addition, the higher dimer-containing water-soluble vitamin E derivative mixtures (compositions) permit dissolution of higher concentrations of non-polar ingredients while retaining the clarity and stability of the resulting compositions. The compositions provided herein contain the water-soluble vitamin E derivative mixtures, particularly the TPGS mixtures, with concentrations of dimer that are greater than 12%, particularly at least 20%, 25%, 29% and higher, contain non-polar compounds.

1) Vitamin E

Vitamin E refers to a group of eight water-insoluble compounds that include tocopherols and tocotrienols. Both structures are similar, containing a chromal ring and a 16-carbon side chain. The 16-carbon side chain of the tocopherols is saturated, while the side chain of the tocotrienols is unsaturated, with double bonds at the 3', 7' and 11' positions. Each tocopherol and tocotrienol exists in the α, β, γ and δ forms, differentiated by the number and position of methyl groups on the ring (labeled $R_1$, $R_2$ and $R_3$), as shown below.

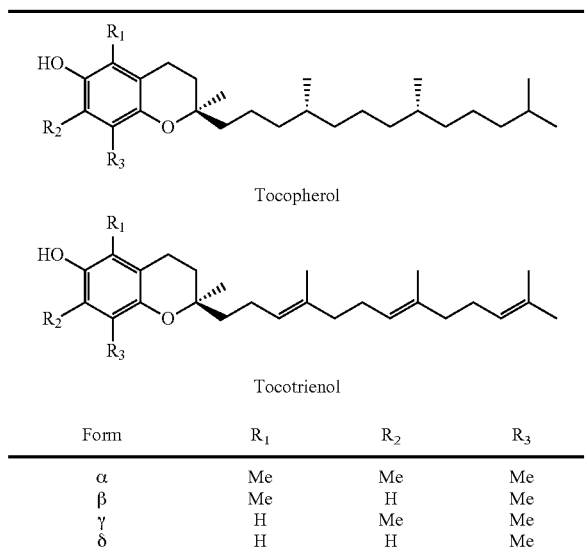

| Form | $R_1$ | $R_2$ | $R_3$ |
|---|---|---|---|
| α | Me | Me | Me |
| β | Me | H | Me |
| γ | H | Me | Me |
| δ | H | H | Me |

2) Polyalkylene Glycol Derivatives of Vitamin E

The water-soluble vitamin E derivatives (e.g., water-soluble tocopherols or water-soluble tocotrienols) can include polyalkylene glycol derivatives of vitamin E, such as polyethylene glycol (PEG) derivatives of vitamin E, for example, PEG derivatives of tocopherols or tocotrienols.

Suitable PEG derivatives of vitamin E can contain one or more tocopherol or tocotrienol, attached to one or more PEG moiety via a linker, for example, a dicarboxylic acid linker. Exemplary dicarboxylic acid linkers include succinic acid and succinic anhydride. An exemplary water-soluble vitamin E derivative is shown schematically below:

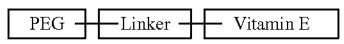

where the line between the PEG and the linker, and the line between the linker and the vitamin E moiety, each independently represent a covalent bond, for example, a covalent bond that forms an ester, ether, amide or thioester.

Typically, the vitamin E-PEG derivatives are made by covalently attaching the PEG moiety, such as by esterification, to a vitamin E-linker conjugate (e.g., a tocopherol-linker conjugate). The vitamin E-linker conjugate can be formed through esterification of the hydroxyl group of the vitamin E moiety with a carboxylic acid group of a linker, such as a dicarboxylic acid linker. In one example, the vitamin E-linker conjugate can be a tocopherol-linker conjugate, such as a tocopherol ester, for example, tocopherol succinate. The esterification reaction can be performed by any of a number of known methods, including those described in U.S. Pat. Nos. 2,680,749; 4,665,204; 3,538,119; and 6,632,443. The resulting vitamin E-linker conjugate can then be attached to a PEG moiety by another esterification reaction, for example, between a carboxylic acid group of the vitamin E-linker conjugate and a hydroxyl group of the PEG moiety, to form a vitamin E-PEG derivative.

PEG derivatives of a tocopherol-linker or tocotrienol-linker conjugate can be made by any other method known to those of skill in the art. Various methods known in the art for producing PEG derivatives can be used to attach a PEG molecule to tocopherol-linker or tocotrienol-linker compounds. For example, a tocopherol-linker conjugate can form a covalent bond to the PEG molecule via an amide, ether or thioether bond. For example, a tocopherol-linker conjugate that contains an amine group can be reacted with a PEG-NHS (N-hydroxysuccinimide) derivative to form an amide bond between the tocopherol-linker conjugate and the PEG molecule. A tocopherol-linker conjugate that contains an amine group can be reacted with a PEG-aldehyde derivative to form an amide bond between the tocopherol-linker conjugate and the PEG molecule. In another example, a tocopherol-linker conjugate that contains an carboxylic acid can be activated to the corresponding acid halide and reacted with a PEG-SH derivative to form a thioester bond between the tocopherol-linker conjugate and the PEG molecule.

a) Tocopherols and Tocotrienols

The tocopherols used to make the water-soluble vitamin E derivative mixtures described herein can be any natural or synthetic vitamin E tocopherol, including, but not limited to, alpha-tocopherols, beta-tocopherols, gamma-tocopherols and delta tocopherols, either in pure form or in a heterogeneous mixture of more than one form. Exemplary tocopherols are d-α-tocopherols and dl-α-tocopherols. To make the vitamin E-PEG derivative, the tocopherol typically is esterified with a linker, for example, a dicarboxylic acid, to form a tocopherol ester, which then is joined to a PEG moiety.

The tocotrienols used to make the water-soluble vitamin E derivative mixtures described herein can be any natural or synthetic vitamin E tocotrienol, including, but not limited to, alpha-tocotrienols, beta-tocotrienols, gamma-tocotrienols and delta tocotrienols, either in pure form or in a heterogeneous mixture of more than one form. Mixtures of tocopherols and tocotrienols are contemplated for use in the described methods and compositions. A tocotrienol can be esterified with a linker, such as a dicarboxylic acid, before joining with a PEG moiety to form a vitamin E-PEG derivative.

b) Linkers

Typically, the water-soluble vitamin E derivatives described herein include a vitamin E moiety, e.g., a tocopherol or tocotrienol, attached to a PEG moiety through a linker. The linker can be any linker that is capable of forming a covalent bond with both the vitamin E moiety and the PEG moiety. For example, the linker can be any linker capable of forming more than one covalent bond such as an ester bond, an amide bond, an ether bond, a thioether bond, or any combination thereof. In some embodiments, the linker is capable of forming more than one ester bond, for example, the linker can be a dicarboxylic acid or dicarboxylic acid derivative. Exemplary dicarboxylic acids and derivatives useful as linkers in the water-soluble vitamin E derivatives described herein include succinic acid, succinic anhydride, sebacic acid, dodecanedioic acid, suberic acid (i.e., octanedioic acid), azelaic acid, citraconic acid, methylcitraconic acid, itaconic acid, maleic acid, glutaric acid, glutaconic acid, fumaric acid and phthalic acid. Accordingly, exemplary of the vitamin E-linker conjugates (i.e., tocopherol or tocotrienol attached to a linker through an ester bond) that can be further esterified to form the vitamin E-PEG derivatives (i.e., water-soluble vitamin E derivatives) described herein are tocopheryl succinate, tocopheryl sebacate, tocopheryl dodecanodioate, tocopheryl suberate, tocopheryl azelaate, tocopheryl citraconate, tocopheryl methylcitraconate, tocopheryl itaconate, tocopheryl maleate, tocopheryl glutarate, tocopheryl glutaconate, tocopheryl fumarate, tocopheryl phthalate, tocotrienol succinate, tocotrienol sebacate, tocotrienol dodecanodioate, tocotrienol suberate, tocotrienol azelaate, tocotrienol citraconate, tocotrienol methylcitraconate, tocotrienol itaconate, tocotrienol maleate, tocotrienol glutarate, tocotrienol glutaconate, tocotrienol fumarate and tocotrienol phthalate.

In other embodiments, the linker can be any compound capable of forming more than one covalent bond, for example, a succinate ester, such as N-hydroxysuccinimide; an amino acid, such as glycine, alanine, 5-aminopentanoic acid or 8-aminooctanoic acid; or an amino alcohol, such as ethanolamine.

c) PEG Moieties

The polyalkylene moiety used to produce the water-soluble vitamin E derivatives described herein can be any polyalkylene moiety. Exemplary of a polyalkylene moiety is a polyethylene glycol (PEG) moiety. The PEG moiety used in the vitamin E derivatives described herein can be any of a plurality of known PEG moieties. Exemplary of suitable PEG moieties are PEG moieties having varying chain lengths and varying molecular weights, such as, for example, PEG 200, PEG 500, PEG 1000 and PEG 20,000, where the molecular weight of the PEG moiety is 200 Da, 500 Da, 1000 Da and 20,000 Da, respectively. Typically, the number following "PEG" indicates the molecular weight, in daltons (Da), of the PEG moiety. The PEG moiety of the water-soluble vitamin E derivatives described herein typically has a molecular weight of between or about between 200 Da to 20,000 Da, for example, between or about between 200 Da to 20,000 Da, 200 Da to 10,000 Da, 200 Da to 8000 Da, 200 Da to 6000 Da, 200 Da to 5000 Da, 200 Da to 3000 Da, 200 Da to 1000 Da, 200 Da to 800 Da, 200 Da to 600 Da, 200 Da to 400 Da, 400 Da to 20,000 Da, 400 Da to 10,000 Da, 400 Da to 8000 Da, 400 Da to 6000 Da, 400 Da to 5000 Da, 400 Da to 3000 Da, 400 Da to 1000 Da, 400 Da to 800 Da, 400 Da to 600 Da, 600 Da to 20,000 Da, 600 Da to 10,000 Da, 600 Da to 8000 Da, 600 Da to 6000 Da, 600 Da to 5000 Da, 600 Da to 3000 Da, 600 Da to 1000 Da, 600 Da to 800 Da, 8000 Da, 3000 Da to 6000 Da, 3000 Da to 5000 Da, 5000 Da to 20,000 Da, 5000 Da to 10,000 Da, 5000 Da to 8000 Da, 5000 Da to 6000 Da, 6000 Da to 20,000 Da, 6000 Da to 10,000 Da, 6000 Da to 8000 Da, 8000 Da to 20,000 Da, 8000 Da to 10,000 Da, or 10000 Da to 20,000 Da. For example, the PEG moiety of the water-soluble vitamin E derivatives described herein can have a molecular weight of 200, 300, 400, 500, 600, 800, 1000, 3000, 5000, 6000, 8000, 10,000, 20,000 Da or more.

Other known PEG analogs also can be used in the water-soluble vitamin E derivatives described herein. The PEG moieties can be selected from among any reactive PEG moiety, including, but not limited to, PEG-OH, PEG-NHS, PEG-aldehyde, PEG-SH, PEG-NH$_2$, PEG-CO$_2$H, and branched PEG moieties.

Exemplary of vitamin E derivatives that can be prepared for use herein are tocopheryl polyalkylene glycol derivatives, such as tocopheryl polyethylene glycol derivatives. These include tocopheryl polyethylene glycol succinate (TPGS), tocopheryl sebacate polyethylene glycol, tocopheryl dodecanodioate polyethylene glycol, tocopheryl suberate polyethylene glycol, tocopheryl azelaate polyethylene glycol, tocopheryl citraconate polyethylene glycol, tocopheryl methylcitraconate polyethylene glycol, tocopheryl itaconate polyethylene glycol, tocopheryl maleate polyethylene glycol, tocopheryl glutarate polyethylene glycol, tocopheryl glutaconate polyethylene glycol and tocopheryl phthalate polyethylene glycol, TPGS analogs and TPGS homologs. Exemplary of a water-soluble vitamin E derivative having a PEG moiety with a molecular weight of 1000 Da is TPGS 1000 (i.e., D-α-tocopheryl polyethylene glycol succinate 1000).

TPGS acts as a surfactant due to its hydrophilic polyethylene glycol (PEG) chain and its hydrophobic α-tocopherol portion. Surfactants aggregate and form micelles in aqueous mediums such that the hydrophilic portion(s) of the surfactant molecules are oriented toward the outside of the micelle, in contact with the aqueous medium, while the hydrophobic portion(s) of the surfactant molecules are oriented toward the center of the micelle.

3) Synthesis

Scheme 1 shows the synthesis of an exemplary water-soluble vitamin E derivative, TPGS, but any vitamin E moiety, i.e., any tocopherol or tocotrienol, can be used as the starting material and reacted with any linker, such as those described herein, that is capable of reacting with a polyalkylene glycol moiety to form a monomer form and dimer form of a water-soluble vitamin E derivative.

As shown in Scheme 1 below, TPGS can be prepared by reacting vitamin E with succinic anhydride or succinic acid to obtain vitamin E succinate, i.e., D-α-tocopheryl succinate, followed by esterification with a polyethylene glycol molecule, to obtain TPGS (see U.S. Pat. No. 2,680,749). TPGS analogs varying in PEG chain length (e.g., TPGS 200, 238, 400, 600, 2000, 3400, 3500, 4000 and 6000) have been synthesized, but the most widely used form of TPGS is TPGS 1000, which incorporates PEG 1000, a polyethylene glycol molecule with a molecular weight of approximately 1,000 Daltons (Collnot et al. (2006) J. Controlled Release 111:35-40). TPGS 1000 is a pale yellow, waxy solid substance that is amphipathic and hydrophilic, with a molecular weight of approximately 1,513 Daltons.

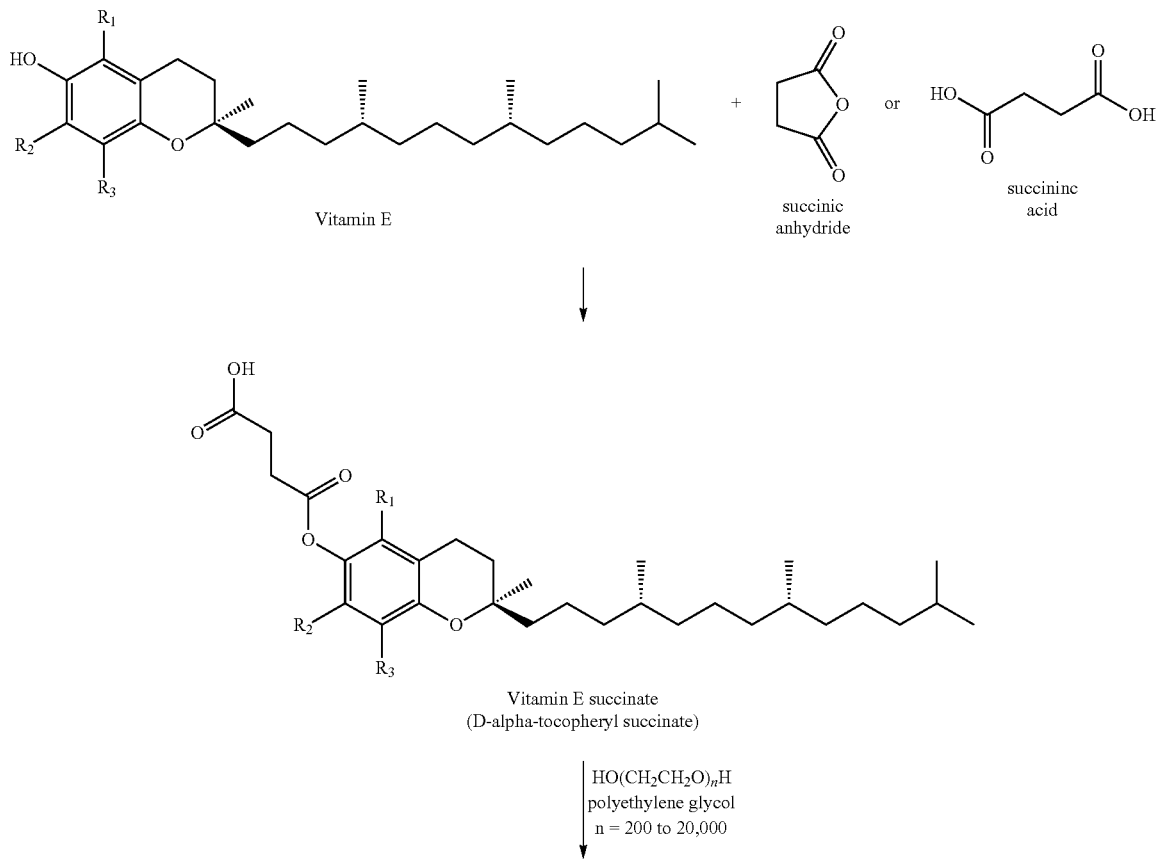

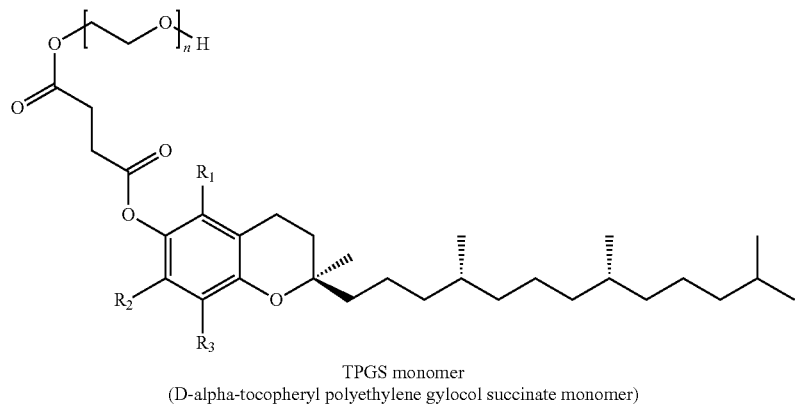

TPGS monomer
(D-alpha-tocopheryl polyethylene gylocol succinate monomer)

+

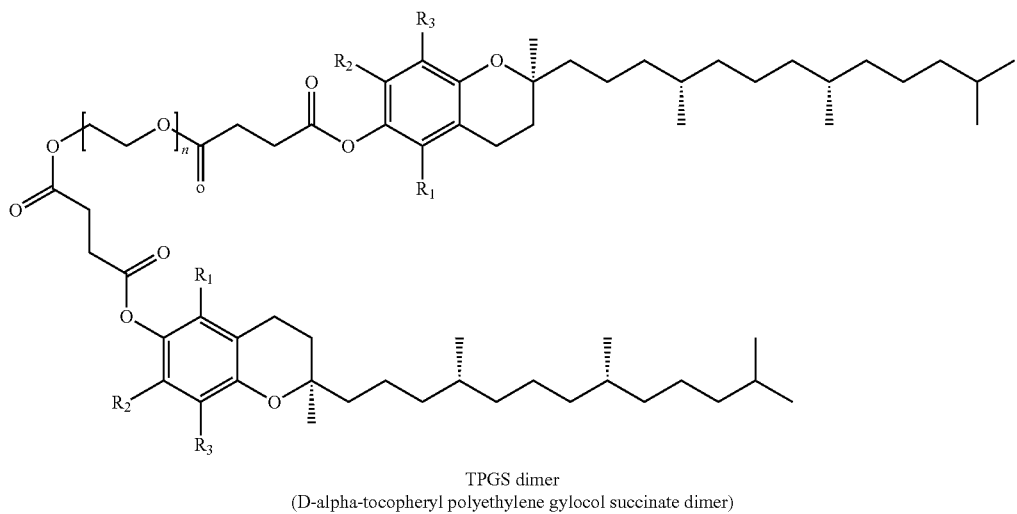

TPGS dimer
(D-alpha-tocopheryl polyethylene gylocol succinate dimer)

TPGS compositions, as generally prepared, such as commercially available TPGS 1000, are mixtures that contain primarily TPGS monomer (between 70% and 87% or more) and a lesser amount of TPGS dimer (less than 12%). The monomer is considered the effective component in TPGS, while the dimer is viewed as a byproduct of the esterification reaction between polyethylene glycol and vitamin E succinate. For example, commercially available TPGS, such as the TPGS 1000 available from Eastman Chemical Company (Kingsport, Tenn.), contains primarily TPGS monomer (~86% or more) and a small amount of TPGS dimer (~11% or less) (Christiansen et al. (2011) J. Pharm. Sci. 100(5): 1773-1782). TPGS synthesized according to standard methods, for example, the method described in U.S. Pat. No. 2,680,749, results in a TPGS composition that is composed primarily of TPGS monomer (70-87%) and a small amount of TPGS dimer (<12%) (US Pharmacopeia 23 (1998) Supp. 9:4712; Scientific Panel of the European Food Safety Authority (2007) EFSA J. 490:1-20). Because the separation of TPGS monomer and TPGS dimer is difficult and because TPGS monomer is considered the effective component of TPGS, TPGS compositions containing primarily TPGS dimer have not been developed (Kong et al. (2011) J. Chromatography A 1218:8664-8671). TPGS dimer, shown below, is usually considered an unwanted byproduct of the esterification reaction between PEG and vitamin E succinate, formed due to the equal reactivity of both terminal hydroxyl groups of the PEG moiety.

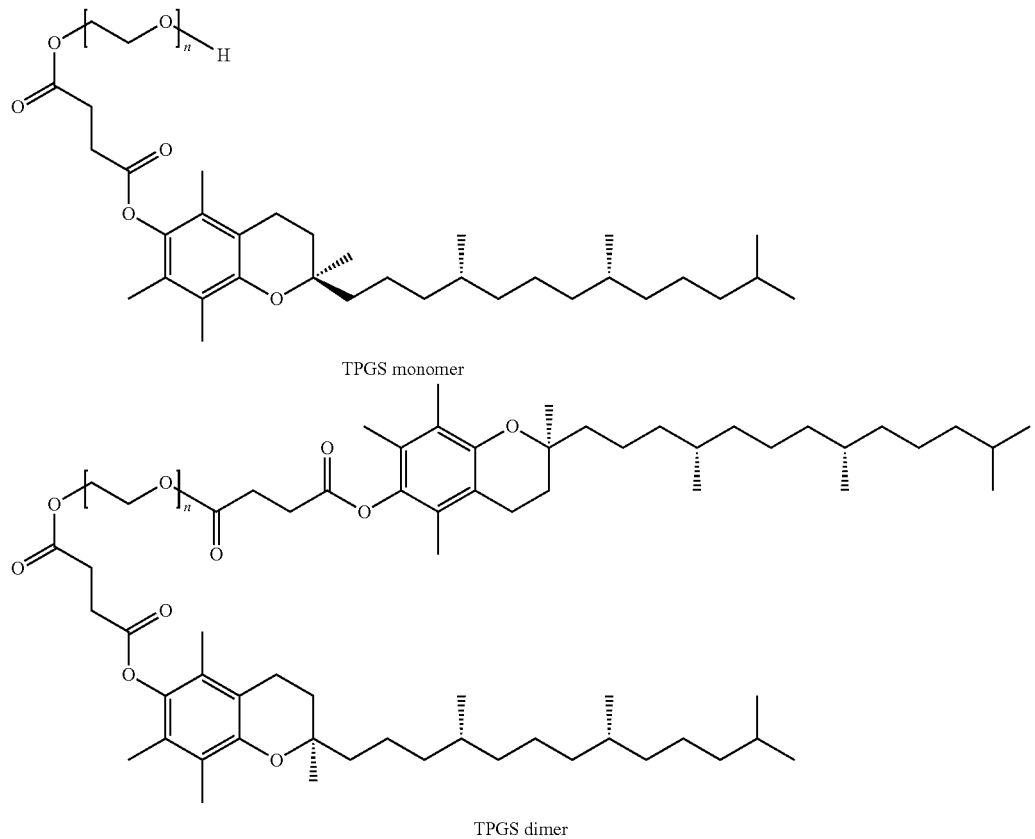

TPGS monomer

TPGS dimer

Methods for preparing these high dimer PEG-derivatives of vitamin E, including the high dimer TPGS compositions are described in detail in the U.S. Publication No. US-2014-0271593, and published International PCT Publication No. WO 2014/151109, and exemplified in the Example 12 below.

e. Agents for Delivery

These compounds have biological activity, such as a therapeutic or nutritional supplement. The compositions provided herein can contain one or more agents for delivery to a subject. Generally the agents are those that confer a biological effect. Any agent that can be formulated as described herein can be administered in the compositions provided herein. Where the agent is a therapeutic, the compositions contain a therapeutically effective amount of an agent to be delivered. As described herein, the compositions advantageously permit formulation of agents that are sensitive to water or degrade in water. These include sulfur containing agents, such as glutathione, and probiotics that are difficult to stably formulate.

The particular amount of active agent in a dosage will vary according to the nature of the active agent, the nature of the condition being treated, the age and size of the subject, and other parameters. As a supplement, the amount is an accepted amount for supplementation of the diet.

In particular embodiments, the agents are water sensitive agents that degrade when exposed to water, and, that generally are provided as powders. The instant MAPT compositions provide liquid compositions that are free of water, but contain such agents, which include, for example, glutathione, probiotics, peptides, such as growth hormone releasing hexapeptide (GHRP-6) and calcitonin, and probiotics.

Glutathione is among the agents for delivery, alone or in combination with other agents. Glutathione is an important detoxifying agent in the body. It is a powerful anti-oxidant administered as a supplement to help prevent or slow aging, protect against cancer cells and heavy metal toxicity.

The water-free MAPT compositions provided herein can include probiotics as the agent. Lactoferrin helps reduce degradation of probiotics in the compositions. The probiotic and lactoferrin are processed in the oil phase. Probiotics include bacterial strains that improve health or digestion, such as by colonizing the digestive tract to improve digestive flora. Such probiotics are well known and include, for example, those sold under the trademark FloraFIT® probiotics by Dupont™Danisco®, and include strains of genera of *Bifidobacteria* and *Lactobacillus*. Any such probiotic or mixture thereof, known to the skilled artisan, can be included in the water-free emulsion formulations and powders provided herein.

Generally, the amount of active agent in the composition will vary from less than about 0.01% by weight to about 20% by weight of the composition, or more, such as 1-10%, 3-10% and 5-10%. The compositions can be formulated for single dosage administration. A single dosage can vary from about 0.01 μg to 10 mg of an agent per kilogram of body weight of the host, with dosages from about 0.1 μg to 1 mg/kg being commonly employed. These concentrations, however, are general guidelines only and particular amounts and dosages may be selected based on the active agent being administered, the condition being treated, and the treatment regimen being employed. The concentration can be an amount of a drug or an active agent that is sufficient to provide the desired local or systemic effect and performance at a reasonable benefit/risk ratio to a subject attending any medical treatment. The dosage amount of glutathione, for example, is typically 1%-45% or 1%-20%, by weight in the composition, such as least 1, 2, 3, 4, 5, 6, 7, 8, 9, 10, 11, 12, 15, or 20%.

The level of agent to be delivered is from about 0.01% up to about 50%, from about 0.1% up to about 40%, from about 0.1% up to about 30%, from about 0.1% up to about 20%, from about 0.1% up to about 10%, from about 0.1% up to about 9%, from about 0.1% up to about 8%, from about 0.1% up to about 7%, from about 0.1% up to about 6%, from about 0.1% up to about 5%, from about 0.1% up to about 4%, from about 0.1% up to about 3%, from about 0.1% up to about 2%, or from about 0.1% up to about 1% by weight of the composition.

The compositions can contain other agents, such as other supplements and therapeutics. The agent to be delivered can be water soluble, slightly water soluble, or oil soluble. In certain embodiments, the additional agent to be delivered is selected from anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, non denatured whey protein, ophthalmics, psychic energizers, sedatives, steroids, sympathomimetics, parasympathomimetics, tranquilizers, urinary tract drugs, vaccines, vaginal drugs, vitamins, minerals, nonsteroidal anti-inflammatory drugs, angiotensin converting enzymes, polynucleotides, polypeptides, polysaccharides, and nutritional supplements including herbal supplements. See, U.S. Pat. Nos. 8,252,323, 7,906,140 and 8,414,914, which describe agents for inclusion in such compositions.

f. Polymers

The compositions optionally contain one or more polymers that modify the viscosity of the composition. The polymer used can coat the liposome/micelle/proteins to keep the solution from degrading until it reaches the site of absorption, such as the mucosal lining. In certain embodiments, the polymers for use herein are selected from homopolymers such as polyolefins including polyethylene, polypropylene, polybutene, and polymers of higher alpha-olefins; styrenic polymers including polystyrene, polymers made from styrene monomers with pendant alkyl groups such as poly(alpha-methylstyrene) and poly(para-methyl styrene), and halogenated versions of the above styrenic polymers; polydienes including polybutadiene, polyisoprene, and other polymers made from alkylated diene monomers; polyamides; polyimides; polycarbonates; polyisobutylene; acrylics such as poly(methyl methacrylate), poly(butyl methacrylate), poly(acrylic acid); silicones such as poly(dimethyl siloxane); polysulfones; vinyl polymers such as poly(vinyl chloride), poly(vinyl fluoride), poly(vinyl alcohol), poly(vinyl phenol), poly(vinylidene chloride), poly(vinylidene flouride), poly(tetrafluoro ethylene), poly(acrylonitrile); polyesters including poly(ethylene glycol) esters, poly(ethylene terephthalate), poly(butylene terephthalate; polyethers including poly(ethylene oxide), poly(propylene-oxide), poly(oxymethylene; poly(phenylene oxide); poly (phenylene sulfide); poly(acrylates); poly(benzimidazoles; and other polymers made from polymerizable monomers; statistical copolymers of the monomers or repeat units described above including for example copolymers of ethylene with other monomers such as alpha-olefins including propylene, butene-1, hexene, octene; dienes; vinyl acetate; vinyl alcohol; vinyl chloride; vinylidene chloride; copolymers of isobutylene with other monomers including isoprene, butadiene, para methylstyrene, styrene; copolymers of styrene with other monomers including butadiene, isoprene, maleic anhydride, acrylonitrile, oxazoline; copolymers of butadiene with other monomers including acrylonitrile; copolymers of propylene with other monomers including ethylene, butene, hexane and dienes; block copolymers made from units of any of the above homopolymers or copolymers including styrene-diene block polymers such as styrene-isoprene-styrene triblock copolymer, styrene-butadiene-styrene triblock copolymers, styrene-ethylene/propylene-styrene triblock copolymers (all ratios of ethylene to propylene); graft copolymers made from units of any of the above homopolymers or copolymers including poly(ethylene-graft-propylene), poly(styrene-graft-butadiene); and derivatized versions of any of the above homopolymers or copolymers including for example those made by sulfonation, amination, and carboxylation, such as sulfonated polystyrene, sulfonated ethylene-propylene-diene monomer.

As used herein, "polymer" also includes combinations or mixtures of more than one polymer wherein such combination or mixture exists in single or multiphase blends.

Generally the identity and composition (i.e., the ratio or amount of each type of copolymer unit desired) of the copolymer can be varied depending on the characteristics desired in the end product. It is within the skill of one ordinarily skilled in the art to make such selections.

In certain embodiments, the polymer for use herein is polyethylene glycol ester. In certain embodiments, the polyethylene glycol ester is selected from PEG 200 monolaurate, PEG 200 dilaurate, PEG 300 monolaurate, PEG 300 dilaurate, PEG 400 monolaurate, PEG 600 dilaurate, PEG 600 monolaurate, PEG 200 dilaurate, PEG 1000 monolaurate, PEG 1000 dilaurate, PEG 1540 monolaurate, PEG 1540 dilaurate, PEG 4000 monolaurate, PEG 4000 dilaurate, PEG 6000 monolaurate, PEG 6000 dilaurate, PEG 200 monostearate, PEG 200 distearate, PEG 300 monostearate, PEG 300 distearate, PEG 400 monostearate, PEG 600 distearate, PEG 600 monostearate, PEG 200 distearate, PEG 1000 monostearate, PEG 1000 distearate, PEG 1540 monostearate, PEG 1540 distearate, PEG 4000 monostearate, PEG 4000 distearate, PEG 6000 monostearate, PEG 6000 distearate, PEG 200 monooleate, PEG 200 dioleate, PEG 300 monooleate, PEG 300 dioleate, PEG 400 monooleate, PEG 600 dioleate, PEG 600 monooleate, PEG 200 dioleate, PEG 1000 monooleate, PEG 1000 dioleate, PEG 1540 monooleate, PEG 1540 dioleate, PEG 4000 monooleate, PEG 4000 dioleate, PEG 6000 monooleate and PEG 6000 dioleate.

In certain embodiments, the polymer used herein is PEG 400 distearate. In certain embodiments, PEG 400 distearate is present at a concentration of about 0.1% by weight up to about 10% by weight of the total weight of the composition. In other embodiments, PEG 400 distearate is present at a concentration of about 0.1% by weight up to about 8% by weight of the total weight of the composition. In other embodiments, PEG 400 distearate is present at a concentration of about 0.1% by weight up to about 6% by weight of the total weight of the composition. In other embodiments, PEG 400 distearate is present at a concentration of about 0.1% by weight up to about 4% by weight of the total weight of the composition. In other embodiments, PEG 400 distearate is present at a concentration of about 0.1% by weight up to about 2% by weight of the total weight of the composition. In other embodiments, PEG 400 distearate is present at a concentration of about 2% by weight of the total weight of the composition. In other embodiments, PEG 400 distearate is present at a concentration of about 1.8% by weight of the total weight of the composition. In other embodiments, PEG 400 distearate is present at a concentration of about 1.5% by weight of the total weight of the composition. In other embodiments, PEG 400 distearate is present at a concentration of about 1% by weight of the total weight of the composition. In other embodiments, PEG 400 distearate is present at a concentration of about 0.1% by weight of the total weight of the composition.

g. Cosolvent

The compositions provided herein can also contain one or more cosolvents. Such cosolvents are non-toxic, pharmaceutically acceptable substances, typically liquids, which do not substantially negatively affect the solubility of the active agents at the concentrations used. The cosolvent can aid in dissolving the active agent or for the mucoadhesive materials, or both. The cosolvent in certain embodiments, is a polyhydric alcohol or combination of polyhydric alcohols. In certain embodiments, the cosolvent is ethylene glycol, dipropylene glycol, propylene glycol, polyethylene glycol, glycerin, butylene glycol, hexylene glycol, polyoxyethylene, polypropylene glycol, sorbitol, ethylene glycol, or a mixture thereof. As discussed above, the cosolvent can be glycerin, but this is in addition to the glycerin employed as the polar protic solvent.

The amount of cosolvent in the compositions provided herein depends on the solubility of the active agent and/or the mucoadhesive substance in the oil or polar protic solvent, other than water, phase. Typically, the cosolvent is present in an amount sufficient to achieve complete dissolution of the active agent. In certain embodiments, the cosolvent is propylene glycol and is present at a concentration of about 1% by weight up to about 30% by weight of the total weight of the total composition. In other embodiments, propylene glycol is present at a concentration of about 1% by weight up to about 20% by weight of the total weight of the total composition. In other embodiments, propylene glycol is present at a concentration of about 1% by weight up to about 15% by weight of the total weight of the total composition. In other embodiments, propylene glycol is present at a concentration of about or at least 1% by weight up to about 10% by weight of the total weight of the total composition. In other embodiments, propylene glycol is present at a concentration of about 15% by weight of the total weight of the total composition. In other embodiments, propylene glycol is present at a concentration of about or at least 13% by weight of the total weight of the total composition. In other embodiments, propylene glycol is present at a concentration of about or at least 11% by weight of the total weight of the total composition. In other embodiments, propylene glycol is present at a concentration of about or at least 9.5% by weight of the total weight of the total composition. In other embodiments, propylene glycol is present at a concentration of about or at least 7.5% by weight of the total weight of the total composition. In other embodiments, propylene glycol is present at a concentration of about or at least 5% by weight of the total weight of the total composition. In other embodiments, propylene glycol is present at a concentration of about or at least 3% by weight of the total weight of the total composition. In other embodiments, propylene glycol is present at a concentration of about or at least 1% by weight of the total weight of the total composition.

h. Other Additives

The compositions provided herein can further contain one or more other additives such as taste modifying agents, a buffering agent, a chelating agent, a colorant, an osmotic modifier, a preservative, a sterilizer, a solubilizer, a tonicifier, a trace element, and a viscomodulator.

Taste modifying agents for use herein include, but are not limited to flavoring agents, sweetening agents and taste masking agents and are exemplified by: the essential oils or water soluble extracts of menthol, wintergreen, peppermint, sweet mint, spearmint, natural and artificial vanilla, cherry, chocolate, fudge, butterscotch, cinnamon, clove, lemon, orange, raspberry, rose, spice, violet, herbal, fruit, strawberry, grape, pineapple, peach, kiwi, papaya, mango, coconut, apple, coffee, plum, watermelon, nuts, durean, green tea, grapefruit, banana, butter, cream custard, camomile, sugar, dextrose, lactose, mannitol, sucrose, xylitol, maltitol, acesulfame potassium, talin, glycyrrhizin, sucralose, aspartame, saccharin, sodium saccharin, sodium cyclamate and honey. In certain embodiments, the taste modifying agent is selected from natural and artificial vanilla, cream custard, banana, fudge, butterscotch, coconut and chocolate. Many such agents are commercially available.

Buffering agents and pH adjusters include, but are not limited to acidulants and alkalizing agents exemplified by citric acid, fumaric acid, lactic acid, tartaric acid, malic acid, as well as sodium citrate, sodium bicarbonate and carbonate, sodium or potassium phosphate and magnesium oxide. Ph adjuster-1 to which the examples refer is triethanolamine or potassium bicarbonate, Ph adjuster-2 is soda ash or sodium bicarbonate. The particular pH at which the compositions are formulated depends upon the selected agent(s). For example, compositions containing glutathione typically are at about or at pH 2-4, such as at or about 3-3.5, including 3.2. Other composition provided herein, such as the compositions containing calcitonin, growth hormone releasing hexapeptide (GHRP-6) and the probiotics are at about or at pH 7 to 8, such as about or 7.8-8.

Coloring agents for use in the compositions include, but are not limited to FD & C coloring agents, natural coloring agents, and natural juice concentrates, pigments such as titanium oxide, silicon dioxide and zinc oxide.

Stabilizers as used in the compositions provided herein, include, but are not limited to anti-oxidants, chelating agents, and enzyme inhibitors as exemplified by ascorbic acid, vitamin E, butylated hydroxyanisole (BHA), butylated hydroxytoluene (BHT), propyl gallate, dilauryl thiodipropionate, thiodiproprionic acid, gum guaiac, citric acid, edetic acid and its salts and glutathione.

The compositions can contain preservatives which include, but are not limited sodium benzoate, potassium sorbate, parabens and derivatives, such as methyl paraben, propyl paraben, sorbic acid and its salts, propionic acids and its salts, sulfur dioxide and sulfites, acetic acid and acetates, and nitrites and nitrates.

i. Exemplary Compositions

Among the compositions provided herein, are compositions containing one or more agents formulated for mucosal delivery. The compositions provided are oil in polar protic solvent, other than water, or polar protic solvent, other than water, in oil emulsions. In certain embodiments, the oil phase in the compositions contains oat oil. The oil phase further contains one or more ingredients selected from the agent to be delivered, medium chain triglycerides preservatives and surfactants. The polar phase of the compositions contains a non-aqueous polar protic solvent, such a glycerin or and one or more ingredients selected from preservatives, surfactants, agent to be delivered and mucoadhesive proteins. In an exemplary embodiment, the mucoadhesive protein is albumin, immunoglobulin or a transferrin, such as lactoferrin; preservatives are selected from one among potassium sorbate, sodium benzoate, methyl paraben, propyl paraben and benzyl alcohol; the surfactants are phosphatidylcholine, polysorbate-80, and particularly TPGS, including the high dimer TPGS exemplified and described herein.

The compositions can contain oat oil from about 3% by weight up to about 25% by weight, generally about 3%, 4%, 7%, 7.5%, 8%, 15% or 25% by weight of the composition. The amount of MCT in the composition can be from about 10% by weight up to about 35% by weight, generally, 11%, 13%, 17%. 30% or 31% by weight of the composition. An exemplary composition can contain propylene glycol from about 8% by weight up to about 12% by weight, typically, 1%, 8%, 9%, 10% or 11% by weight of the composition. The mucoadhesive proteins are present, for example, from about 1% by weight up to about 11% by weight, typically 9%, 9.5% or 10% by weight of the composition.

Compositions among those provided herein that contain the high dimer TPGS, contain water and other agents.

j. Probiotic Compositions

Among compositions provided herein, are those that contain, in the polar phase, 50-65% polar protic solvent, such as glycerin, 1-5% PEG-derivative of vitamin E, such as TPGS, 1-5% mucoadhesive protein such as lactoferrin, and 5-15% probiotic. The oil phase also includes cosolvent, such as glycerine, in an amount between 1-5%, and additional PEG-derivative of vitamin E, such as TPGS, in an amount between about 1% and 10%, such as 5-8%. Thus, the compositions can contain a total of about or 50%-75% or 80% polar protic solvent, such as glycerin, 1%-20%, such as 5%-10% PEG-derivative of vitamin E, such as TPGS, 1%-10%, such as 3%-5% lactoferrin, and 5%-20%, such as 5%-15%, 8%-12%, or similar amount of probiotic. In all embodiments, the PEG-derivative of vitamin E, such as TPGS, can be a high dimer PEG-derivative of vitamin E as described and defined throughout the disclosure.

3. Compositions for Spray-Drying and Spray Dried Powders

The compositions provided herein can be spray dried to produce powders. Provided are methods for spray drying the compositions. Also provided are compositions for spray drying. In particular, the compositions contain a PEG-derivative of vitamin E, particularly TPGS, and in some embodiments the high dimer PEG-derivative of vitamin E mixture. By virtue of inclusion of the PEG-derivative of vitamin E, the compositions, which include components that can be sensitive to heat can be sprayed dried, because the TPGS interacts with the temperature sensitive component and protects such component(s) from degradation or denaturation by the temperatures required to evaporate the liquid, particularly water, from compositions. Hence provided are compositions containing a mucoadhesive protein, such as any listed herein, including transferrin, such as a lactoferrin, and the PEG-derivative of vitamin E, and particularly the high dimer mixtures. Optional ingredients include any of the other agents listed herein or of interest herein including in such composition, including the agents, such as glutathione. As a result, it is possible to provide spray-dried powders of any such composition.

Because the mucoadhesive proteins are thermally sensitive and can denature at 60° C., it is difficult to spray dry the compositions using a conventional heated spray dryer as these proteins precipitate and clog in the nozzle, and also denature the protein. Compositions containing mucoadhesive proteins, such lactoferrin, typically are freeze-dried as a spray dried powder in order to pasteurize and preserve its bioactivity functions. Provided herein is an alternative method, which allows the composition containing the mucoadhesive protein, such as lactoferrin, to be heated in a spray dryer without impairing its biological activity. The methods herein permit pasteurization of the compositions and spray drying at high temperature, while maintaining solubility and biological activity of the compositions and components, such as probiotics, of the compositions. By processing the probiotic and the mucoadhesive protein in the oil phase, the resulting emulsion is less susceptible to degradation and can be spray-dried without inactivating the probiotic component.

In accord with the methods, the lactoferrin is introduced into the oil phase of a pre-spray emulsion, such as any described herein. It is found herein, that the oil ingredients, such as Vitamin E TPGS (d-alpha tocopheryl polyethylene glycol succinate) encapsulate or interact with the temperature sensitive mucoadhesive protein, such as lactoferrin, and act to protect, such as, as a protective layer or medium, that withstands the heat during preparation of the emulsion phase and also during the spray drying process. As noted, this is advantageous for formulating products, such as probiotics.

For example, in an exemplary embodiment, mucoadhesive protein such as lactoferrin, is dissolved in the oil phase at or about 45° C. (40° C.-50° C.). For probiotic formulations, the probiotic is processed with the mucoadhesive protein, such as lactoferrin. The preparation of the emulsion of the oil and the polar protic solvent phase is performed at or about at 50° C. to 55° C. to produce the pre-spray emulsion. The pre-spray emulsion is cooled down to at or about 25° C.-35° C., such as to about or at 30° C. The pre-spray emulsion then is spray dried using a conventional heated spray dryer (i.e., a Model: CIT-LSD-H1500) at inlet temperature of 170° C. to 175° C. to produce a powder. In accord with such methods, no precipitate forms, so that the nozzle does not clog. In addition, the yield of product is high, typically greater than 80%, such as at least 85%.

MAPT compositions containing, such as those described herein, that contain glycerine, can be prepared with water as the polar solvent, if they also contain TPGS and then are spray dried soon after they made, before the water-sensitive component(s) degrade.

C. Methods of Manufacturing the MAPT Compositions

The compositions provided herein are stable emulsions of oil in polar protic solvent or polar protic solvent in oil, where the polar protic solvent typically is glycerine, and are prepared by dissolving the components of the composition in the oil and/or polar protic solvent, other than water, phases and mixing the two phases under constant temperature and pressure. They can be prepared by any suitable method for making emulsions. Exemplary procedures are set forth in the Examples.

1. Equipment Used in Exemplary Procedures Provided Herein Include:

a. Tanks

Two tanks, one for the oil phase and the other for a polar protic solvent, other than water, phase. The size of the tank can vary depending on the amount of oil and polar protic solvent required to prepare the emulsion.

b. Mixers

Mixers are used to blend, mix, emulsify and keep the material circulating in order to maintain temperature, viscosity, and other parameters to ensure the product meets the desired consistency. Mixers used in the procedures herein are: shears, inline mixers/mixing, Ribbon, Plow/Paddle Blenders, Forberg Mixers, Conveyors, Bag Dumps & Compactors, V-Blenders, Blade Mixers, Double Cone Mixers, Continuous Mixers, Speedflow Mixers, Batch Mixers, Double Ribbon Blenders, Paddle and Ribbon Mixers with Choppers, Plow Blenders/Turbulent Mixers, Fluidizing Forberg-Type Mixers, Air Mixers, Active Mixers, Passive Mixers, Top Entry Mixers, Side Entry Mixers, Static Mixers, Fixed Entry Mixers, Portable Mixers—both direct and gear drive, Sanitary Mixers, Drum Mixers, Bulk Container (IBC) Mixers, Lab Stirrers, Variable Speed Mixers, dough mixer, vertical mixer, spiral mixer, twin arm mixer, fork mixer, double spiral mixer, all agitators, and any other mixer applicable, agitator mixer, Banbury Mixer, Rubber Mixer, Blondheim Mixer, Churn Mixer, Conical Mixer, Continuous Mixer, Disperser Mixer, Pan Mixer, Emulsifier Mixer, Hobart Mixer, Liquifier Mixer, Littleford Mixer, Meat Mixer, Plow Mixer, Mixmuller Mixer, Nauta Mixer, Oakes Mixer, Planetary Mixer, Pony Mixer, PUG Mixer, Ribbon Mixer, Ross Mixer, Rotary Mixer, Sigma Mixer, Single Arm Mixer, Tote Bin Mixer, Tumble Mixer, Tumble Mixer, Vacuum Mixer, Turbolizer Mixer, Twin Shell Mixer, V-Type Mixer, Zig-Zag Mixer or side arm mixer.

c. Heating Apparatus

Heating apparatus are used to heat the oil, polar protic solvent and emulsion phases and for cleaning/sanitizing equipment before and after use. Exemplary heating apparatus that can be used in the procedures provided herein are: Electric/al jacketed tanks/kettles, water jacketed tanks/kettles, submersible heaters, semi-submersible heaters, immersible heaters, over-the-side heaters, straight hairpin heater tubes, steel sheath heaters, circular shaped heater tubes, incoloy sheath heaters, strip heaters, finned strip heaters, enclosure heaters, cartridge heaters, bolt heaters, component tubular heaters, finned tubular heaters, explosion resistant heaters, preweld heaters, bushing heaters, flanged heaters, bottom outlet heaters, circulation heaters, low temperature duct heaters and process heaters and other applicable heater apparatus.

Temperatures for heating solution and for cleaning/sanitizing range from 65° F. to about 220° F. During the dissolving and mixing steps, the temperature of the oil, polar protic solvent and emulsion phase is maintained at a level where the components of the composition retain their activity, for example the temperature is maintained such that the mucoadhesive protein does not denature during the process and the agent to be delivered does not degrade. A suitable temperature during the mixing step can be determined empirically for a particular combination of ingredients in the composition. Typically, the temperature is maintained at about 100-120° F., in some embodiments, at about 115° F. In certain embodiments, the temperature of the oil, polar protic solvent, and emulsion phase during the process is maintained at about 120° F. In other embodiments, the temperature of the oil, polar protic solvent and emulsion phase is maintained at about 100° F. In other embodiments, the temperature is maintained at about 60-70° F. In other embodiments, the temperature is maintained at about 50° F.

The pressure for water jackets is maintained at a level selected so that the components of the composition do not degrade. In certain embodiments, the pressure is maintained at a range from 1 PSI to 120 PSI (pounds per square inch). In certain embodiments, the pressure is 50 PSI. In other embodiments, the pressure is 30 PSI. In other embodiments, the pressure is 25 PSI. In other embodiments, the pressure is 10 PSI.

2. Exemplary Procedures for Preparing the Compositions

Exemplary procedures for preparing the compositions are described below:

a. Procedure A

Included among the compositions provided herein are oil in polar protic solvent, such as glycerin, emulsions where the agent to be delivered is soluble in either phase. Such compositions can be prepared by any suitable method known in the art, including the following procedure. The compositions are prepared at a temperature and pressure at which all the oil and water soluble components are soluble in the oil and polar protic solvent phases, respectively and the mucoadhesive protein and the agent to be delivered are not degraded in any way. For example, the temperature for heating the solution can be maintained at about 100°-150° F., in certain embodiments, 115° F., for all phases; and the pressure is at maintained about 20-30 pounds-per-square inch (PSI). In certain embodiments, when using this range and a water jacket, the pressure can be about 25 PSI.

1) Oil Phase

The oils used in the oil phase are weighed, added in a suitable vessel, such as a reactor tank and mixed to form a solution. The solution is heated and maintained at a temperature where all the oil soluble components can be dissolved in the oil phase while retaining their activity. A suitable temperature during the mixing step can be determined empirically for a particular combination of ingredients in the composition. Typically, the temperature is maintained at about 100-120° F., in some embodiments at about 115° F. A cosolvent, such as propylene glycol, is weighed and mixed with the oil solution at a speed where complete dissolution of the ingredients is achieved without denaturing or otherwise leading to degradation of any of the active ingredients. Generally, mixing is carried out at about 10 rpm, 50 rpm, 100 rpm, 150 rpm, 200 rpm, 250 rpm, 300 rpm or up to about 1000 rpm in oil phase. The oil preservatives, for example, methyl paraben and propyl paraben are weighed and added to the oil phase and the mixture is mixed to dissolve the preservatives. A sterile solution of benzyl hydroxide or benzyl benzoate is added and dissolved in the solution followed by addition of emulsifiers, lipids, phospholipids and polymers. If the agent to be delivered is soluble in the oil phase, it is added and mixed to dissolve. The temperature and pressure are maintained throughout the procedure to retain the activity of the agent to be delivered. In certain embodiments, the reactor vessel is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

2) Polar Protic Solvent Phase

The required amount of polar protic solvent, such as methanol, ethanol, glycerin and propylene glycol, generally glycerin, in the polar protic solvent phase is weighed and added in a suitable vessel, such as a reactor tank. The polar protic solvent phase is heated and maintained at a predetermined temperature such that the mucoadhesive protein and the active agent, when soluble in this phase, retain their activities. For example, in the compositions that contain lactoferrin, the temperature is maintained at or below 100° F. or about 115° F., but not lower than 65-68° F. in order prevent lactoferrin from denaturing. The temperature and pressure are monitored and maintained throughout the procedure. The preservatives, for example, Na Benzoate and K Sorbate are weighed and added to the water phase and the mixture is mixed to dissolve the preservatives. A predetermined amount of lipids, phospholipids and polymers to achieve a stable emulsion is added and dissolved. The temperature of this phase is maintained at a level that prevents denaturation of the mucoadhesive proteins. The mucoadhesive protein, required in an amount sufficient to achieve quantitative delivery of the agent to be delivered, is added to the polar protic solvent phase and mixed to dissolve. Where the agent to be delivered is water soluble, it is added and mixed to dissolve. The mixing is carried out at a speed where complete dissolution of the ingredients is achieved without denaturing or otherwise leading to degradation of the any active ingredients. Generally, mixing is carried out at about 10 rpm, 50 rpm, 100 rpm, 150 rpm, 200 rpm, 250 rpm, 300 rpm or up to about 1000 rpm in water phase. In certain embodiments, the reactor vessel, such as reactor tank, is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

3) Formation of Emulsion

The oil phase is added to the polar protic solvent phase. This can be achieved, for example, by pumping, manually adding or any other means of transferring from the oil tank to the water tank. As the oil phase is being added to the water phase, the mixture is mixed at a speed sufficient to create the emulsion without denaturing or otherwise leading to degradation of the any active ingredients. The mixing can be effected at about 100 rpm, 300 rpm, 500 rpm, 700 rpm, 1000 rpm, 10,000 rpm, 20,000 rpm, 30,000 rpm, 40,000 rpm, 50,000 rpm, 60,000 rpm or up to about 100,000 rpm. The mixing step can involve shearing or just light mixing to create the emulsion. In certain embodiments, mixing is achieved by shearing. In certain embodiments, the pH of the emulsion is a function of the mucoadhesive protein used. The emulsion is maintained at neutral or basic pH throughout these steps.

b. Procedure B

Included among the compositions provided herein are water-in-oil emulsions, where the agent for delivery is soluble in the oil phase. They can be prepared by any suitable method, including the following procedure and any modifications thereof. In all phases the temperature and pressure of the solution are maintained at a level sufficient to dissolve all the ingredients while retaining the activity of mucoadhesive protein and the agent to be delivered. The temperature generally is maintained at about 90° F. to 110° F., typically at about 100° F. or 115° F. A suitable temperature during the mixing step can be determined empirically for a particular combination of ingredients in the composition. Typically, the temperature is maintained at about 100-120° F., in some embodiments, at about 115° F. Pressure is adjusted to achieve the dissolution of the components while maintaining the activity of the mucoadhesive protein and the agent to be delivered. For the temperature range used in the procedures provided herein, the pressure (in pounds-per-square inch PSI) is in the range of about 20 to about 30 PSI, typically the pressure in the water jacket for heating the mixture is maintained at about 25 PSI. Generally the water phase is added to the oil phase to produce a composition for mucosal delivery.

1) Oil Phase

The oils used in the oil phase are weighed and mixed. The solution is heated up to and maintained at a temperature where all the oil soluble components can be dissolved in the oil phase while retaining their activity, typical temperature is 100° F. and the temperature is maintained throughout the procedure. In some embodiments, suitable temperature during the mixing step can be determined empirically for a particular combination of ingredients in the composition. Typically, the temperature is maintained at about 115° F. A cosolvent, such as propylene glycol is weighed and dissolved at a predetermined RPM whereby complete dissolution of ingredients is achieved without denaturing or otherwise leading to degradation of the any active ingredients. Required amount of oil preservatives, such as methyl paraben and propyl paraben are added to oil phase, followed by sterile solution of benzyl hydroxide or benzyl benzoate. Emulsifiers are added and mixed to the oil phase, followed by addition of required amounts of lipids, phospholipids and polymers. Any oil soluble active agent is then weighed and added to the oil phase. In certain embodiments, the reactor vessel is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

2) Polar Protic Solvent Phase

The required amount of polar protic solvent, such as glycerin, used in this phase is weighed and added in a reactor tank. It is heated and maintained at a temperature suitable for dissolution of the mucoadhesive protein and to prevent any degradation of the agent to be delivered. A cosolvent, if desired, such as propylene glycol, is weighed and dissolved. Preservatives, for example, Na Benzoate and K Sorbate can be weighed and added to the water phase and the mixture is mixed to dissolve the preservatives. Required amount of lipids, phospholipids and polymers to achieve stable emulsion are added and dissolved. For the compositions containing mucoadhesive proteins, such as lactoferrin, temperature is maintained at or below 100° F., in certain embodiments, 115° F., but not lower than room temperature in order prevent the protein from denaturing. Temperature and pressure are maintained throughout the procedure. The mucoadhesive protein, required in an amount sufficient to achieve quantitative delivery of the agent to be delivered, is added to the water phase and mixed to dissolve. An agent to be delivered, if soluble in the polar protic solvent phase, is added and mixed to dissolve. In certain embodiments, the reactor vessel, such as reactor tank, is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

3) Formation of Emulsion

The polar protic solvent phase is added to the oil phase. This can be achieved, for example, by pumping, manually adding or any other means of transferring from the oil tank to the water tank. As the phases are combined, the mixture is mixed at a speed sufficient to create the emulsion without denaturing or otherwise leading to degradation of the any active ingredients. The mixing can be effected at about 100 rpm, 300 rpm, 500 rpm, 700 rpm, 1000 rpm, 10,000 rpm, 20,000 rpm, 30,000 rpm, 40,000 rpm, 50,000 rpm, 60,000 rpm or up to about 100,000 rpm. In certain embodiments, mixing is achieved by shearing. The emulsion is maintained at a temperature lower than the denaturing temperature of proteins, typically at about 100° F. or about 115° F. The emulsion is maintained at neutral or basic pH during these steps.

c. Procedure C

This procedure can be used for either oil in polar protic solvent or polar protic solvent in oil emulsion where the agent to be delivered is soluble in the either phase. Such compositions can be prepared by any suitable method known in the art, including the following procedure. The compositions are prepared at a temperature and pressure at which all the oil and polar protic solvent soluble components are soluble in the oil and water phases, respectively, and the mucoadhesive protein and the agent to be delivered are not degraded in any way. For example, the temperature for heating the solution can be maintained at about 100-150° F. for all phases; and the pressure is at maintained about 20-30 pounds-per-square inch (PSI). For example, when using temperature in this range and a water jacket, the pressure can be about 25 PSI.

1) Oil Phase

Required amounts of all the oils used in this oil phase are weighed and mixed. The solution is heated and maintained at a temperature where all the oil soluble components can be dissolved in the oil phase while retaining their activity. In certain embodiments, the temperature is maintained at about 100° F.-150° F., typically at 100° F., or about 115° F. for all phases. A cosolvent, such as propylene glycol is weighed and dissolved at a predetermined RPM whereby complete dissolution of ingredients is achieved without denaturing or otherwise leading to degradation of the any active ingredients. Required amount of oil preservatives, such as methyl paraben and propyl paraben are added to oil phase, followed by sterile solution of benzyl hydroxide or benzyl benzoate. Emulsifiers are added and mixed in the oil phase, followed by addition of required amounts of lipids, phospholipids and polymers to achieve a stable emulsion. If the agent to be delivered is soluble in the oil phase, it is added and mixed to dissolve. The temperature and pressure are maintained throughout the procedure to retain the activity of the agent to be delivered. In certain embodiments, the reactor vessel, such as reactor tank, is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

2) Polar Protic Solvent Phase

The required amount of polar protic solvent, such as glycerin, is weighed and added in a reactor tank. It is heated and maintained at a predetermined temperature such that the mucoadhesive protein and the active agent, when soluble in this phase, retain their activities. For example, in the compositions that contain lactoferrin, the temperature is maintained at or below 100° F., or about 115° F. but not lower than 65-68° F. in order prevent lactoferrin from denaturing. The temperature and pressure are monitored and maintained throughout the procedure. A cosolvent, such as propylene glycol, can be added. It is weighed and dissolved at a predetermined RPM whereby complete dissolution of the ingredients is achieved without denaturing or otherwise leading to degradation of the any active ingredients. Preservatives, for example, Na Benzoate and K Sorbate are weighed and added to the water phase and the mixture is mixed to dissolve the preservatives. Required amount of lipids, phospholipids and polymers to achieve stable emulsion are added and dissolved. Temperature and pressure are maintained throughout the procedure. The mucoadhesive protein, required in an amount sufficient to achieve quantitative delivery of the agent to be delivered, is added to the water phase and mixed to dissolve. Where the agent to be delivered is water soluble, it is added and mixed to dissolve. In certain embodiments, the reactor vessel, reactor tank is closed to prevent evaporation of any of the ingredients or maintained at other conditions that minimize evaporation, such as contained in a beaker in small volume. When the combination of ingredients is such that evaporation is not a problem, the reaction vessel does not necessarily have to be sealed.

3) Formation of Emulsion

The polar phase is added to the oil phase or oil phase can be added to water phase. This can be achieved, for example, by pumping, manually adding or any other means of transferring from the oil tank to the water tank. As the two phases are being added, the mixture is mixed at a speed sufficient to create the emulsion without denaturing or otherwise leading to degradation of the any active ingredients. The mixing can be effected at about 100 rpm, 300 rpm, 500 rpm, 700 rpm, 1000 rpm, 10,000 rpm, 20,000 rpm, 30,000 rpm, 40,000 rpm, 50,000 rpm, 60,000 rpm or up to about 100,000 rpm. The mixing step can involve shearing or just light mixing to create the emulsion. In certain embodiments, mixing is achieved by shearing. The emulsion is maintained at a temperature lower than the denaturing temperature of proteins, typically at about 100° F. or about 115° F. The emulsion is maintained at a selected pH, typically neutral or basic pH (pH 8-9), but lower, such as 2-4, particularly 3-3.5 when the agent is glutathione, throughout these steps.

In particular, in the embodiments herein, micelles are formed by mixing surfactant, such as polysorbate 80, and particularly or a PEG-derivative of vitamin E, such as TPGS, particularly the high dimer form of TPGS described herein (see, U.S. Publication No. US-2014-0271593, and published International PCT Publication No. WO 2014/151109 and description herein) glycerin and lactoferrin. Phosphatidylcholine is solubilized in MCT (medium chain triglycerides) oil and encapsulated in TPGS to form a mixture that is added to the micelle glycerin phase, resulting in liposomes with the associated agent and lactoferrin.

The various parameters described in the general procedures described above for the preparation of the glycerin in oil and oil in glycerin emulsions represent exemplary embodiments and are not intended to limit the scope of the subject matter provided herein.

D. Formulations

The compositions provided herein contain one or more agents for administration to a subject via the mucosa. The agents can be anything to be administered and in any amount, including the agents described herein. Typically the compositions contain therapeutically effective amounts of one or more biologically active agents that alter a biological function, such as a body function at the cellular, tissue or organ level and/or alters cosmetic appearance of a subject. In certain embodiments, the compositions provided herein are intended for delivery of biologically active agents through oral or nasal mucosa, thereby allowing for the avoidance of the gastrointestinal tract and first pass liver metabolism and consequently allowing the biologically active agent to directly enter into circulation.

The compositions provided herein are useful in altering a biological function, such as a body function at the cellular, tissue or organ level and/or altering cosmetic appearance of a subject. In certain embodiments, the compositions provided herein are useful in the prevention, treatment, or amelioration of one or more of the symptoms of diseases or disorders that can be treated by any agent that can be delivered to a mucosal surface via the compositions provided herein. The diseases or disorders treatable by the compositions provided include, but are not limited to neural disorders, respiratory disorders, immune system disorders, muscular disorders, reproductive disorders, gastrointestinal disorders, pulmonary disorders, digestive disorders, metabolic disorders, cardiovascular disorders, renal disorders, proliferative disorders, cancerous diseases and inflammation.

The compositions provided herein contain one or more agents to be delivered or pharmaceutically acceptable derivatives thereof. The compositions can be formulated into stable emulsions for mucosal delivery. In certain embodiments, the compositions have been found to be stable for up to 6 months.

The compositions are formulated as emulsions for administration to the oral or nasal mucosal membranes. Typically the compositions described above are formulated using techniques and procedures well known in the art (see, e.g., Ansel (1985) *Introduction to Pharmaceutical Dosage Forms*, Fourth Edition, p. 126)), including the procedures described above.

Typically, in the compositions provided herein, one or more agents to be delivered or pharmaceutically acceptable derivatives thereof is (are) present in the concentration that is effective for delivery of an amount, upon administration, that alters a biological function, such as a body function at the cellular, tissue or organ level and/or alters cosmetic appearance of a subject. Such alteration of a biological function or cosmetic appearance includes, but is not limited to treatment of diseases or disorders including, but are not limited to, neural disorders, respiratory disorders, immune system disorders, muscular disorders, reproductive disorders, gastrointestinal disorders, pulmonary disorders, digestive disorders, metabolic disorders, cardiovascular disorders, renal disorders, proliferative disorders, cancerous diseases and inflammation.

The compositions typically contain an agent to be delivered in an amount sufficient to exert a therapeutically useful effect in the absence of undesirable side effects on the subject. It is understood that the number and degree of side effects depends upon the condition for which the compositions are administered. For example, certain toxic and undesirable side effects are tolerated when treating life-threatening illnesses, such as tumors, that would not be tolerated when treating disorders of lesser consequence.

The concentration of the agent to be delivered in the composition will depend on absorption, inactivation and excretion rates thereof, the dosage schedule, and amount administered as well as other factors known to those of skill in the art. Typically a therapeutically effective dosage should produce a serum concentration of active ingredient from about 0.1 ng/ml to about 50-100 μg/ml. The compositions typically should provide a dosage of from about 0.01 mg to about 100-2000 mg of the agent to be delivered, depending upon the agent selected and adjusted for body surface area and/or weight. Typically, a daily dosage of about between 0.05 mg/kg and 0.5 mg/kg, in certain embodiments 10 mg/kg should be sufficient. The dosage is a function of the agent delivered. In certain embodiments, single dosages per administration contain 1-2 milliliters of 1, 10, 100, 200, 250, 500, 650, 1000, 1500, or 2000-2500 mgs of total material delivered and is a function of the agent delivered. In certain embodiments, 1, 2, 3, 4, 5 or more servings of the composition can be administered per day depending upon the agent delivered and disease treated. It is understood that the amount to administer is a function of the agent to be delivered, the alteration of a biological function or cosmetic appearance desired, and possibly the side effects that will be tolerated. Dosages can be empirically determined using recognized models for each effect desired.

Typically, the compositions are provided for administration to humans and animals in unit or multiple dosage forms as oil-polar protic solvent, other than water, emulsions containing suitable quantities of one or more agents to be delivered or pharmaceutically acceptable derivative thereof. The unit-dose forms as used herein refers to physically discrete units suitable for human and animal subjects and packaged individually as is known in the art. Each unit-dose contains a predetermined quantity of the agent to be delivered sufficient to produce the desired effect, in association with the required additives in the composition. Unit-dose forms can be administered in fractions or multiples thereof. Examples of unit dosage include capsules filled with liquid compositions. A multiple-dose form is a plurality of identical unit-dosage forms packaged in a single container to be administered in segregated unit-dose form. Examples of multiple-dose forms include vials and bottles.

E. Methods of Use of the Compositions

Provided herein are methods of mucosal delivery of agents to subjects. The methods for mucosal delivery of an agent provided herein include providing a composition for mucosal delivery and contacting the composition with a mucosal surface of a subject, whereby the agent is delivered into the circulatory system of the subject. Contacting a mucosal surface, such as the oral, nasal or other mucosal surface, such as the mucosa of the digestive system, of a subject with a composition provided herein permits delivery of the composition and hence of any selected agent that can be formulated as an emulsion. Contacting can be effected by any suitable method. For example, methods provided herein include the steps of providing a pharmaceutical composition as described herein, including an agent for delivery and administering the composition to the mucosa of the subject, generally either orally, whereby the composition contacts oral mucosa, and also mucosa in the digestive track, intranasal inhalation or other method whereby the composition contacts mucosa in the subject.

In the methods provided herein, the compositions can contact, adhere and/or penetrate into the mucosal lining from about 1 minute up to about 24 hours or more, typically, at least about 1, 2, 3, 5, 10, 15, 20, 30, 60, or 120 minutes. In some embodiments, in the methods provided herein, the compositions can contact, adhere and/or penetrate into the mucosal lining for at least about 1, 2, 3, 4, 6, 8, 10, 12, 14, 16, 18, 20, 22 or up to 24 hours.

The compositions provided herein can be administered by methods known to those of skill in the art, including, but not limited to delivering the composition in oral cavity or nasal cavity. The composition can be sprayed into the oral cavity or nasal cavity, administered as soft capsule filled with the liquid composition or contacted to the mucosal surface in the oral and nasal cavity by any other means known in the art. When delivering with a soft capsule, the capsule can then be chewed by the subject to release the composition into the oral cavity. The intranasal composition is applied to the nasal mucosa via topical application (spray and/or drops) of a safe and effective amount of the composition. The frequency of administration of the composition may vary, depending upon personal or medical needs, but generally ranges from about once per day to about four times daily.

The compositions are designed for delivery to a mucosal membrane whereby the agent to be delivered gets absorbed into the mucosa and directly enters into circulation. The amount of agent that is absorbed through the mucosal lining can be assessed by methods known in the art and described herein. For example, the amount of agent absorbed can be assessed by measuring the amount of agent administered to the subject and comparing it to the amount thereof found in a blood sample. The blood sample can be obtained at different time intervals. The interval of time can be empirically determined based on such factors as the agent to be delivered and the mode of administration. The amount of agent to be delivered per dosage depends on the amount of agent absorbed through the mucosal lining and other factors such as age and physical condition of the subject.

F. Articles of Manufacture

The compositions provided herein can be packaged as articles of manufacture containing packaging material, a composition provided herein, and a label that indicates that the composition is for mucosal delivery. In instances where the active agent is useful for altering a body function or altering cosmetic appearance of the subject, the compositions can be packaged as articles of manufacture containing packaging material, a composition provided herein suitable for mucosal administration, and a label that indicates that the composition is used for altering a body function or altering cosmetic appearance of the subject. In certain embodiments, the compositions can be packaged as articles of manufacture containing packaging material, a composition provided herein suitable for mucosal administration, and a label that indicates that the composition is used for delivery of dietary supplements. In certain embodiments, the compositions can be packaged as articles of manufacture containing packaging material, a composition provided herein suitable for mucosal administration, and a label that indicates that the composition is used for delivering a therapeutic agent to a subject in need thereof.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, bottles, and any packaging material suitable for a selected formulation and intended mode of administration and treatment.

The following examples are exemplary only and are not intended to limit the scope of the subject matter claimed herein.

Example 1

Preparation of a Mucosal Adhesive Penetrating Technology (MAPT) Glutathione Formulation Appropriate quantities of the raw materials were weighed for the 1.049 Kg batch as shown below:

| Ingredient | mg/serving | %/serving | mg/batch |
| --- | --- | --- | --- |
| Neobee ® M-5, Capric and Caprylic Acid (Oil Phase) | 12.6100 | 2.5506 | 26455.8 |

-continued

| Ingredient | mg/serving | %/serving | mg/batch |
| --- | --- | --- | --- |
| Oleic Acid (Oil Phase) | 10.4050 | 2.1046 | 21829.7 |
| Vitamin E 5-67 (Oil Phase) | 8.7170 | 1.7631 | 18288.3 |
| Benzyl Alcohol (Oil Phase) | 5.1801 | 1.0478 | 10867.8 |
| LIPOID 100 S 100 (94% Phosphatidycholine (PC)) (Oil Phase) | 2.3740 | 0.4802 | 4980.7 |
| Vitamin E TPGS (Oil Phase) | 33.0000 | 6.6748 | 69234.0 |
| Glycerin (Oil Phase) | 21.5440 | 4.3576 | 45199.3 |
| Riboflavin (1.1 mg overage, need 1 mg) | 1.1000 | 0.2225 | 2307.8 |
| Molybdenum 0.5% (1 mg × .05 = 50 mcg, need 35 mcg so overage) | 1.0000 | 0.2023 | 2098.0 |
| Glycerin (Glycerin phase) | 308.0659 | 62.3111 | 646322.3 |
| Polysorbate-80 (Lipids) (Glycerin phase) | 13.6525 | 2.7614 | 28642.9 |
| Glutathione (Glycerin phase) | 55.0000 | 11.1246 | 115390.0 |
| Lactoferrin (94% minimum) (Glycerin phase) | 17.5000 | 3.5396 | 36715.0 |
| Stevia (rebaudioside-A) (Flavor) | 1.6715 | 0.3381 | 3506.8 |
| Clove oil | 1.0870 | 0.2199 | 2280.5 |
| Cinnamon Oil | 0.5370 | 0.1086 | 1126.6 |
| Orange Oil | 0.9555 | 0.1933 | 2004.6 |
| Vanilla (Wild) (DABK820) | 5.6000 | 1.1327 | 11748.8 |
| Totals | 500.000 | 100.0000 | 1048999.0 |

The oil phase was prepared by weighing the appropriate amounts of Capric and Caprylic Acid (sold as Neobee® M-5), Oleic Acid, Vitamin E 5-67 and Benzyl Alcohol, and mixing until all the ingredients dissolved without heating. Then, LIPOID 100 S 100 (94% Phosphatidycholine (PC)) was added to the mixture and the mixture was heated to 72-80° C. while mixing using a magnetic stirrer on a hot plate, until all components dissolved (approximately 2 hours) to form the first mixture. In a separate container, Vitamin E TPGS was heated to 60° C. and glycerin was added. Once all components were dissolved in the first mixture and the first mixture reaches a temperature of 60° C., the Vitamin E TPGS and glycerin mixture was added, and mixed until the components dissolved. Next, clove oil, cinnamon oil, orange oil and vanilla flavor were weighed and added, in that order, and mixed until homogenous. Then, the mixture was allowed to cool to room temperature or approximately 30° C.

The glycerin phase was prepared by weighing the appropriate amounts of Glycerin, Polysorbate-80, Glutathione, Molybdenum, Riboflavin, Stevia and lactoferrin and adding the components, in that order, into a container containing an Arde Barinco high speed shear homogenizer. Components were continually mixed at room temperature until lactoferrin was completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to about 30° C. for 1 hour and taken from the cooler and, in some instances, remixed thoroughly. Preparation of the emulsion was followed by addition of flavors/sweeteners, if needed, to make up the batch of 1.049 Kg. After the solution was homogeneous, the solution was poured into hoppers for packaging. The finished solution was tested for the amount of Glutathione in the solution.

Example 2

Preparation of MAPT Glutathione Formulation Adjusted to pH Between 3.2 and 3.8

Appropriate quantities of the raw materials were weighed for the 51.86 Kg batch as shown below:

| Ingredient | mg/serving | %/serving | mg/batch |
|---|---|---|---|
| Neobee ® M-5, Capric and Caprylic Acid (Oil Phase) | 12.6100 | 2.5506 | 1322789.0 |
| Oleic Acid (Oil Phase) | 10.4050 | 2.1046 | 1091484.5 |
| Vitamin E 5-67 (Oil Phase) | 8.7170 | 1.7631 | 914413.3 |
| Benzyl Alcohol (Oil Phase) | 5.1801 | 1.0478 | 543392.5 |
| LIPOID 100 S 100 (94% Phosphatidycholine (PC)) (Oil Phase) | 2.3740 | 0.4802 | 249032.6 |
| Vitamin E TPGS (Oil Phase) | 33.0000 | 6.6748 | 3461700.0 |
| Glycerin (Oil Phase) | 21.5440 | 4.3576 | 2259965.6 |
| Riboflavin (1.1 mg overage, need 1 mg) | 1.1000 | 0.2225 | 115390.0 |
| Molybdenum 0.5% (1 mg × .05 = 50 mcg, need 35 mcg so overage) | 1.0000 | 0.2023 | 104900.0 |
| pH Adjuster-1 (DI Systems and water purification) (Oil phase) | 1.0000 | 0.2023 | 104900.0 |
| Glycerin (Glycerin phase) | 306.1159 | 61.9167 | 32111557.9 |
| Polysorbate-80 (Lipids) (Glycerin phase) | 13.6525 | 2.7614 | 1432147.3 |
| Glutathione (Glycerin phase) | 55.0000 | 11.1246 | 5769500.0 |
| Lactoferrin (94% minimum) (Glycerin phase) | 17.5000 | 3.5396 | 1835750.0 |
| pH Adjuster-2 (DI Systems and water purification) | 0.9500 | 0.1922 | 99655.0 |
| Stevia (rebaudioside-A) (Flavor) | 1.6715 | 0.3381 | 175340.4 |
| Clove oil | 1.0870 | 0.2199 | 114026.3 |
| Cinnamon Oil | 0.5370 | 0.1086 | 56331.3 |
| Orange Oil | 0.9555 | 0.1933 | 100232.0 |
| Vanilla (Wild) (DABK820) | 5.6000 | 1.1327 | 587440.0 |
| Totals | 500.000 | 100.0000 | 51862507.6 |

The oil was prepared by weighing the appropriate amounts of Capric and Caprylic Acid (sold as Neobee® M-5), Oleic Acid, Benzyl Alcohol and Vitamin E 5-67, and mixing until all the ingredients dissolve without heating. Neobee® is a caprylic/capric triglyceride made using glycerol from vegetable oil sources and medium-chain fatty acids from coconut or palm kernel oil. Then, LIPOID 100 S 100, which is 94% Phosphatidycholine (PC), was added to the mixture and heated to 60° C. while mixing, until all components dissolved. Once the oil dissolved, Vitamin E TPGS, glycerin and pH adjuster to adjust the pH to 2-4, typically about 3, particularly 3.2 or 3.3. to 3.8, were added, and mixed until all components dissolved, the mixture was allowed to cool to 40° C., and clove oil, cinnamon oil, orange oil and vanilla flavor were added.

The glycerin phase was prepared by weighing appropriate quantities of Riboflavin and Molybdenum and mixing gently until dissolved without heat. Appropriate quantities of Glycerin and Polysorbate-80 (Lipids) were added and mixed together until dissolved. Next, Stevia and then Glutathione and pH adjuster were added and mixed until dissolved. Target pH was 3.3 to 3.8. Finally, Lactoferrin was added the ingredients were mixed to dissolve all the components at 40° C.

pH adjuster-1 is triethanolamine or potassium bicarbonate, and pH adjuster-2 is soda ash or sodium bicarbonate; they are added to the compositions so that pH is 3.2 or 3.3 to 3.8

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler 30° C. for 1 hour and taken from the cooler and remixed thoroughly. Preparation of the emulsion was followed by addition of flavors/sweeteners, if needed, to make up the batch of 51.86 Kg. After the solution was homogeneous, the solution was poured into hoppers for packaging. The finished solution was tested for the amount of Glutathione in the solution.

Example 3

Preparation of MAPT Calcitonin Formulation

Appropriate quantities of the raw materials were weighed for the 1.049 Kg batch as shown below:

| Ingredient | mg/serving | %/serving | mg/batch |
|---|---|---|---|
| Capric and Caprylic Acid (Neobee ® M-5; Oil Phase) | 12.6100 | 2.5506 | 26455.8 |
| Oleic Acid (Oil Phase) | 10.4050 | 2.1046 | 21829.7 |
| Vitamin E 5-67 (Oil Phase) | 8.7170 | 1.7631 | 18288.3 |
| Benzyl Alcohol (Oil Phase) | 5.1801 | 1.0478 | 10867.8 |
| LIPOID 100 S 100 (94% Phosphatidycholine (PC)) (Oil Phase) | 2.3740 | 0.4802 | 4980.7 |
| Vitamin E TPGS (Oil Phase) | 33.0000 | 6.6748 | 69234.0 |
| Glycerin (Oil Phase) | 38.6400 | 7.8155 | 81066.7 |
| Glycerin (Glycerin phase) | 308.0700 | 62.3119 | 646330.9 |
| Polysorbate-80 (Lipids) (Glycerin phase) | 13.6525 | 2.7614 | 28642.9 |
| Calcitonin (Glycerin phase) | 40.0000 | 8.0906 | 83920.0 |
| Lactoferrin (94% minimum) (Glycerin phase) | 17.5000 | 3.5396 | 36715.0 |
| Stevia (rebaudioside-A) (Flavor) | 1.6715 | 0.3381 | 3506.8 |
| Clove oil | 1.0870 | 0.2199 | 2280.5 |
| Cinnamon Oil | 0.5370 | 0.1086 | 1126.6 |
| Orange Oil | 0.9555 | 0.1933 | 2004.6 |
| Vanilla (Wild) (DABK820) | 5.6000 | 1.1327 | 11748.8 |
| Totals | 500.000 | 100.0000 | 1048999.0 |

The oil phase was prepared by weighing the appropriate amounts of Neobee® M-5 (Capric and Caprylic Acid), Oleic Acid, Vitamin E 5-67, Benzyl Alcohol and LIPOID 100 S 100 (94% Phosphatidycholine (PC)) and then mixing at 72-80° C. using a magnetic stirrer on a hot plate, until all components dissolved (approximately 2 hours) to form the first mixture. In a separate container, Vitamin E TPGS was heated to 60° C. and Glycerin was added. Once all components dissolved in the first mixture and the first mixture reached a temperature of 60° C., the Vitamin E TPGS and glycerin mixture was added and mixed until the components dissolved. Next, clove oil, cinnamon oil, orange oil and vanilla flavor were weighed and added, in that order, and mixed until homogenous. Then the mixture was allowed to cool to room temperature or approximately 30° C.

The glycerin phase was prepared by weighing the appropriate amounts of Glycerin, Polysorbate-80, Calcitonin, Stevia and lactoferrin and adding the components, in that order, into a container containing an Arde Barinco high speed shear homogenizer. Components were continually mixed at room temperature until lactoferrin was completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. Preparation of the emulsion was followed by addition of flavors/sweeteners, if needed, to make up the batch of 1.049 Kg. After the solution was homogeneous, the solution was poured into hoppers for packaging. The finished solution was tested for the amount of Calcitonin in the solution.

Example 4

Preparation of MAPT Probiotic (*Lactobacillus bifidus*) Formulation

Appropriate quantities of the raw materials were weighed for the 1.049 Kg batch as shown below:

| Ingredient | mg/serving | %/serving | mg/batch |
|---|---|---|---|
| Neobee® M-5, Capric and Caprylic Acid (Oil Phase) | 12.6100 | 2.5506 | 26455.8 |
| Oleic Acid (Oil Phase) | 10.4050 | 2.1046 | 21829.7 |
| Vitamin E 5-67 (Oil Phase) | 8.7170 | 1.7631 | 18288.3 |
| Benzyl Alcohol (Oil Phase) | 5.1801 | 1.0478 | 10867.8 |
| LIPOID 100 S 100 (94% Phosphatidycholine (PC)) (Oil Phase) | 2.3740 | 0.4802 | 4980.7 |
| Vitamin E TPGS (Oil Phase) | 33.0000 | 6.6748 | 69234.0 |
| Glycerin (Oil Phase) | 38.6400 | 7.8155 | 81066.7 |
| Glycerin (Glycerin phase) | 308.0700 | 62.3119 | 646330.9 |
| Polysorbate-80 (Lipids) (Glycerin phase) | 13.6525 | 2.7614 | 28642.9 |
| *Lactobacillus bifidus* (Glycerin phase) | 40.0000 | 8.0906 | 83920.0 |
| Lactoferrin (94% minimum) (Glycerin phase) | 17.5000 | 3.5396 | 36715.0 |
| Stevia (rebaudioside-A) (Flavor) | 1.6715 | 0.3381 | 3506.8 |
| Clove oil | 1.0870 | 0.2199 | 2280.5 |
| Cinnamon Oil | 0.5370 | 0.1086 | 1126.6 |
| Orange Oil | 0.9555 | 0.1933 | 2004.6 |
| Vanilla (Wild) (DABK820) | 5.6000 | 1.1327 | 11748.8 |
| Totals | 500.000 | 100.0000 | 1048999.0 |

The oil phase was prepared by weighing the appropriate amounts of Neobee® M-5 (Capric and Caprylic Acid), Oleic Acid, Vitamin E 5-67, Benzyl Alcohol and LIPOID 100 S 100 (94% Phosphatidycholine (PC)) and then mixing at 72-80° C. while mixing using a magnetic stirrer on a hot plate, until all components dissolved (approximately 2 hours) to form the first mixture. In a separate container, Vitamin E TPGS was heated to 60° C. and Glycerin was added. Once all components dissolved in the first mixture and the first mixture reached a temperature of 60° C., the Vitamin E TPGS and glycerin mixture was added, and mixed until the components dissolved. Next, clove oil, cinnamon oil, orange oil and vanilla flavor were weighed and added, in order, and mixed until homogenous. Then the mixture was allowed to cool to room temperature or approximately 30° C.

The glycerin phase was prepared by weighing the appropriate amounts of Glycerin, Polysorbate-80, *Lactobacillus bifidus*, Stevia and lactoferrin and adding the components, in that order, into a container containing an Arde Barinco high speed shear homogenizer. Components were continually mixed at room temperature until lactoferrin completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler 30° C. for 1 hour and taken from the cooler and remixed thoroughly. Preparation of the emulsion was followed by addition of flavors/sweeteners, if needed, to make up the batch of 1.049 Kg. After the solution was homogeneous, the solution was poured into hoppers for packaging. The finished solution was tested for the amount of *Lactobacillus bifidus* in the solution.

Example 5

Preparation of MAPT Probiotic (*Lactobacillus bulgaricus*) Formulation

Appropriate quantities of the raw materials were weighed for the 1.049 Kg batch as shown below:

| Ingredient | mg/serving | %/serving | mg/batch |
|---|---|---|---|
| Neobee® M-5, Capric and Caprylic Acid (Oil Phase) | 12.6100 | 2.5506 | 26455.8 |
| Oleic Acid (Oil Phase) | 10.4050 | 2.1046 | 21829.7 |
| Vitamin E 5-67 (Oil Phase) | 8.7170 | 1.7631 | 18288.3 |
| Benzyl Alcohol (Oil Phase) | 5.1801 | 1.0478 | 10867.8 |
| LIPOID 100 S 100 (94% Phosphatidycholine (PC)) (Oil Phase) | 2.3740 | 0.4802 | 4980.7 |
| Vitamin E TPGS (Oil Phase) | 33.0000 | 6.6748 | 69234.0 |
| Glycerin (Oil Phase) | 38.6400 | 7.8155 | 81066.7 |
| Glycerin (Glycerin phase) | 308.0700 | 62.3119 | 646330.9 |
| Polysorbate-80 (Lipids) (Glycerin phase) | 13.6525 | 2.7614 | 28642.9 |
| *Lactobacillus bulgaricus* (Glycerin phase) | 40.0000 | 8.0906 | 83920.0 |
| Lactoferrin (94% minimum) (Glycerin phase) | 17.5000 | 3.5396 | 36715.0 |
| Stevia (rebaudioside-A) (Flavor) | 1.6715 | 0.3381 | 3506.8 |
| Clove oil | 1.0870 | 0.2199 | 2280.5 |
| Cinnamon Oil | 0.5370 | 0.1086 | 1126.6 |
| Orange Oil | 0.9555 | 0.1933 | 2004.6 |
| Vanilla (Wild) (DABK820) | 5.6000 | 1.1327 | 11748.8 |
| Totals | 500.000 | 100.0000 | 1048999.0 |

The oil phase was prepared by weighing the appropriate amounts of Neobee® M-5 (Capric and Caprylic Acid), Oleic Acid, Vitamin E 5-67, Benzyl Alcohol and LIPOID 100 S 100 (94% Phosphatidycholine (PC)) and then mixing at 72-80° C. while mixing using a magnetic stirrer on a hot plate, until all components dissolved (approximately 2 hours) to form the first mixture. In a separate container, Vitamin E TPGS was heated to 60° C. and Glycerin was added. Once all components dissolved in the first mixture and the first mixture reached a temperature of 60° C., the Vitamin E TPGS and glycerin mixture was added, and mixed until the components dissolved. Next, clove oil, cinnamon oil, orange oil and vanilla flavor were weighed and added, in that order, and mixed until homogenous. Then the mixture was allowed to cool to room temperature or approximately 30° C.

The glycerin phase was prepared by weighing the appropriate amounts of Glycerin, Polysorbate-80, *Lactobacillus bulgaricus*, Stevia and lactoferrin and adding the components, in that order, into a container containing an Arde Barinco high speed shear homogenizer. Components were continually mixed at room temperature until lactoferrin completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. Preparation of the emulsion was followed by addition of flavors/sweeteners, if needed, to make up the batch of 1.049 Kg. After the solution was homogeneous, the solution was poured into hoppers for packaging. The finished solution was tested for the amount of *Lactobacillus bulgaricus* in the solution.

Example 6

Preparation of MAPT Probiotic (*Streptococcus thermophilus*) Formulation

Appropriate quantities of the raw materials were weighed for the 1.049 Kg batch as shown below:

| Ingredient | mg/serving | %/serving | mg/batch |
| --- | --- | --- | --- |
| Neobee ® M-5, Capric and Caprylic Acid (Oil Phase) | 12.6100 | 2.5506 | 26455.8 |
| Oleic Acid (Oil Phase) | 10.4050 | 2.1046 | 21829.7 |
| Vitamin E 5-67 (Oil Phase) | 8.7170 | 1.7631 | 18288.3 |
| Benzyl Alcohol (Oil Phase) | 5.1801 | 1.0478 | 10867.8 |
| LIPOID 100 S 100 (94% Phosphatidycholine (PC)) (Oil Phase) | 2.3740 | 0.4802 | 4980.7 |
| Vitamin E TPGS (Oil Phase) | 33.0000 | 6.6748 | 69234.0 |
| Glycerin (Oil Phase) | 38.6400 | 7.8155 | 81066.7 |
| Glycerin (Glycerin phase) | 308.0700 | 62.3119 | 646330.9 |
| Polysorbate-80 (Lipids) (Glycerin phase) | 13.6525 | 2.7614 | 28642.9 |
| *Streptococcus thermophilus* (Glycerin phase) | 40.0000 | 8.0906 | 83920.0 |
| Lactoferrin (94% minimum) (Glycerin phase) | 17.5000 | 3.5396 | 36715.0 |
| Stevia (rebaudioside-A) (Flavor) | 1.6715 | 0.3381 | 3506.8 |
| Clove oil | 1.0870 | 0.2199 | 2280.5 |
| Cinnamon Oil | 0.5370 | 0.1086 | 1126.6 |
| Orange Oil | 0.9555 | 0.1933 | 2004.6 |
| Vanilla (Wild) (DABK820) | 5.6000 | 1.1327 | 11748.8 |
| Totals | 500.000 | 100.0000 | 1048999.0 |

The oil phase was prepared by weighing the appropriate amounts of Neobee® M-5 (Capric and Caprylic Acid), Oleic Acid, Vitamin E 5-67, Benzyl Alcohol and LIPOID 100 S 100 (94% Phosphatidycholine (PC)) and then mixing at 72-80° C. while mixing using a magnetic stirrer on a hot plate, until all components dissolved (approximately 2 hours) to form the first mixture. In a separate container, Vitamin E TPGS was heated to 60° C. and Glycerin was added. Once all components dissolved in the first mixture and the first mixture reached a temperature of 60° C., the Vitamin E TPGS and glycerin mixture was added, and mixed until the components dissolved. Next, clove oil, cinnamon oil, orange oil and vanilla flavor were weighed and added, in that order, and mixed until homogenous. Then the mixture was allowed to cool to room temperature or approximately 30° C.

The glycerin phase was prepared by weighing the appropriate amounts of Glycerin, Polysorbate-80, *Streptococcus thermophilus*, Stevia and lactoferrin and adding the components, in that order, into a container containing an Arde Barinco high speed shear homogenizer. Components were continually mixed at room temperature until lactoferrin was completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. Preparation of the emulsion was followed by addition of flavors/sweeteners, if needed, to make up the batch of 1.049 Kg. After the solution was homogeneous, the solution was poured into hoppers for packaging. The finished solution was tested for the amount of *Streptococcus thermophilus* in the solution.

Example 7

Preparation of MAPT-Noopept (N-Phenylacetyl-L-Prolylglycine Ethyl Ester) Formulation Appropriate quantities of the raw materials were weighed for the 1.049 Kg batch as shown below:

| Ingredient | mg/serving | %/serving | mg/batch |
| --- | --- | --- | --- |
| Neobee ® M-5, Capric and Caprylic Acid (Oil Phase) | 12.6100 | 2.5506 | 26455.8 |
| Oleic Acid (Oil Phase) | 10.4050 | 2.1046 | 21829.7 |
| Vitamin E 5-67 (Oil Phase) | 8.7170 | 1.7631 | 18288.3 |
| Benzyl Alcohol (Oil Phase) | 5.1801 | 1.0478 | 10867.8 |
| LIPOID 100 S 100 (94% Phosphatidycholine (PC)) (Oil Phase) | 2.3740 | 0.4802 | 4980.7 |
| Vitamin E TPGS (Oil Phase) | 33.0000 | 6.6748 | 69234.0 |
| Glycerin (Oil Phase) | 38.6400 | 7.8155 | 81066.7 |
| Glycerin (Glycerin phase) | 308.0700 | 62.3119 | 646330.9 |
| Polysorbate-80 (Lipids) (Glycerin phase) | 13.6525 | 2.7614 | 28642.9 |
| Noopept (N-phenylacetyl-L-prolylglycine ethyl ester) (Glycerin phase) | 40.0000 | 8.0906 | 83920.0 |
| Lactoferrin (94% minimum) (Glycerin phase) | 17.5000 | 3.5396 | 36715.0 |
| Stevia (rebaudioside-A) (Flavor) | 1.6715 | 0.3381 | 3506.8 |
| Clove oil | 1.0870 | 0.2199 | 2280.5 |
| Cinnamon Oil | 0.5370 | 0.1086 | 1126.6 |
| Orange Oil | 0.9555 | 0.1933 | 2004.6 |
| Vanilla (Wild) (DABK820) | 5.6000 | 1.1327 | 11748.8 |
| Totals | 500.000 | 100.0000 | 1048999.0 |

The oil phase was prepared by weighing the appropriate amounts of Neobee® M-5 (Capric and Caprylic Acid, Oleic Acid), Vitamin E 5-67, Benzyl Alcohol and LIPOID 100 S 100 (94% Phosphatidycholine (PC)) and then mixing at 72-80° C. using a magnetic stirrer on a hot plate, until all components dissolved (approximately 2 hours) to form the first mixture. In a separate container, Vitamin E TPGS was heated to 60° C. and Glycerin was added. Once all components were dissolved in the first mixture and the first mixture reached a temperature of 60° C., the Vitamin E TPGS and glycerin mixture was added, and mixed until the components dissolved. Next, clove oil, cinnamon oil, orange oil and vanilla flavor were weighed and added, in that order, and mixed until homogenous. Then the mixture was allowed to cool to room temperature or approximately 30° C.

The glycerin phase was prepared by weighing the appropriate amounts of Glycerin, Polysorbate-80, Noopept (N-phenylacetyl-L-prolylglycine ethyl ester), Stevia and lactoferrin and adding the components, in that order, into a container containing an Arde Barinco high speed shear homogenizer. Components were continually mixed at room temperature until lactoferrin was completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. Preparation of the emulsion was followed by the addition of flavors/sweeteners, if needed, to make up the batch of 1.049 Kg. After the solution was homogeneous, the solution was poured into hoppers for packaging. The finished solution was tested for the amount of Noopept in the solution.

Example 8

Preparation of Dry Powder Containing Lactoferrin

Appropriate quantities of the raw materials were weighed for the 8 Kg batch as shown below:

| Ingredient | mg/serving | % before drying | mg/batch |
| --- | --- | --- | --- |
| Palmitic Acid (oil phase) | 52.00000 | 3.467 | 277333.333 |
| Vitamin E Tocopherol Succinate Diester and Lecithin Blend (25% Sunflower lecithin and 75% TPGS) (oil phase) | 20.00000 | 1.333 | 106666.667 |
| Vegetable Oil (Soy or Canola) (oil phase) | 80.30000 | 5.353 | 428266.667 |
| Distilled Water | 1292.00000 | 86.133 | 6890666.667 |
| SiO$_2$ | 12.50000 | 0.833 | 66666.667 |
| Magnesium Stearate | 12.50000 | 0.833 | 66666.667 |
| Sodium Bicarbonate | 84.79000 | 5.653 | 452213.333 |
| Sorbitol | 115.36000 | 7.691 | 615253.333 |
| Xylitol | 105.00000 | 7.000 | 560000.000 |
| Malitol | 105.30000 | 7.020 | 561600.000 |
| Sucrose Fatty Acid Ester (SFAE) | 35.00000 | 2.333 | 186666.667 |
| Maltodextrin (Clusterdextrin) | 111.37700 | 7.425 | 594010.667 |
| Caffeine 95% From Green Tea PE (78% Overage) | 212.00000 | 14.133 | 1130666.667 |
| GABA | 62.00000 | 4.133 | 330666.667 |
| Glycine | 62.00000 | 4.133 | 330666.667 |
| Glutamic Acid | 117.00000 | 7.800 | 624000.000 |
| Tryptophan | 32.00000 | 2.133 | 170666.667 |
| Choline | 32.00000 | 2.133 | 170666.667 |
| Vitamin B5 (Pantothenic Acid) (5 mg label claim for 100% DRI) | 6.70000 | 0.447 | 35733.333 |
| Calcium Chloride (24% Calcium) | 62.00000 | 4.133 | 330666.667 |
| Vitamin B12 (2.4 mcg label claim for 100% DRI) | 0.00333 | 0.000 | 17.776 |
| L-Theanine | 26.00000 | 1.733 | 138666.667 |
| Vitamin C | 26.00000 | 1.733 | 138666.667 |
| Tyrosine | 59.00000 | 3.933 | 314666.667 |
| Nat Vanilla (WILD) DABK820 | 2.17000 | 0.145 | 11573.333 |
| lactoferrin (oil phase) | 67.00000 | 4.467 | 357333.333 |
| Totals | 2792 | 100 | 8000000.00 |

The water phase was prepared by weighing appropriate quantities of water, SiO$_2$, Magnesium Sterate, Sodium Bicarbonate, Sorbitol, Xylitol, Malitol, SFAE, Clusterdextrin, Caffeine, GABA, Glycine, Glutamic Acid, Tryptophan, Choline, Vitamin B5, Calcium Chloride, Vitamin B12, L-theanine, Vitamin C, Tyrosine, and natural vanilla, and mixing the ingredients to dissolve all the components at 70° C.

The oil phase was prepared by weighing the appropriate amounts of Palmitic Acid, lecithin, lactoferrin and vegetable oil and mixing until all the ingredients dissolved. Once ingredients were dissolved, the mixture is added to the TPGS.

The emulsion was prepared by heating the water and oil phases to 160° F., and adding the water phase to the oil phase slowly while mixing. The emulsion was cooled to 95° F., followed by the addition of flavors/sweeteners and additional water, if needed, to make up the batch of 8 Kg.

The emulsion was spray dried as described in Example 9. The resulting powder was cooled to 35° C. and packaged into appropriate containers.

Example 9

Preparation of Dry Powder Containing Lactoferrin, Glutathione and MCT Oil with TPGS Appropriate quantities of the raw materials were weighed for the 88.15 g batch of Solid MCT oil as shown below in Table 1.

TABLE 1

Preparation of Solid MCT oil

| Ingredient | %/serving before evaporation | g/batch |
| --- | --- | --- |
| Vitamin E TPGS | 2.58 | 2.27 |
| MCT Oil | 97.42 | 85.88 |
| Total | 100 | 88.15 |

Appropriate quantities of the raw materials were weighed for the 500 g batch as shown below in Table 2.

TABLE 2

Preparation of Lactoferrin, Glutathione and MCT Oil Preparation

| Ingredient | %/serving before evaporation | g/batch | %/serving after evaporation |
| --- | --- | --- | --- |
| Water | 57.518 | 287.5904137 | 0 |
| KHCO$_3$ | 3.333 | 16.66611113 | 7.85 |
| Cluster Dextrin | 6.366 | 31.83227226 | 14.99 |
| SFAE | 4.250 | 21.24929169 | 10.00 |
| Saladizer ® emulsifier ® | 0.067 | 0.333322223 | 0.16 |
| Lactoferrin | 8.500 | 42.49858338 | 20.01 |
| Glutathione | 2.337 | 11.68 | 5.50 |
| Solid MCT Oil | 17.629 | 88.14706176 | 41.50 |
| Totals | 100 | 500 | 100 |

The water phase was prepared by weighing the appropriate amounts of water, Saladizer® Emulsifier®, Cluster Dextrin, SFAE and KHCO$_3$ and then mixing at a temperature not more than 55° C.

The solid MCT oil was prepared by weighing the appropriate amounts of TPGS and MCT oil and dissolving the TPGS in the MCT oil at 55° C.

The oil phase was prepared by weighing the appropriate amounts of MCT solid oil, glutathione and lactoferrin. Then, glutathione and lactoferrin were mixed into the solid MCT oil solution. The oil phase was then passed through a filter.

The emulsion was prepared by adding the oil phase to the water phase (where each are at approximately 55° C.), slowly while mixing at low to medium RPM using an Arde Barinco Mixer Type 74D (Serial No. L-1274) until the mixture is homogeneous, or approximately 5 minutes. The emulsion was allowed to cool in a cooler for 1 hour and taken from the cooler and remixed thoroughly.

The emulsions were then spray dried into dry powders. The dry powder was prepared using a standard spray dryer equipped with a rotary atomizer nozzle or a standard spray nozzle. Alternatively, a fluid bed dryer or box dryer can be used. The pre-spray emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature no more than 175° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry power in water at a 1:3 or 1:1 powder to water ratio (e.g., 30-50 g powder was dissolved in 100 g of water) and spray drying a second time. The powders were then sifted/filtered using a 60-80 micron mesh screen.

Some pre-spray emulsions required the addition of extra water (i.e., evaporation water) as a processing aid to make the emulsion thinner and able to pass through the dryer pump more easily. The extra water was added to the pre-spray emulsion at 35° C. and was evaporated during the spray dry process, along with the rest of the water in the pre-spray emulsion. The resulting powder was cooled to 35° C. and packaged into appropriate containers.

The glutathione prepared as a powder or in a MAPT composition, such as example 1, is virtually 100% stable. There is no sulfur taste or odor and testing reveals it does not degrade. In contrast, it is reported by the FDA that 20% of glutathione degrades in 7 days when stored in water, even at pH 3 to 6. When stored in water at pH 2 and 7, only approximately 65% remains after 7 days.

Example 10

Preparation of Dry Powder Containing Lactoferrin and MCT Oil with TPGS

Appropriate quantities of the raw materials were weighed for the 194 g batch of Solid MCT oil as shown below in Table 3.

TABLE 3

Preparation of Solid MCT oil

| Ingredient | %/serving before evaporation | g/batch |
|---|---|---|
| Vitamin E TPGS | 2.58 | 5.01 |
| MCT Oil | 97.42 | 188.99 |
| Total | 100 | 194 |

Appropriate quantities of the raw materials were weighed for the 1100 g batch as shown below in Table 4.

TABLE 4

Preparation of Lactoferrin and MCT Oil Preparation

| Ingredient | %/serving before evaporation | g/batch | %/serving after evaporation |
|---|---|---|---|
| Water | 57.516 | 632.68 | 0 |
| KHCO$_3$ | 3.333 | 36.66422 | 7.85 |
| Cluster Dextrin | 6.366 | 70.028665 | 14.99 |
| SFAE | 4.250 | 46.7469 | 10.00 |
| Saladizer® emulsifier® | 0.067 | 0.73 | 0.16 |
| Lactoferrin | 10.839 | 119.23 | 25.51 |
| Solid MCT Oil | 17.629 | 193.92 | 41.49 |
| Totals | 100 | 1100 | 100 |

The powder, thus, contains 1.07% TPGS and 40.42% MCT Oil.

The water phase was prepared by weighing the appropriate amounts of water, Saladizer® Emulsifier®, Cluster Dextrin, SFAE and KHCO$_3$ and then mixing at a temperature not more than 55° C.

The solid MCT oil was prepared by weighing the appropriate amounts of TPGS and MCT oil and dissolving the TPGS in the MCT oil at 55° C. The oil phase was prepared by weighing the appropriate amounts of MCT solid oil and lactoferrin. Then, lactoferrin was mixed into the solid MCT oil solution. The oil phase was then passed through a filter.

The emulsion was prepared by adding the oil phase to the water phase (where each are at approximately 55° C.), slowly while mixing at low to medium RPM using an Arde Barinco Mixer Type 74D (Serial No. L-1274) until the mixture is homogeneous, or approximately 5 minutes. The emulsion was allowed to cool in a cooler for 1 hour and taken from the cooler and remixed thoroughly. The resulting mixture included about 17.17% MCT oil and about 0.45% TPGS.

The emulsion was spray dried as described in Example 9. The resulting powder was cooled to 35° C. and packaged into appropriate containers.

Example 11

Preparation of MAPT-GHRP-6 Formulation

Appropriate quantities of the raw materials were weighed for the 1.049 Kg batch as shown below:

| Ingredient | mg/serving | %/serving | mg/batch |
|---|---|---|---|
| Neobee® M-5, Capric and Caprylic Acid (Oil Phase) | 12.6100 | 2.5506 | 26455.8 |
| Oleic Acid (Oil Phase) | 10.4050 | 2.1046 | 21829.7 |
| Vitamin E 5-67 (Oil Phase) | 8.7170 | 1.7631 | 18288.3 |
| Benzyl Alcohol (Oil Phase) | 5.1801 | 1.0478 | 10867.8 |
| LIPOID 100 S 100 (94% Phosphatidycholine (PC)) (Oil Phase) | 2.3740 | 0.4802 | 4980.7 |
| Vitamin E TPGS (Oil Phase) | 33.0000 | 6.6748 | 69234.0 |
| Glycerin (Oil Phase) | 21.5440 | 4.3576 | 45199.312 |
| Riboflavin (1.1 mg overage, need 1 mg) | 1.1000 | 0.2225 | 2307.8 |
| Molybdenum 0.5% (1 mg × .05 = 50 mcg, need 35 mcg so overage) | 1.0000 | 0.2023 | 2098 |

-continued

| Ingredient | mg/serving | %/serving | mg/batch |
|---|---|---|---|
| Glycerin (Glycerin phase) | 308.0659 | 62.3111 | 646330.9 |
| Polysorbate-80 (Lipids) (Glycerin phase) | 13.6525 | 2.7614 | 28642.9 |
| GHRP-6 (Glycerin phase) | 55.0000 | 11.1246 | 115390 |
| Lactoferrin (94% minimum) (Glycerin phase) | 17.5000 | 3.5396 | 36715.0 |
| Stevia (rebaudioside-A) (Flavor) | 1.6715 | 0.3381 | 3506.8 |
| Clove oil | 1.0870 | 0.2199 | 2280.5 |
| Cinnamon Oil | 0.5370 | 0.1086 | 1126.6 |
| Orange Oil | 0.9555 | 0.1933 | 2004.6 |
| Vanilla (Wild) (DABK820) | 5.6000 | 1.1327 | 11748.8 |
| Totals | 500.000 | 100.0000 | 1048998.95 |

The oil phase was prepared by weighing the appropriate amounts of Neobee® M-5 (Capric and Caprylic Acid), Oleic Acid, Vitamin E 5-67, Benzyl Alcohol and LIPOID 100 S 100 (94% Phosphatidycholine (PC)) and then mixing at 72-80° C. using a magnetic stirrer on a hot plate, until all components dissolved (approximately 2 hours) to form the first mixture. In a separate container, Vitamin E TPGS was heated to 60° C. and Glycerin was added. Once all components dissolved in the first mixture and the first mixture reached a temperature of 60° C., the Vitamin E TPGS and glycerin mixture was added, and mixed until the components dissolved. Next, clove oil, cinnamon oil, orange oil and vanilla flavor were weighed and added, in that order, and mixed until homogenous. Then the mixture was allowed to cool to room temperature or approximately 30° C.

The glycerin phase was prepared by weighing the appropriate amounts of Glycerin, Polysorbate-80, GHRP-6, Molybdenum, Riboflavin, Stevia and lactoferrin and adding the components, in that order, into a container containing an Arde Barinco high speed shear homogenizer. Components were continually mixed at room temperature until the lactoferrin completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler 30° C. for 1 hour and taken from the cooler and remixed thoroughly. Preparation of the emulsion was followed by addition of flavors/sweeteners, if needed, to make up the batch of 1.049 Kg. After the solution is homogeneous, the solution was poured into hoppers for packaging.

Example 12

Preparation of MAPT Glutathione Formulation in TPGS

| Ingredient | (g) per batch | mg/ serv. | Density inclusion | %/ serving | mg/ batch | g/ batch |
|---|---|---|---|---|---|---|
| Neobee ® M-5, Capric and Caprylic Acid (Oil Phase) | 3.9684 | 12.6100 | 13.2279 | 2.5506 | 3968.4 | 3.97 |
| Oleic Acid (Oil Phase) | 3.2745 | 10.4050 | 10.9148 | 2.1046 | 3274.5 | 3.27 |
| Vitamin E 5-67 (Oil Phase) | 2.7432 | 8.7170 | 9.1441 | 1.7631 | 2743.2 | 2.74 |
| Benzyl Alcohol (Oil Phase) | 1.6302 | 5.1801 | 5.4339 | 1.0478 | 1630.2 | 1.63 |
| LIPOID 100 S 100 (94% Phosphatidycholine (PC)) (Oil Phase) | 0.7471 | 2.3740 | 2.4903 | 0.4802 | 747.1 | 0.75 |
| Vitamin E TPGS (Oil Phase) | 10.3851 | 33.0000 | 34.6170 | 6.6748 | 10385.1 | 10.39 |
| Glycerin (Oil Phase) | 6.7799 | 21.5440 | 22.5997 | 4.3576 | 6779.9 | 6.78 |
| Riboflavin (1.1 mg overage, need 1 mg) | 0.3462 | 1.1000 | 1.1539 | 0.2225 | 346.2 | 0.35 |
| Molybdenum 0.5% (1 mg × .05 = 50 mcg, need 35 mcg so overage) | 0.3147 | 1.0000 | 1.0490 | 0.2023 | 314.7 | 0.31 |
| pH Adjuster-1 (DI Systems and water purification) (Oil phase) | 0.3147 | 1.0000 | 1.0490 | 0.2023 | 314.7 | 0.31 |
| Glycerin (Glycerin phase) | 96.3347 | 306.1159 | 321.1156 | 61.9167 | 96334.7 | 96.33 |
| Vitamin E TPGS (Glycerin phase) | 4.2964 | 13.6525 | 14.3215 | 2.7614 | 4296.4 | 4.30 |
| Glutathione (Glycerin phase) | 17.3085 | 55.0000 | 57.6950 | 11.1246 | 17308.5 | 17.31 |
| Lactoferrin (94% minimum) (Glycerin phase) | 5.5073 | 17.5000 | 18.3575 | 3.5396 | 5507.3 | 5.51 |
| pH Adjuster-2 (DI Systems and water purification) | 0.2990 | 0.9500 | 0.9966 | 0.1922 | 299.0 | 0.30 |
| Stevia (rebaudioside-A) (Flavor) | 0.5260 | 1.6715 | 1.7534 | 0.3381 | 526.0 | 0.53 |
| Clove oil | 0.3421 | 1.0870 | 1.1403 | 0.2199 | 342.1 | 0.34 |
| Cinnamon Oil | 0.1690 | 0.5370 | 0.5633 | 0.1086 | 169.0 | 0.17 |
| Orange Oil | 0.3007 | 0.9555 | 1.0023 | 0.1933 | 300.7 | 0.30 |
| Vanilla (Wild) (DABK820) | 1.7623 | 5.6000 | 5.8744 | 1.1327 | 1762.3 | 1.76 |
| Totals | 157.350 | 500.000 | 518.625 | 100.0000 | 155587.5 | 157.35 |

The oil phase was prepared by weighing the appropriate amounts of Neobee® M-5 (Capric and Caprylic Acid), Oleic Acid, Vitamin E 5-67, Benzyl Alcohol and LIPOID 100 S 100 (94% Phosphatidycholine (PC)) and then mixing at 72-80° C. using a magnetic stirrer on a hot plate, until all components dissolved (approximately 2 hours) to form the first mixture. In a separate container, Vitamin E TPGS was heated to 60° C. and Glycerin and pH adjuster were added. Once all components dissolved in the first mixture and the first mixture reached a temperature of 60° C., the Vitamin E TPGS, glycerin and pH adjuster mixture was added, and mixed until the components dissolved. Next, clove oil, cinnamon oil, orange oil and vanilla flavor were weighed and added, in that order, and mixed until homogenous. Then the mixture was allowed to cool to room temperature or approximately 30° C.

The glycerin phase was prepared by weighing the appropriate amounts of Glycerin, Vitamin E TPGS, Glutathione, Molybdenum, Riboflavin, Stevia lactoferrin and pH adjuster and adding the components, in that order, into a container containing an Arde Barinco high speed shear homogenizer. Components were continually mixed at room temperature until lactoferrin completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler 30° C. for 1 hour and taken from the cooler and remixed thoroughly. Preparation of the emulsion was followed by addition of flavors/sweeteners, if needed, to make up the batch. After the solution was homogeneous, the solution was poured into hoppers for packaging.

Example 13

Preparation of MAPT Probiotic (*Bifidobacterium infantis*) Formulation

Appropriate quantities of the raw materials were weighed for the 160.38 g batch as shown below:

| Ingredient | (g) per batch | mg/serv. | %/serving |
|---|---|---|---|
| Neobee ® M-5, Capric and Caprylic Acid (Oil Phase) | 3.9684 | 12.6100 | 2.4743 |
| Oleic Acid (Oil Phase) | 3.2745 | 10.4050 | 2.0417 |
| Vitamin E 5-67 (Oil Phase) | 2.7432 | 8.7170 | 1.7105 |
| Benzyl Alcohol (Oil Phase) | 1.6302 | 5.1801 | 1.0164 |
| LIPOID 100 S 100 (94% Phosphatidylcholine (PC)) (Oil Phase) | 0.7471 | 2.3740 | 0.4658 |
| Vitamin E TPGS (Oil Phase) | 10.3851 | 33.0000 | 6.4753 |
| Glycerin (Oil Phase) | 6.7799 | 21.5440 | 4.2274 |
| pH Adjuster-1 (DI Systems and water purification) (Oil phase) | 0.3147 | 1.0000 | 0.1962 |
| Glycerin (Glycerin phase) | 96.5109 | 306.6759 | 60.1762 |
| Vitamin E TPGS (Glycerin phase) | 4.2964 | 13.6525 | 2.6789 |
| BI-26 50 B *Bifidobacteria Infantis* * | 17.3085 | 55.0000 | 10.7921 |
| Lactoferrin (94% minimum) (Glycerin phase) | 5.5073 | 17.5000 | 3.4339 |
| pH Adjuster-2 (DI Systems and water purification) | 0.2990 | 0.9500 | 0.1864 |
| Stevia (rebaudioside-A) (Flavor) | 0.5260 | 1.6715 | 0.3280 |
| Nat Maple Syrup (Gold Coast) (600074) | 0.7868 | 2.5000 | 0.4906 |
| Nat. Belgian Waffle (Gold Coast) (382072) | 1.9826 | 6.3000 | 1.2362 |
| Nat. Banana (Gold Coast) (352992) | 1.5578 | 4.9500 | 0.9713 |
| Vanilla (Gold Coast) (603498) | 1.7623 | 5.6000 | 1.0988 |
| Totals | 160.381 | 534.602 | 100.0000 |

* DUPONT ™ DANISCO ® CUSTOM PROBIOTICS

The oil phase was prepared by weighing the appropriate amounts of Neobee® M-5 (Capric and Caprylic Acid), Oleic Acid, Vitamin E 5-67, Benzyl Alcohol and then mixing without heat using a magnetic stirrer at slow speed, until all components dissolve. LIPOID 100 S 100 (94% Phosphatidycholine (PC)) was added and the mixture heated to about 60° C.-70° C. with stirring to dissolve all ingredients to form the first mixture. In a separate container, Vitamin E TPGS was weighed and heated to 60° C. Once all components dissolved in the first mixture and the first mixture reached a temperature of 60° C., the Vitamin E TPGS was added, and mixed until the components dissolved. A temperature of 60° C. was maintained and Glycerin and pH Adjuster-1 were added. Next, Nat. Maple Syrup (Gold Coast; 600074), Nat. Belgian Waffle (Gold Coast; 382072), Nat. Banana (Gold Coast; 352992) and vanilla flavor (Gold Coast; 603492) were weighed and added, in that order, and mixed until homogenous. The complete oil phase was cooled to room temperature or approximately 30° C.

The glycerin phase was prepared by weighing the appropriate amounts of Glycerin, Vitamin E TPGS, *Bifidobacterium infantis*, Lactoferrin (94% minimum), pH Adjuster-2 and Stevia, and adding the components, in that order, into a container, and then mixing without heat using a magnetic stirrer, until all components dissolved.

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. After the solution was homogeneous, the solution was poured into hoppers for packaging. The finished solution was tested for the amount of *Bifidobacterium infantis* in the solution.

Example 14

Preparation of MAPT Probiotic (*Lactobacillus acidophilus*) Formulation

Appropriate quantities of the raw materials were weighed for the 106.92 g batch as shown below:

| Ingredient | (g) per batch | mg/serv. | %/serving |
|---|---|---|---|
| Neobee ® M-5, Capric and Caprylic Acid (Oil Phase) | 2.6456 | 12.6100 | 2.4743 |
| Oleic Acid (Oil Phase) | 2.1830 | 10.4050 | 2.0417 |
| Vitamin E 5-67 (Oil Phase) | 1.8288 | 8.7170 | 1.7105 |
| Benzyl Alcohol (Oil Phase) | 1.0868 | 5.1801 | 1.0164 |
| LIPOID 100 S 100 (94% Phosphatidycholine (PC)) (Oil Phase) | 0.4981 | 2.3740 | 0.4658 |
| Vitamin E TPGS (Oil Phase) | 6.9234 | 33.0000 | 6.4753 |
| Glycerin (Oil Phase) | 4.5199 | 21.5440 | 4.2274 |
| pH Adjuster-1 (DI Systems and water purification) (Oil phase) | 0.2098 | 1.0000 | 0.1962 |
| Glycerin (Glycerin phase) | 64.3406 | 306.6759 | 60.1762 |
| Vitamin E TPGS (Glycerin phase) | 2.8643 | 13.6525 | 2.6789 |
| LA-14 200 B (*Lb. Acidophilus*)* | 11.5390 | 55.0000 | 10.7921 |
| Lactoferrin (94% minimum) (Glycerin phase) | 3.6715 | 17.5000 | 3.4339 |
| pH Adjuster-2 (DI Systems and water purification) | 0.1993 | 0.9500 | 0.1864 |
| Stevia (rebaudioside-A) (Flavor) | 0.3507 | 1.6715 | 0.3280 |
| Nat Maple Syrup (Gold Coast) (600074) | 0.5245 | 2.5000 | 0.4906 |
| Nat. Belgian Waffle (Gold Coast) (382072) | 1.3217 | 6.3000 | 1.2362 |
| Nat. Banana (Gold Coast) (352992) | 1.0385 | 4.9500 | 0.9713 |
| Vanilla (Gold Coast) (603498) | 1.1749 | 5.6000 | 1.0988 |
| Totals | 106.920 | 509.630 | 100.0000 |

*DUPONT ™ DANISCO ® CUSTOM PROBIOTICS

The oil phase was prepared by weighing the appropriate amounts of Neobee® M-5 (Capric and Caprylic Acid), Oleic Acid, Vitamin E 5-67, Benzyl Alcohol and then mixing without heat using a magnetic stirrer at slow speed, until all components dissolved. LIPOID 100 S 100 (94% Phosphatidycholine (PC)) was added and the mixture heated to about 60° C.-70° C. with stirring to dissolve all ingredients to form the first mixture. In a separate container, Vitamin E TPGS was weighed and heated to 60° C. Once all components dissolved in the first mixture and the first mixture reached a temperature of 60° C., the Vitamin E TPGS was added, and mixed until the components dissolved. A temperature of 60° C. was maintained and Glycerin and pH Adjuster-1 were added. Next, Nat. Maple Syrup (Gold Coast; 600074), Nat. Belgian Waffle (Gold Coast; 382072), Nat. Banana (Gold Coast; 352992) and vanilla flavor (Gold Coast; 603498) were weighed and added, in that order, and mixed until homogenous. The complete oil phase was cooled to room temperature or approximately 30° C.

The glycerin phase was prepared by weighing the appropriate amounts of Glycerin, Vitamin E TPGS, *Lactobacillus acidophilus*, Lactoferrin (94% minimum), pH Adjuster-2 and Stevia, and adding the components, in that order, into a container, and then mixing without heat using a magnetic stirrer, until all components dissolved.

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. After the solution was homogeneous, the solution was poured into hoppers for packaging. The finished solution was tested for the amount of *Lactobacillus acidophilus* in the solution.

Example 15

Preparation of MAPT Probiotic (*Bifidobacterium Lactis*) Formulation

Appropriate quantities of the raw materials were weighed for the 106.92 g batch as shown below:

| Ingredient | (g) per batch | mg/serv. | %/ serving |
|---|---|---|---|
| Neobee ® M-5, Capric and Caprylic Acid (Oil Phase) | 2.6456 | 12.6100 | 2.4743 |
| Oleic Acid (Oil Phase) | 2.1830 | 10.4050 | 2.0417 |
| Vitamin E 5-67 (Oil Phase) | 1.8288 | 8.7170 | 1.7105 |
| Benzyl Alcohol (Oil Phase) | 1.0868 | 5.1801 | 1.0164 |
| LIPOID 100 S 100 (94% Phosphatidycholine (PC)) (Oil Phase) | 0.4981 | 2.3740 | 0.4658 |
| Vitamin E TPGS (Oil Phase) | 6.9234 | 33.0000 | 6.4753 |
| Glycerin (Oil Phase) | 4.5199 | 21.5440 | 4.2274 |
| pH Adjuster-1 (DI Systems and water purification) (Oil phase) | 0.2098 | 1.0000 | 0.1962 |
| Glycerin (Glycerin phase) | 64.3406 | 306.6759 | 60.1762 |
| Vitamin E TPGS (Glycerin phase) | 2.8643 | 13.6525 | 2.6789 |
| BL-04 500 B *Bif. Lactis** | 11.5390 | 55.0000 | 10.7921 |
| Lactoferrin (94% minimum) (Glycerin phase) | 3.6715 | 17.5000 | 3.4339 |
| pH Adjuster-2 (DI Systems and water purification) | 0.1993 | 0.9500 | 0.1864 |
| Stevia (rebaudioside-A) (Flavor) | 0.3507 | 1.6715 | 0.3280 |

-continued

| Ingredient | (g) per batch | mg/serv. | %/ serving |
|---|---|---|---|
| Nat Maple Syrup (Gold Coast) (600074) | 0.5245 | 2.5000 | 0.4906 |
| Nat. Belgian Waffle (Gold Coast) (382072) | 1.3217 | 6.3000 | 1.2362 |
| Nat. Banana (Gold Coast) (352992) | 1.0385 | 4.9500 | 0.9713 |
| Vanilla (Gold Coast) (603498) | 1.1749 | 5.6000 | 1.0988 |
| Totals | 106.920 | 509.630 | 100.0000 |

* DUPONT ™ DANISCO ® CUSTOM PROBIOTICS

The oil phase was prepared by weighing the appropriate amounts of Neobee® M-5 (Capric and Caprylic Acid), Oleic Acid, Vitamin E 5-67 and Benzyl Alcohol and then mixing without heat using a magnetic stirrer at slow speed, until all components dissolved. LIPOID 100 S 100 (94% Phosphatidycholine (PC)) was added and the mixture heated to about 60° C.-70° C. with stirring to dissolve all ingredients to form the first mixture. In a separate container, Vitamin E TPGS was weighed and heated to 60° C. Once all components dissolved in the first mixture and the first mixture reached a temperature of 60° C., the Vitamin E TPGS was added, and mixed until the components dissolved. A temperature of 60° C. was maintained and Glycerin and pH Adjuster 1 were added. Next, Nat. Maple Syrup (Gold Coast; 600074), Nat. Belgian Waffle (Gold Coast; 382072), Nat. Banana (Gold Coast; 352992) and vanilla flavor (Gold Coast; 603498) were weighed and added, in that order, and mixed until homogenous. The complete oil phase was cooled to room temperature or approximately 30° C.

The glycerin phase was prepared by weighing the appropriate amounts of Glycerin, Vitamin E TPGS, *Bifidobacterium lactis*, Lactoferrin (94% minimum), Ph Adjuster-2 and Stevia, and adding the components, in that order, into a container, and then mixing without heat using a magnetic stirrer, until all components dissolved.

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. After the solution was homogeneous, the solution was poured into hoppers for packaging. The finished solution was tested for the amount of *Bifidobacterium lactis* in the solution.

Example 16

Preparation of MAPT Probiotic (*Bifidobacterium Longum*) Formulation

Appropriate quantities of the raw materials were weighed for the 1.049 g batch as shown below:

| Ingredient | (g) per batch | mg/serv. | %/ serving |
|---|---|---|---|
| Neobee ® M-5, Capric and Caprylic Acid (Oil Phase) | 0.0265 | 12.6100 | 2.5220 |
| Oleic Acid (Oil Phase) | 0.0218 | 10.4050 | 2.0810 |
| Vitamin E 5-67 (Oil Phase) | 0.0183 | 8.7170 | 1.7434 |

-continued

| Ingredient | (g) per batch | mg/serv. | %/serving |
|---|---|---|---|
| Benzyl Alcohol (Oil Phase) | 0.0109 | 5.1801 | 1.0360 |
| LIPOID 100 S 100 (94% Phosphatidycholine (PC)) (Oil Phase) | 0.0050 | 2.3740 | 0.4748 |
| Vitamin E TPGS (Oil Phase) | 0.0692 | 33.0000 | 6.6000 |
| Glycerin (Oil Phase) | 0.0452 | 21.5440 | 4.3088 |
| Ph Adjuster-1 (DI Systems and water purification) (Oil phase) | 0.0021 | 1.0000 | 0.2000 |
| Glycerin (Glycerin phase) | 0.6434 | 306.6759 | 61.3352 |
| Vitamin E TPGS (Glycerin phase) | 0.0286 | 13.6525 | 2.7305 |
| Bifilon-50T (Bifidobacterium Longum)* | 0.1154 | 55.0000 | 11.000 |
| Lactoferrin (94% minimum) (Glycerin phase) | 0.0367 | 17.5000 | 3.5000 |
| pH Adjuster-2 (DI Systems and water purification) | 0.0020 | 0.9500 | 0.1900 |
| Stevia (rebaudioside-A) (Flavor) | 0.0035 | 1.6715 | 0.3343 |
| Nat Maple Syrup (Gold Coast) (600074) | 0.0052 | 2.5000 | 0.5000 |
| Nat. Belgian Waffle (Gold Coast) (382072) | 0.0034 | 1.6200 | 0.3240 |
| Vanilla (Gold Coast) (603498) | 0.0117 | 5.6000 | 0.0000 |
| Totals | 1.049 | 500.000 | 100.0000 |

The oil phase was prepared by weighing the appropriate amounts of Neobee® M-5 (Capric and Caprylic Acid), Oleic Acid, Vitamin E 5-67 and Benzyl Alcohol and then mixing without heat using a magnetic stirrer at slow speed, until all components dissolve. LIPOID 100 S 100 (94% Phosphatidycholine (PC)) was added and the mixture was heated to about 60° C.-70° C. with stirring to dissolve all ingredients to form the first mixture. In a separate container, Vitamin E TPGS was weighed and heated to 60° C. Once all components dissolved in the first mixture and the first mixture reached a temperature of 60° C., the Vitamin E TPGS was added, and mixed until the components dissolved. A temperature of 60° C. was maintained and Glycerin and Ph Adjuster-1 added. Next, Nat. Maple Syrup (Gold Coast; 600074), Nat. Belgian Waffle (Gold Coast; 382072), and vanilla flavor (Gold Coast; 603498) were weighed and added, in that order, and mixed until homogenous. The complete oil phase was cooled to room temperature or approximately 30° C.

The glycerin phase was prepared by weighing the appropriate amounts of Glycerin, Vitamin E TPGS, Bifidobacterium longum, Lactoferrin (94% minimum), Ph Adjuster-2 and Stevia, and adding the components, in that order, into a container, and then mixing without heat using a magnetic stirrer, until all components dissolved.

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. After the solution was homogeneous, the solution was poured into hoppers for packaging. The finished solution was tested for the amount of Bifidobacterium Longum in the solution.

Example 17

Preparation of Dry Powder Containing Lactoferrin and Bifidobacterium Longum and MCT Oil with SFAE

TABLE 5

Preparation of Lactoferrin and Probiotics with MCT Oil Preparation

| Ingredient | %/serving before evaporation | g/batch | %/serving after evaporation |
|---|---|---|---|
| Water | 57.500 | 460 | 0 |
| KHCO$_3$ | 3.333 | 26.66666667 | 7.84 |
| Cluster Dextrin | 6.367 | 50.93333333 | 14.98 |
| SFAE | 4.250 | 34 | 10.00 |
| Saladizer® emulsifier® | 0.067 | 0.533333333 | 0.16 |
| Lactoferrin | 6.187 | 49.49333333 | 14.56 |
| Bifidobacterium Longum | 4.667 | 37.33333333 | 10.98 |
| Solid MCT Oil | 17.630 | 141.04 | 41.48 |
| Totals | 100.000 | 800.0000 | 100.00 |

The powder contains 10.98% Bifidobacterium longum and 41.48% MCT Oil, which includes about 1.1% TPGS.

The water phase was prepared by weighing the appropriate amounts of water, Saladizer® Emulsifier®, Cluster Dextrin, SFAE and KHCO$_3$ and then mixing at a temperature not more than 55° C.

The oil phase was prepared by weighing the appropriate amounts of solid MCT oil and lactoferrin. Then, Bifidobacterium longum was mixed into the solid MCT oil solution at 40° C. The oil phase was then passed through a filter.

The emulsion was prepared by adding the oil phase to the water phase (where each are at approximately 60° C.), slowly while mixing at low to medium RPM using an Arde Barinco Mixer Type 74D (Serial No. L-1274) until the mixture is homogeneous, or approximately 5 minutes. The emulsion was allowed to cool to 30° C. in a cooler for 1 hour and taken from the cooler and remixed thoroughly. The resulting mixture was at a pH of approximately 8.0 and included about 10.98% Bifidobacterium longum and 41.48% MCT Oil.

The emulsion was spray dried as described in Example 9. The resulting powder was cooled to 35° C. and packaged into appropriate containers.

Example 18

Preparation of High Dimer d-α-Tocopheryl Polyethylene Glycol 1000 Succinate

A. Method of Producing TPGS Compositions d-α-Tocopheryl polyethylene glycol 1000 succinate (TPGS 1000), used in the compositions herein, include the well-known TPGS that is commercially available and manufactured to maximize the concentration of monomer (such as those sold by Eastman), and those that are manufactured so that the resulting water-soluble vitamin E derivative mixtures (compositions) include a mixture of monomers and dimers of the water-soluble vitamin E derivatives (referred to as high dimer TPGS) (see, U.S. Publication No. US-2014-0271593-A1, and published International PCT Publication No. WO 2014/151109, which describe such mixtures). Briefly, as described in the published applications, the high dimer TPGS was synthesized from vitamin E succinate according to the following general procedure Polyethylene glycol (PEG) 1000 (168.7 kg) was added to a reaction flask containing 1430 L of toluene, followed by the addition of 71.5 kg of vitamin E (α-tocopheryl acid) succinate and 2.86 kg of p-toluene sulfonic acid. The reaction mixture was heated to 110-112° C. and refluxed for up to 6.5 hours, removing the water formed during the esterification reaction by azeotropic distillation. The reaction was terminated when the desired amounts of TPGS monomer and TPGS dimer were formed, as indicated by high performance liquid chromatography (HPLC) and thin layer chromatography (TLC), resulting in the TPGS compositions set forth in Table 6 below. Each TPGS composition in Table 6 was formed by terminating the reaction at a different time point, up to 6.5 hours, and contained various amounts of TPGS monomer and TPGS dimer. The remainder of the TPGS composition was made up of unreacted starting materials, such as vitamin E and PEG. The reaction was terminated by cooling the reaction mixture to room temperature, followed by washing with 25 L of a 10% solution of NaHCO$_3$. The solution was stirred for 10 minutes, and after stirring was allowed to separate into layers. The organic (toluene) layer was removed, 6 kg of activated carbon (charcoal) was added, and the solution was heated to 55-60° C. and maintained at this temperature for 1 hour. The solution was then cooled to room temperature, filtered through 10 kg of Celite® Hyflo® filter aid (Sigma Aldrich, St. Louis, Mo.) and then washed with 100 L of toluene. The filtered toluene solution was concentrated by vacuum distillation below 60° C. to remove the toluene. Water (140 L) was added to remove traces of toluene and was then removed via vacuum distillation below 60° C. to obtain ~180 kg of a crude α-tocopheryl polyethylene glycol 1000 succinate composition that contained a mixture of TPGS monomer and TPGS dimer, along with unreacted PEG 1000 and α-tocopherol.

TABLE 6

Amounts of TPGS monomer and TPGS dimer formed during reaction

| TPGS composition | Monomer (%) | Dimer (%) | Total (% monomer + % dimer) |
|---|---|---|---|
| 1 | 43.90 | 53.90 | 97.80 |
| 2 | 42.80 | 48.80 | 91.60 |
| 3 | 40.95 | 53.15 | 94.10 |
| 4 | 43.52 | 49.80 | 93.32 |
| 5 | 55.88 | 29.27 | 85.15 |
| 6 | 52.92 | 33.70 | 86.62 |
| 7 | 42.76 | 51.10 | 93.86 |
| 8 | 40.39 | 54.90 | 95.29 |
| 9 | 57.70 | 40.40 | 98.10 |
| 10 | 39.35 | 35.56 | 74.91 |
| 11 | 60.00 | 38.10 | 98.10 |

A series of extractions were performed on the crude TPGS composition. The crude TPGS composition (~180 kg) was dissolved in 360 L of methanol and then 540 L of cyclohexane was added. The solution was stirred and then allowed to separate into layers. The cyclohexane layer was removed and an additional 540 L of cyclohexane was added to the remaining methanol layer. The solution was stirred and then allowed to separate into layers. The cyclohexane layer was again removed and an additional 540 L of cyclohexane was added to the remaining methanol layer. The solution was again stirred and allowed to separate into layers. The cyclohexane layer was removed, and the remaining methanol layer was further diluted with an additional 270 L of methanol. Activated carbon (18 kg) was added and the solution was heated to 55-60° C. and maintained at this temperature for 1 hour. The solution was then cooled to room temperature, filtered through 30 kg of Celite® Hyflo® filter aid, and washed with 100 L of methanol. The methanol solution was passed through a micron filter, then concentrated via vacuum distillation below 60° C. to obtain ~98-102 kg of a TPGS composition. All traces of solvent were then removed by purging with nitrogen at 55° C. for two hours to obtain ~98-102 kg of a purified TPGS composition that contained TPGS monomer and TPGS dimer.

A typical batch of TPGS prepared to contain a high dimer concentration, and used in the Examples below, had the following components:
TPGS monomer: 48%
TPGS dimer: 51%
Vitamin E: 0.42%
Vitamin E succinate: 0.46%.
Other typical batches contained:
TPGS monomer: 46.09%-43.15% w/w
TPGS dimer: 39.07%-50.28% w/w
Other: up to about 3%-3.2% w/w
For example, the batches used in Example 11 contained:
TPGS monomer: 46.55%-48.72% w/w
TPGS dimer: 46.88%-47.33% w/w
Other: up to about 3.95%-6.55% w/w B. Evaluation of the Clarity of the TPGS-Containing Compositions by a Turbidity Analysis The clarity of the TPGS compositions prepared above was evaluated by a turbidity analysis. TPGS compositions 1-11 were formulated as 1 g concentrates and each was dissolved in 8 oz. of water. The resulting aqueous liquid dilution compositions then were evaluated for clarity by measuring turbidity using a nephelometer. Results of the evaluation are set forth in Table 7 below.

Each of the eleven TPGS compositions listed in Table 6 above was diluted in water (purified according to the provided methods) using the following steps.

Eight ounces of water was heated in a Pyrex® beaker by placing the beaker on a Thermolyne hot plate (Model #846925) until the water reached 49.8° C. The TPGS composition concentrate was then added to the heated water and stirred with a stir rod until dispersed. The resulting aqueous TPGS composition was cooled to room temperature (about 25° C.). The cooled aqueous TPGS composition was added to an amber-glass screw-top vial (Alcon) for evaluation.

The vials containing the aqueous TPGS compositions were sent to ACZ Laboratories, Inc. (Steamboat Springs, Colo.) for turbidity analysis using a nephelometer. Results are listed in the form of Nephelometric Turbidity Units (NTU) and are indicated in Table 7 below.

TABLE 7

Turbidity (NTU) of aqueous TPGS compositions

| TPGS composition | Monomer (%) | Dimer (%) | Total (% monomer + % dimer) | Turbidity (NTU) |
|---|---|---|---|---|
| 1 | 43.90 | 53.90 | 97.80 | 8 |
| 2 | 42.80 | 48.80 | 91.60 | 8.2 |
| 3 | 40.95 | 53.15 | 94.10 | 10 |
| 4 | 43.52 | 49.80 | 93.32 | 10 |
| 5 | 55.88 | 29.27 | 85.15 | 14 |
| 6 | 52.92 | 33.70 | 86.62 | 14 |
| 7 | 42.76 | 51.10 | 93.86 | 18.5 |
| 8 | 40.39 | 54.90 | 95.29 | 39.4 |

TABLE 7-continued

Turbidity (NTU) of aqueous TPGS compositions

| TPGS composition | Monomer (%) | Dimer (%) | Total (% monomer + % dimer) | Turbidity (NTU) |
|---|---|---|---|---|
| 9 | 57.70 | 40.40 | 98.10 | 71 |
| 10 | 39.35 | 35.56 | 74.91 | 80 |
| 11 | 60.00 | 38.10 | 98.10 | 80 |

Example 19

Preparation of MAPT Probiotic (*Lactobacillus rhamnosus* GG (Sold Under the Trademark Probio-Tec® LGG®)) Formulation Appropriate quantities of the raw materials were weighed for the 157.35 g batch as shown below:

| Ingredient | mg/ serving | %/ serving | mg/ batch |
|---|---|---|---|
| Neobee ® M-5, Capric and Caprylic Acid (Oil Phase) | 12.6100 | 2.5220 | 3968.4 |
| Oleic Acid (Oil Phase) | 10.4050 | 2.0810 | 3274.5 |
| Vitamin E 5-67 (Oil Phase) | 8.7170 | 1.7434 | 2743.2 |
| Benzyl Alcohol (Oil Phase) | 5.1801 | 1.0360 | 1630.2 |
| LIPOID 100 S 100 (94% Phosphatidycholine (PC)) (Oil Phase) | 2.3740 | 0.4748 | 747.1 |
| Vitamin E TPGS (Oil Phase) | 33.0000 | 6.6000 | 10385.1 |
| Glycerin (Oil Phase) | 21.5440 | 4.3088 | 6779.9 |
| Ph Adjuster-1 (DI Systems and water purification) (Oil phase) | 1.0000 | 0.2000 | 314.7 |
| Glycerin (Glycerin phase) | 292.3959 | 58.4792 | 92017.0 |
| Vitamin E TPGS (Glycerin phase) | 13.6525 | 2.7305 | 4296.4 |
| Probio-Tec *Lactobacillus rhamnosus* GG LGG ® Conc. 3.5E+11 cfu/g (350 B) | 55.0000 | 11.0000 | 17308.5 |
| Lactoferrin (94% minimum) (Glycerin phase) | 17.5000 | 3.5000 | 5507.3 |
| Ph Adjuster-2 (DI Systems and water purification) | 0.9500 | 0.1900 | 299.0 |
| Stevia (rebaudioside-A) (Flavor) | 1.6715 | 0.3343 | 526.0 |
| Nat. Burgundy Cherry (Mission) (CH-172) | 24.0000 | 4.8000 | 7552.8 |
| Totals | 500 | 100 | 157350.0 |

The oil phase was prepared by weighing the appropriate amounts of Neobee® M-5 (Capric and Caprylic Acid), Oleic Acid, Vitamin E 5-67 and Benzyl Alcohol and then mixing without heat using a magnetic stirrer, until all components dissolved to form the first mixture. LIPOID 100 S 100 (94% Phosphatidycholine (PC)) was added to the oil phase and dissolved at approximately 60° C.-70° C. Once the oil phase (first mixture) was dissolved, Vitamin E TPGS, Glycerin and pH adjuster-1 were added and mixed until all components were dissolved and the mixture was cooled.

The glycerin phase was prepared by weighing the appropriate amounts of Glycerin and Vitamin E TPGS and mixing gently until dissolved without heat. Ph Adjuster-2 was added and mixed gently until dissolved. Probio-Tec® *Lactobacillus rhamnosus* GG (LGG®) was added and mixed gently until dissolved. Lactoferrin was added to a container containing the glycerin phase (Glycerin, Vitamin E TPGS, Ph Adjuster-2 and Probio-Tec® *Lactobacillus rhamnosus* GG (LGG®)) and all components were mixed with an Arde Barinco high speed shear homogenizer. Components were continually mixed at room temperature until lactoferrin completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture was homogeneous, or approximately 5 minutes. The emulsion was allowed to cool in a cooler to 30° C. for 1 hour and taken from the cooler and remixed thoroughly. Preparation of the emulsion was followed by addition of Stevia (rebaudioside-A) and Nat. Burgundy Cherry flavors/sweeteners to make up the batch of 157.35 g. After the solution was homogeneous, the solution was poured into hoppers for packaging. The finished solution was tested for the amount of *Lactobacillus rhamnosus* GG in the solution.

Example 20

Preparation of MAPT Probiotic (*Bifidobacterium infantis*) Formulation

Appropriate quantities of the raw materials were weighed for the 157.35 g batch as shown below:

| Ingredient | mg/ serving | %/ serving | (g) per batch |
|---|---|---|---|
| Neobee ® M-5, Capric and Caprylic Acid (Oil Phase) | 12.6100 | 2.5220 | 3.9684 |
| Oleic Acid (Oil Phase) | 10.4050 | 2.0810 | 3.2745 |
| Vitamin E 5-67 (Oil Phase) | 8.7170 | 1.7434 | 2.7432 |
| Benzyl Alcohol (Oil Phase) | 5.1801 | 1.0360 | 1.6302 |
| LIPOID 100 S 100 (94% Phosphatidylcholine (PC)) (Oil Phase) | 2.3740 | 0.4748 | 0.7471 |
| Vitamin E TPGS (Oil Phase) | 33.0000 | 6.6000 | 10.3851 |
| Glycerin (Oil Phase) | 21.5440 | 4.3088 | 6.7799 |
| pH Adjuster-1 (DI Systems and water purification) (Oil phase) | 1.0000 | 0.2000 | 0.3147 |
| Glycerin (Glycerin phase) | 297.0459 | 59.4092 | 93.4803 |
| Vitamin E TPGS (Glycerin phase) | 13.6525 | 2.7305 | 4.2964 |
| BI-26 50 B *Bifidobacteria Infantis* | 55.0000 | 11.0000 | 17.3085 |
| Lactoferrin (94% minimum) (Glycerin phase) | 17.5000 | 3.5000 | 5.5073 |
| pH Adjuster-2 (DI Systems and water purification) | 0.9500 | 0.1900 | 0.2990 |
| Stevia (rebaudioside-A) (Flavor) | 1.6715 | 0.3343 | 0.5260 |
| Nat Maple Syrup (Gold Coast) (600074) | 2.5000 | 0.5000 | 0.7868 |

| Ingredient | mg/ serving | %/ serving | (g) per batch |
|---|---|---|---|
| Nat. Belgian Waffle (Gold Coast) (382072) | 6.3000 | 1.2600 | 1.9826 |
| Nat. Banana (Gold Coast) (352992) | 4.9500 | 0.9900 | 1.5578 |
| Vanilla (Gold Coast) (603498) | 5.6000 | 1.1200 | 1.7623 |
| Totals | 500 | 100.0000 | 157.350 |

The oil phase was prepared by weighing the appropriate amounts of Neobee® M-5 (Capric and Caprylic Acid), Oleic Acid, Vitamin E 5-67 and Benzyl Alcohol and then mixing without heat using a magnetic stirrer at slow speed, until all components dissolve. LIPOID 100 S 100 (94% Phosphatidycholine (PC)) was added to the oil phase and dissolved at approximately 60° C.-70° C. In a separate container, Vitamin E TPGS was weighed and heated to 60° C. Once all components dissolved in the first mixture and the first mixture reached a temperature of 60° C., the Vitamin E TPGS was added, and mixed until the components dissolved. A temperature of 60° C. was maintained and Glycerin and pH Adjuster-1 were added. Then the oil phase was cooled to 30° C. in a cooler. Next, Nat. Maple Syrup (Gold Coast; 600074), Nat. Belgian Waffle (Gold Coast; 382072), Nat. Banana (Gold Coast; 352992) and vanilla flavor (Gold Coast; 603498) and Stevia, were weighed and added, in that order, and mixed until homogenous. The complete oil phase was cooled to room temperature or approximately 30° C.

The glycerin phase was prepared by weighing the appropriate amounts of Glycerin, Vitamin E TPGS, pH Adjuster-2, *Bifidobacterium infantis* and Lactoferrin (94% minimum), and adding the components, in that order, into a container, and then mixing without heat using a magnetic stirrer, until all components dissolved.

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. After the solution was homogeneous, the solution was poured into hoppers for packaging. The finished solution was tested for the amount of *Bifidobacterium infantis* in the solution.

Example 21

Preparation of MAPT Probiotic (*Bifidobacterium longum*) Formulation

Appropriate quantities of the raw materials were weighed for the 157.35 g batch as shown below:

| Ingredient | (g) per batch | mg/serv. | %/serving |
|---|---|---|---|
| Neobee ® M-5, Capric and Caprylic Acid (Oil Phase) | 3.9684 | 12.6100 | 2.5220 |
| Oleic Acid (Oil Phase) | 3.2745 | 10.4050 | 2.0810 |
| Vitamin E 5-67 (Oil Phase) | 2.7432 | 8.7170 | 1.7434 |
| Benzyl Alcohol (Oil Phase) | 1.6302 | 5.1801 | 1.0360 |
| LIPOID 100 S 100 (94% Phosphatidycholine (PC)) (Oil Phase) | 0.7471 | 2.3740 | 0.4748 |
| Vitamin E TPGS (Oil Phase) | 10.3851 | 33.0000 | 6.6000 |
| Glycerin (Oil Phase) | 6.7799 | 21.5440 | 4.3088 |
| Ph Adjuster-1 (DI Systems and water purification) (Oil phase) | 0.3147 | 1.0000 | 0.2000 |
| Glycerin (Glycerin phase) | 92.0170 | 292.3959 | 58.4792 |
| Vitamin E TPGS (Glycerin phase) | 4.2964 | 13.6525 | 2.7305 |
| *Bif. Longum* 100 B cfu/g | 17.3085 | 55.0000 | 11.0000 |
| Lactoferrin (94% minimum) (Glycerin phase) | 5.5073 | 17.5000 | 3.5000 |
| Ph Adjuster-2 (DI Systems and water purification) | 0.2990 | 0.9500 | 0.1900 |
| Stevia (rebaudioside-A) (Flavor) | 0.5260 | 1.6715 | 0.3343 |
| Nat. Burgundy Cherry (Mission) (CH-172) | 7.5528 | 24.0000 | 4.8000 |
| Totals | 157.350 | 500.000 | 100.0000 |

The oil phase was prepared by weighing the appropriate amounts of Neobee® M-5 (Capric and Caprylic Acid), Oleic Acid, Vitamin E 5-67 and Benzyl Alcohol and then mixing without heat using a magnetic stirrer at slow speed, until all components dissolve. LIPOID 100 S 100 (94% Phosphatidycholine (PC)) was added and the solution was mixed to dissolve all ingredients at approximately 60° C.-70° C. to form the first mixture. In a separate container, Vitamin E TPGS was weighed and heated to 60° C. Once all components dissolved in the first mixture and the first mixture reached a temperature of 60° C., the Vitamin E TPGS was added, and mixed until the components dissolved. A temperature of 60° C. was maintained and Glycerin and pH Adjuster-1 were added. Next, Natural Burgundy Cherry and Stevia were weighed and added and mixed until homogenous. The complete oil phase was then cooled to room temperature or approximately 30° C.

The glycerin phase was prepared by weighing the appropriate amounts of Glycerin, Vitamin E TPGS, pH Adjuster-2, *Bifidobacterium longum*, and Lactoferrin (94% minimum), and adding the components, in that order, into a container, and then mixing without heat using a magnetic stirrer, until all components dissolved.

The emulsion was prepared by adding the oil phase to the glycerin phase (where each are at approximately 115° F.)

slowly while mixing at low to medium RPM using an Arde Barinco Mixer Type 74D (Serial No. L-1274) until the mixture was homogeneous, or approximately 5 minutes. The emulsion was allowed to cool in a cooler 30° C. for 1 hour and taken from the cooler and remixed thoroughly. After the solution was homogeneous, the solution was poured into hoppers for packaging. The finished solution was tested for the amount of *Bifidobacterium longum* in the solution.

Example 22

Preparation of MAPT Probiotic (*Bifidobacterium lactis*) Formulation

Appropriate quantities of the raw materials were weighed for the 209.8 g batch as shown below:

| Ingredient | (g) per batch | mg/serv. | %/serving |
|---|---|---|---|
| Neobee ® M-5, Capric and Caprylic Acid (Oil Phase) | 5.2912 | 12.6100 | 2.5220 |
| Oleic Acid (Oil Phase) | 4.3659 | 10.4050 | 2.0810 |
| Vitamin E 5-67 (Oil Phase) | 3.6577 | 8.7170 | 1.7434 |
| Benzyl Alcohol (Oil Phase) | 2.1736 | 5.1801 | 1.0360 |
| LIPOID 100 S 100 (94% Phosphatidylcholine (PC)) (Oil Phase) | 0.9961 | 2.3740 | 0.4748 |
| Vitamin E TPGS (Oil Phase) | 13.8468 | 33.0000 | 6.6000 |
| Glycerin (Oil Phase) | 9.0399 | 21.5440 | 4.3088 |
| pH Adjuster-1 (DI Systems and water purification) (Oil phase) | 0.4196 | 1.0000 | 0.2000 |
| Glycerin (Glycerin phase) | 124.6405 | 297.0459 | 59.4092 |
| Vitamin E TPGS (Glycerin phase) | 5.7286 | 13.6525 | 2.7305 |
| *Bifidobacterium lactis* | 23.0780 | 55.0000 | 11.0000 |
| Lactoferrin (94% minimum) (Glycerin phase) | 7.3430 | 17.5000 | 3.5000 |
| pH Adjuster-2 (DI Systems and water purification) | 0.3986 | 0.9500 | 0.1900 |
| Stevia (rebaudioside-A) (Flavor) | 0.7014 | 1.6715 | 0.3343 |
| Nat Maple Syrup (Gold Coast) (600074) | 1.0490 | 2.5000 | 0.5000 |
| Nat. Belgian Waffle (Gold Coast) (382072) | 2.6435 | 6.3000 | 1.2600 |
| Nat. Banana (Gold Coast) (352992) | 2.0770 | 4.9500 | 0.9900 |
| Vanilla (Gold Coast) (603498) | 2.3498 | 5.6000 | 1.1200 |
| Totals | 209.800 | 500.000 | 100.0000 |

The oil phase was prepared by weighing the appropriate amounts of Neobee® M-5 (Capric and Caprylic Acid), Oleic Acid, Vitamin E 5-67 and Benzyl Alcohol and then mixing without heat using a magnetic stirrer at slow speed, until all components dissolved. LIPOID 100 S 100 (94% Phosphatidycholine (PC)) was added and the solution was mixed to dissolve all ingredients at approximately 60° C.-70° C. to form the first mixture. In a separate container, Vitamin E TPGS was weighed and heated to 60° C. Once all components dissolved in the first mixture and the first mixture reached a temperature of 60° C., the Vitamin E TPGS was added, and mixed until the components dissolved. A temperature of 60° C. was maintained and Glycerin and pH Adjuster-1 were added. A temperature of 60° C. was maintained and Glycerin and pH Adjuster-1 added. Next, Nat. Maple Syrup (Gold Coast; 600074), Nat. Belgian Waffle (Gold Coast; 382072), Nat. Banana (Gold Coast; 352992) and vanilla flavor (Gold Coast; 603498) and Stevia were weighed and added, in that order, and mixed until homogenous. The complete oil phase was cooled to room temperature or approximately 30° C.

The glycerin phase was prepared by weighing the appropriate amounts of Glycerin, Vitamin E TPGS, pH Adjuster-2, *Bifidobacterium lactis*, and Lactoferrin (94% minimum), and adding the components, in that order, into a container, and then mixing without heat using a magnetic stirrer, until all components dissolved.

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. After the solution was homogeneous, the solution was poured into hoppers for packaging. The finished solution was tested for the amount of *Bifidobacterium lactis* in the solution.

Example 23

Preparation of MAPT Probiotic (*Lactobacillus acidophilus*) Formulation

Appropriate quantities of the raw materials were weighed for the 104.9 g batch as shown below:

| Ingredient | (g) per batch | mg/serv. | %/serving |
|---|---|---|---|
| Neobee ® M-5, Capric and Caprylic Acid (Oil Phase) | 2.6456 | 12.6100 | 2.5220 |
| Oleic Acid (Oil Phase) | 2.1830 | 10.4050 | 2.0810 |
| Vitamin E 5-67 (Oil Phase) | 1.8288 | 8.7170 | 1.7434 |
| Benzyl Alcohol (Oil Phase) | 1.0868 | 5.1801 | 1.0360 |

| Ingredient | (g) per batch | mg/serv. | %/serving |
|---|---|---|---|
| LIPOID 100 S 100 (94% Phosphatidylcholine (PC)) (Oil Phase) | 0.4981 | 2.3740 | 0.4748 |
| Vitamin E TPGS (Oil Phase) | 6.9234 | 33.0000 | 6.6000 |
| Glycerin (Oil Phase) | 4.5199 | 21.5440 | 4.3088 |
| pH Adjuster-1 (DI Systems and water purification) (Oil phase) | 0.2098 | 1.0000 | 0.2000 |
| Glycerin (Glycerin phase) | 62.3202 | 297.0459 | 59.4092 |
| Vitamin E TPGS (Glycerin phase) | 2.8643 | 13.6525 | 2.7305 |
| *Lactobacillus acidophilus** | 11.5390 | 55.0000 | 11.0000 |
| Lactoferrin (94% minimum) (Glycerin phase) | 3.6715 | 17.5000 | 3.5000 |
| pH Adjuster-2 (DI Systems and water purification) | 0.1993 | 0.9500 | 0.1900 |
| Stevia (rebaudioside-A) (Flavor) | 0.3507 | 1.6715 | 0.3343 |
| Nat Maple Syrup (Gold Coast) (600074) | 0.5245 | 2.5000 | 0.5000 |
| Nat. Belgian Waffle (Gold Coast) (382072) | 1.3217 | 6.3000 | 1.2600 |
| Nat. Banana (Gold Coast) (352992) | 1.0385 | 4.9500 | 0.9900 |
| Vanilla (Gold Coast) (603498) | 1.1749 | 5.6000 | 1.1200 |
| Totals | 104.900 | 500.000 | 100.0000 |

*DPtechnology ® Probiotic Danisco

The oil phase was prepared by weighing the appropriate amounts of Neobee® M-5 (Capric and Caprylic Acid), Oleic Acid, Vitamin E 5-67 and Benzyl Alcohol and then mixing without heat using a magnetic stirrer at slow speed, until all components dissolved. LIPOID 100 S 100 (94% Phosphatidylcholine (PC)) was added and the solution was mixed to dissolve all ingredients at approximately 60° C.-70° C. to form the first mixture. Once all components dissolved in the first mixture and the first mixture reached a temperature of 60° C., the Vitamin E TPGS was added, and mixed until the components dissolved. A temperature of 60° C. was maintained and Glycerin and pH Adjuster-1 added. Next, Nat. Maple Syrup (Gold Coast; 600074), Nat. Belgian Waffle (Gold Coast; 382072), Nat. Banana (Gold Coast; 352992) and vanilla flavor (Gold Coast; 603498) and Stevia were weighed and added, in that order, and mixed until homogenous. The complete oil phase was cooled to room temperature or approximately 30° C.

The glycerin phase was prepared by weighing the appropriate amounts of Glycerin, Vitamin E TPGS, pH Adjuster-2, *Lactobacillus acidophilus*, Lactoferrin (94% minimum), and adding the components, in that order, into a container, and then mixing without heat using a magnetic stirrer, until all components dissolved.

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler to 30° C. for 1 hour and taken from the cooler and remixed thoroughly. After the solution was homogeneous, the solution was poured into hoppers for packaging. The finished solution was tested for the amount of *Lactobacillus acidophilus* in the solution.

Example 24

Preparation of MAPT Probiotic (*Bifidobacteria Infantis*) Formulation

Appropriate quantities of the raw materials were weighed for the 157.35 g batch as shown below:

| Ingredient | mg/serving | %/serving | mg/batch |
|---|---|---|---|
| Neobee ® M-5, Capric and Caprylic Acid (Oil Phase) | 26.2625 | 5.2525 | 8264.8 |
| Oleic Acid (Oil Phase) | 10.4050 | 2.0810 | 3274.5 |
| Vitamin E 5-67 (Oil Phase) | 8.7170 | 1.7434 | 2743.2 |
| Benzyl Alcohol (Oil Phase) | 5.1801 | 1.0360 | 1630.2 |
| LIPOID 100 S 100 (94% Phosphatidylcholine (PC)) (Oil Phase) | 2.3740 | 0.4748 | 747.1 |
| Glycerin (Oil Phase) | 21.5440 | 4.3088 | 6779.9 |
| Ph Adjuster-1 (DI Systems and water purification) (Oil phase) | 1.0000 | 0.2000 | 314.7 |
| Glycerin (Glycerin phase) | 330.0459 | 66.0092 | 103865.4 |
| BI-26 50B *Bif. Infantis** | 55.0000 | 11.0000 | 17308.5 |
| Lactoferrin (94% minimum) (Glycerin phase) | 17.5000 | 3.5000 | 5507.3 |
| Ph Adjuster-2 (DI Systems and water purification) | 0.9500 | 0.1900 | 299.0 |
| Stevia (rebaudioside-A) (Flavor) | 1.6715 | 0.3343 | 526.0 |
| Nat Maple Syrup (Gold Coast) (600074) | 2.5000 | 0.5000 | 786.8 |
| Nat. Belgian Waffle (Gold Coast) (382072) | 6.3000 | 1.2600 | 1982.6 |
| Nat. Banana (Gold Coast) (352992) | 4.9500 | 0.9900 | 1557.8 |
| Vanilla (Gold Coast) (603498) | 5.6000 | 1.1200 | 1762.3 |
| Totals | 500 | 100 | 157350.0 |

*DPtechnology ® Probiotic from Danisco

The oil phase was prepared by weighing the appropriate amounts of Neobee® M-5, Capric and Caprylic Acid, Oleic Acid, Vitamin E 5-67 and Benzyl Alcohol, and then mixing without heat using a magnetic stirrer, until all components dissolve to form the first mixture. LIPOID 100 S 100 (94% Phosphatidycholine (PC)) was added and dissolved at approximately 60° C.-70° C. Once the oil phase (first mixture) was dissolved, Glycerin and pH adjuster-1 were added and mixed until all components were dissolved and the mixture was cooled. Next, Nat. Maple Syrup (Gold Coast; 600074), Nat. Belgian Waffle (Gold Coast; 382072), Nat. Banana (Gold Coast; 352992) and vanilla flavor (Gold Coast; 603492) were weighed and added, in order, and mixed until homogenous. The complete oil phase was cooled to room temperature or approximately 30° C.

The glycerin phase was prepared by weighing the appropriate amounts of Glycerin, Ph Adjuster-2 and Stevia and mixing gently until dissolved. *Bifidobacteria Infantis* was added and mixed gently until dissolved. Lactoferrin was added into a container containing the glycerin phase and all components were mixed with an Arde Barinco high speed shear homogenizer. Components were continually mixed at room temperature until lactoferrin completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler 30° C. for 1 hour and taken from the cooler and remixed thoroughly. Preparation of the emulsion was followed by addition of flavors/sweeteners, if needed, to make up the batch of 157.35 g. After the solution is homogeneous, the solution was poured into hoppers for packaging. The finished solution was tested for the amount of *Bifidobacteria Infantis* in the solution.

Example 25

Preparation of MAPT Probiotic (*Bifidobacterium Longum*) Formulation

Appropriate quantities of the raw materials were weighed for the 157.35 g batch as shown below:

| Ingredient | mg/serving | %/serving | mg/batch |
|---|---|---|---|
| Neobee ® M-5, Capric and Caprylic Acid (Oil Phase) | 26.2625 | 5.2525 | 8264.8 |
| Oleic Acid (Oil Phase) | 10.4050 | 2.0810 | 3274.5 |
| Vitamin E 5-67 (Oil Phase) | 8.7170 | 1.7434 | 2743.2 |
| Benzyl Alcohol (Oil Phase) | 5.1801 | 1.0360 | 1630.2 |
| LIPOID 100 S 100 (94% Phosphatidylcholine (PC)) (Oil Phase) | 2.3740 | 0.4748 | 747.1 |
| Glycerin (Oil Phase) | 21.5440 | 4.3088 | 6779.9 |
| Ph Adjuster-1 (DI Systems and water purification) (Oil phase) | 1.0000 | 0.2000 | 314.7 |
| Glycerin (Glycerin phase) | 325.3959 | 65.0792 | 102402.1 |
| BL-05 (*Bif. Longum*) 100B cfu/g | 55.0000 | 11.0000 | 17308.5 |
| Lactoferrin (94% minimum) (Glycerin phase) | 17.5000 | 3.5000 | 5507.3 |
| Ph Adjuster-2 (DI Systems and water purification) | 0.9500 | 0.1900 | 299.0 |
| Stevia (rebaudioside-A) (Flavor) | 1.6715 | 0.3343 | 526.0 |
| Nat. Burgundy Cherry (Mission) (CH-172) | 24.0000 | 4.8000 | 7552.8 |
| Totals | 500 | 100 | 157350.0 |

The oil phase was prepared by weighing the appropriate amounts of Neobee® M-5, Capric and Caprylic Acid, Oleic Acid, Vitamin E 5-67 and Benzyl Alcohol, and then mixing without heat using a magnetic stirrer, until all components dissolve to form the first mixture. LIPOID 100 S 100 (94% Phosphatidycholine (PC)) was added and dissolved at approximately 60° C.-70° C. Once the oil phase (first mixture) was dissolved, Glycerin and pH adjuster-1 were added and mixed until all components were dissolved and the mixture was cooled. Next, Nat. Burgundy Cherry was weighed and added, and mixed until homogenous. The complete oil phase was cooled to room temperature or approximately 30° C.

The glycerin phase was prepared by weighing the appropriate amounts of Glycerin, Ph Adjuster-2 and Stevia and mixing gently until dissolved. *Bif. Longum* was added and mixed gently until dissolved. Lactoferrin was added into a container containing the glycerin phase and all components were mixed with an Arde Barinco high speed shear homogenizer. Components were continually mixed at room temperature until lactoferrin completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler 30° C. for 1 hour and taken from the cooler and remixed thoroughly. Preparation of the emulsion was followed by addition of flavors/sweeteners, if needed, to make up the batch of 157.35 g. After the solution is homogeneous, the solution was poured into hoppers for packaging. The finished solution was tested for the amount of *Bif. Longum* in the solution.

Example 26

Preparation of MAPT Probiotic (Probio-Tec® *Lactobacillus rhamnosus* GG (LGG®)) Formulation Appropriate quantities of the raw materials were weighed for the 157.35 g batch as shown below:

| Ingredient | mg/serving | %/serving | mg/batch |
|---|---|---|---|
| Neobee ® M-5, Capric and Caprylic Acid (Oil Phase) | 26.2625 | 5.2525 | 8264.8 |
| Oleic Acid (Oil Phase) | 10.4050 | 2.0810 | 3274.5 |
| Vitamin E 5-67 (Oil Phase) | 8.7170 | 1.7434 | 2743.2 |
| Benzyl Alcohol (Oil Phase) | 5.1801 | 1.0360 | 1630.2 |
| LIPOID 100 S 100 (94% Phosphatidylcholine (PC)) (Oil Phase) | 2.3740 | 0.4748 | 747.1 |
| Glycerin (Oil Phase) | 21.5440 | 4.3088 | 6779.9 |
| Ph Adjuster-1 (DI Systems and water purification) (Oil phase) | 1.0000 | 0.2000 | 314.7 |
| Glycerin (Glycerin phase) | 330.0459 | 65.0792 | 102402.1 |
| Probio-Tec ® *Lactobacillus rhamnosus* GG LGG ® Conc. 3.5E+11 cfu/g (350B) | 55.0000 | 11.0000 | 17308.5 |
| Lactoferrin (94% minimum) (Glycerin phase) | 17.5000 | 3.5000 | 5507.3 |
| Ph Adjuster-2 (DI Systems and water purification) | 0.9500 | 0.1900 | 299.0 |
| Stevia (rebaudioside-A) (Flavor) | 1.6715 | 0.3343 | 526.0 |
| Nat. Burgundy Cherry (Mission) (CH-172) | 24.000 | 4.8000 | 7552.8 |
| Totals | 500 | 100.0000 | 157350.0 |

The oil phase was prepared by weighing the appropriate amounts of Neobee® M-5, Capric and Caprylic Acid, Oleic Acid, Vitamin E 5-67 and Benzyl Alcohol, and then mixing without heat using a magnetic stirrer, until all components dissolve to form the first mixture. LIPOID 100 S 100 (94% Phosphatidycholine (PC)) was added and dissolved at approximately 75° C.-80° C. Once the oil phase (first mixture) was dissolved, Glycerin and pH adjuster-1 were added and mixed until all components were dissolved and the mixture was cooled. Next, Nat. Burgundy Cherry was weighed and added, and mixed until homogenous. The complete oil phase was cooled to room temperature or approximately 30° C.

The glycerin phase was prepared by weighing the appropriate amounts of Glycerin, Ph Adjuster-2 and Stevia and mixing gently until dissolved. Probio-Tec® *Lactobacillus*

*rhamnosus* GG (LGG®) was added and mixed gently until dissolved. Lactoferrin was added into a container containing the glycerin phase and all components were mixed with an Arde Barinco high speed shear homogenizer. Components were continually mixed at room temperature until lactoferrin completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler 30° C. for 1 hour and taken from the cooler and remixed thoroughly. Preparation of the emulsion was followed by addition of flavors/sweeteners, if needed, to make up the batch of 157.35 g. After the solution is homogeneous, the solution was poured into hoppers for packaging. The finished solution was tested for the amount of Probio-Tec® *Lactobacillus rhamnosus* GG (LGG®) in the solution.

Example 27

Preparation of MAPT Probiotic (*Bifidobacterium Lactis*) Formulation

Appropriate quantities of the raw materials were weighed for the 209.8 g batch as shown below:

| Ingredient | mg/serving | %/serving | mg/batch |
|---|---|---|---|
| Neobee ® M-5, Capric and Caprylic Acid (Oil Phase) | 26.2625 | 5.2525 | 11019.7 |
| Oleic Acid (Oil Phase) | 10.4050 | 2.0810 | 4365.9 |
| Vitamin E 5-67 (Oil Phase) | 8.7170 | 1.7434 | 3657.7 |
| Benzyl Alcohol (Oil Phase) | 5.1801 | 1.0360 | 2173.6 |
| LIPOID 100 S 100 (94% Phosphatidylcholine (PC)) (Oil Phase) | 2.3740 | 0.4748 | 996.1 |
| Glycerin (Oil Phase) | 21.5440 | 4.3088 | 9039.9 |
| Ph Adjuster-1 (DI Systems and water purification) (Oil phase) | 1.0000 | 0.2000 | 419.6 |
| Glycerin (Glycerin phase) | 330.0459 | 66.0092 | 138487.3 |
| BL-04 500B *Bif. Lactis* | 55.0000 | 11.0000 | 23078.0 |
| Lactoferrin (94% minimum) (Glycerin phase) | 17.5000 | 3.5000 | 7343.0 |
| Ph Adjuster-2 (DI Systems and water purification) | 0.9500 | 0.1900 | 398.6 |
| Stevia (rebaudioside-A) (Flavor) | 1.6715 | 0.3343 | 701.4 |
| Nat Maple Syrup (Gold Coast) (600074) | 2.5000 | 0.5000 | 1049.0 |
| Nat. Belgian Waffle (Gold Coast) (382072) | 6.3000 | 1.2600 | 2643.5 |
| Nat. Banana (Gold Coast) (352992) | 4.9500 | 0.9900 | 2077.0 |
| Vanilla (Gold Coast) (603498) | 5.6000 | 1.1200 | 2349.8 |
| Totals | 500.000 | 100.0000 | 209800.0 |

The oil phase was prepared by weighing the appropriate amounts of Neobee® M-5, Capric and Caprylic Acid, Oleic Acid, Vitamin E 5-67 and Benzyl Alcohol, and then mixing without heat using a magnetic stirrer, until all components dissolve to form the first mixture. LIPOID 100 S 100 (94% Phosphatidycholine (PC)) was added and dissolved at approximately 60° C.-70° C. Once the oil phase (first mixture) was dissolved, Glycerin and pH adjuster-1 were added and mixed until all components were dissolved and the mixture was cooled. Next, Nat. Maple Syrup (Gold Coast; 600074), Nat. Belgian Waffle (Gold Coast; 382072), Nat. Banana (Gold Coast; 352992) and vanilla flavor (Gold Coast; 603492) were weighed and added, in order, and mixed until homogenous. The complete oil phase was cooled to room temperature or approximately 30° C.

The glycerin phase was prepared by weighing the appropriate amounts of Glycerin, Ph Adjuster-2 and Stevia and mixing gently until dissolved. *Bifidobacterium Lactis* was added and mixed gently until dissolved. Lactoferrin was added into a container containing the glycerin phase and all components were mixed with an Arde Barinco high speed shear homogenizer. Components were continually mixed at room temperature until lactoferrin completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler 30° C. for 1 hour and taken from the cooler and remixed thoroughly. Preparation of the emulsion was followed by addition of flavors/sweeteners, if needed, to make up the batch of 157.35 g. After the solution is homogeneous, the solution was poured into hoppers for packaging. The finished solution was tested for the amount of *Bifidobacterium Lactis* in the solution.

Example 28

Preparation of MAPT Probiotic (*Lactobacillus Acidophilus*) Formulation

Appropriate quantities of the raw materials were weighed for the 104.9 g batch as shown below:

| Ingredient | mg/serving | %/serving | mg/batch |
|---|---|---|---|
| Neobee ® M-5, Capric and Caprylic Acid (Oil Phase) | 26.2625 | 5.2525 | 5509.9 |
| Oleic Acid (Oil Phase) | 10.4050 | 2.0810 | 2183.0 |
| Vitamin E 5-67 (Oil Phase) | 8.7170 | 1.7434 | 1828.8 |
| Benzyl Alcohol (Oil Phase) | 5.1801 | 1.0360 | 1086.8 |
| LIPOID 100 S 100 (94% Phosphatidylcholine (PC)) (Oil Phase) | 2.3740 | 0.4748 | 498.1 |
| Glycerin (Oil Phase) | 21.5440 | 4.3088 | 4519.9 |
| Ph Adjuster-1 (DI Systems and water purification) (Oil phase) | 1.0000 | 0.2000 | 209.8 |
| Glycerin (Glycerin phase) | 330.0459 | 66.0092 | 69243.6 |
| LA-14 *Lactobacillus Acidophilus* | 55.0000 | 11.0000 | 11539.0 |
| Lactoferrin (94% minimum) (Glycerin phase) | 17.5000 | 3.5000 | 3671.5 |
| Ph Adjuster-2 (DI Systems and water purification) | 0.9500 | 0.1900 | 199.3 |
| Stevia (rebaudioside-A) (Flavor) | 1.6715 | 0.3343 | 350.7 |
| Nat Maple Syrup (Gold Coast) (600074) | 2.5000 | 0.5000 | 524.5 |
| Nat. Belgian Waffle (Gold Coast) (382072) | 6.3000 | 1.2600 | 1321.7 |
| Nat. Banana (Gold Coast) (352992) | 4.9500 | 0.9900 | 1038.5 |
| Vanilla (Gold Coast) (603498) | 5.6000 | 1.1200 | 1174.9 |
| Totals | 500.000 | 100.0000 | 104900.0 |

The oil phase was prepared by weighing the appropriate amounts of Neobee® M-5, Capric and Caprylic Acid, Oleic Acid, Vitamin E 5-67 and Benzyl Alcohol, and then mixing without heat using a magnetic stirrer, until all components dissolve to form the first mixture. LIPOID 100 S 100 (94% Phosphatidycholine (PC)) was added and dissolved at approximately 60° C.-70° C. Once the oil phase (first mixture) was dissolved, Glycerin and pH adjuster-1 were added and mixed until all components were dissolved and the mixture was cooled. Next, Nat. Maple Syrup (Gold Coast; 600074), Nat. Belgian Waffle (Gold Coast; 382072), Nat. Banana (Gold Coast; 352992) and vanilla flavor (Gold Coast; 603492) were weighed and added, in order, and mixed until homogenous. The complete oil phase was cooled to room temperature or approximately 30° C.

The glycerin phase was prepared by weighing the appropriate amounts of Glycerin, Ph Adjuster-2 and Stevia and mixing gently until dissolved. *Lactobacillus Acidophilus* was added and mixed gently until dissolved. Lactoferrin was added into a container containing the glycerin phase and all components were mixed with an Arde Barinco high speed shear homogenizer. Components were continually mixed at room temperature until lactoferrin completely dissolved (no violet colored specks).

The emulsion was prepared by adding the oil phase to the glycerin phase (where each are at approximately 115° F.), slowly while mixing at low to medium RPM using an Arde Barinco Mixer Type 74D (Serial No. L-1274) until the mixture is homogeneous, or approximately 5 minutes. The emulsion was allowed to cool in a cooler 30° C. for 1 hour and taken from the cooler and remixed thoroughly. Preparation of the emulsion was followed by addition of flavors/sweeteners, if needed, to make up the batch of 157.35 g. After the solution is homogeneous, the solution was poured into hoppers for packaging. The finished solution was tested for the amount of *Lactobacillus Acidophilus* in the solution.

Example 29

Preparation of Dry Powder Containing *Lactobacillus acidophilus* and MCT Oil with TPGS Appropriate quantities of the raw materials were weighed for the 88.50 g batch of Solid MCT oil as shown below in Table 8.

TABLE 8

Preparation of Solid MCT oil

| Ingredient | %/serving before evaporation | g/batch |
| --- | --- | --- |
| Vitamin E TPGS | 2.58 | 2.28 |
| MCT Oil | 97.42 | 86.22 |
| Total | 100 | 88.50 |

Appropriate quantities of the raw materials were weighed for the 88.15 g batch as shown below in Table 9.

TABLE 9

Preparation of *Lactobacillus acidophilus*, Lactoferrin and MCT Oil Preparation

| Ingredient | %/serving before evaporation | g/batch | %/serving after evaporation |
| --- | --- | --- | --- |
| Water | 57.500 | 287.5 | 0 |
| KHCO$_3$ | 3.333 | 16.667 | 7.84 |
| Cluster Dextrin | 6.367 | 31.833 | 14.98 |
| SFAE | 4.250 | 21.25 | 10.00 |
| Saladizer ® emulsifier ® | 0.067 | 0.333 | 0.16 |
| Lactoferrin | 6.187 | 30.933 | 14.56 |
| LA-14 200B *Lactobacillus acidophilus* | 4.667 | 23.333 | 10.98 |
| Solid MCT Oil | 17.630 | 88.15 | 41.48 |
| Totals | 100 | 500 | 100 |

The water phase was prepared by weighing the appropriate amounts of water, Saladizer® Emulsifier®, Cluster Dextrin, SFAE and KHCO$_3$ and then mixing at a temperature not more than 50° C.

The solid MCT oil was prepared by weighing the appropriate amounts of TPGS and MCT oil (Table 8) and dissolving the TPGS in the MCT oil at 60° C.

The oil phase was prepared by weighing the appropriate amounts of MCT solid oil, *Lactobacillus acidophilus* and lactoferrin. Then, *Lactobacillus acidophilus* and lactoferrin were mixed into the solid MCT oil solution at 40° C. The oil phase was then cooled to 30° C.

The emulsion was prepared by adding the oil phase to the water phase, slowly while mixing at low to medium RPM using an Arde Barinco Mixer Type 74D (Serial No. L-1274) until the mixture is homogeneous, or approximately 5 minutes. The emulsion was allowed to cool in a cooler to 30° C.

The emulsions were then spray dried into dry powders. The dry powder was prepared using a standard spray dryer equipped with a rotary atomizer nozzle or a standard spray nozzle. Alternatively, a fluid bed dryer or box dryer can be used. The pre-spray emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature no more than 165° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry power in water at a 1:3 or 1:1 powder to water ratio (e.g., 30-50 g powder was dissolved in 100 g of water) and spray drying a second time. The powders were then sifted/filtered using a 60-80 micron mesh screen.

Some pre-spray emulsions required the addition of extra water (i.e., evaporation water) as a processing aid to make the emulsion thinner and able to pass through the dryer pump more easily. The extra water was added to the pre-spray emulsion at 35° C. and was evaporated during the spray dry process, along with the rest of the water in the pre-spray emulsion. The resulting powder was cooled to 35° C. and packaged into appropriate containers.

Example 30

Preparation of Dry Powder Containing *Bifidobacteria lactis*, and MCT Oil with TPGS Appropriate quantities of the raw materials were weighed for the 88.50 g batch of Solid MCT oil as shown below in Table 10.

TABLE 10

Preparation of Solid MCT oil

| Ingredient | %/serving before evaporation | g/batch |
| --- | --- | --- |
| Vitamin E TPGS | 2.58 | 2.28 |
| MCT Oil | 97.42 | 86.22 |
| Total | 100 | 88.50 |

Appropriate quantities of the raw materials were weighed for the 500 g batch as shown below in Table 11.

TABLE 11

Preparation of *Bifidobacteria lactis*, Lactoferrin and MCT Oil Preparation

| Ingredient | %/serving before evaporation | g/batch | %/serving after evaporation |
|---|---|---|---|
| Water | 57.500 | 287.5 | 0 |
| KHCO₃ | 3.333 | 16.667 | 7.84 |
| Cluster Dextrin | 6.367 | 31.833 | 14.98 |
| SFAE | 4.250 | 21.25 | 10.00 |
| Saladizer ® emulsifier | 0.067 | 0.333 | 0.16 |
| Lactoferrin | 6.187 | 30.933 | 14.56 |
| *Bifidobacteria lactis* | 4.667 | 23.333 | 10.98 |
| Solid MCT Oil | 17.630 | 88.15 | 41.48 |
| Totals | 100 | 500 | 100 |

The water phase was prepared by weighing the appropriate amounts of water, Saladizer® emulsifier, Cluster Dextrin, SFAE and KHCO₃ and then mixing at a temperature not more than 50° C.

The solid MCT oil was prepared by weighing the appropriate amounts of TPGS and MCT oil and dissolving the TPGS in the MCT oil at 60° C.

The oil phase was prepared by weighing the appropriate amounts of MCT solid oil, *Bifidobacteria lactis* and lactoferrin. Then, the *Bifidobacteria lactis* and lactoferrin were mixed into the solid MCT oil solution at no more than 40° C. The oil phase was then cooled to 30° C.

The emulsion was prepared by adding the oil phase to the water phase, slowly while mixing at low to medium RPM using an Arde Barinco Mixer Type 74D (Serial No. L-1274) until the mixture is homogeneous, or approximately 5 minutes. The emulsion was allowed to cool in a cooler to 30° C.

The emulsions were then spray dried into dry powders. The dry powder was prepared using a standard spray dryer equipped with a rotary atomizer nozzle or a standard spray nozzle. Alternatively, a fluid bed dryer or box dryer can be used. The pre-spray emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature no more than 175° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry power in water at a 1:3 or 1:1 powder to water ratio (e.g., 30-50 g powder was dissolved in 100 g of water) and spray drying a second time. The powders were then sifted/filtered using a 60-80 micron mesh screen.

Some pre-spray emulsions required the addition of extra water (i.e., evaporation water) as a processing aid to make the emulsion thinner and able to pass through the dryer pump more easily. The extra water was added to the pre-spray emulsion at 35° C. and was evaporated during the spray dry process, along with the rest of the water in the pre-spray emulsion. The resulting powder was cooled to 35° C. and packaged into appropriate containers.

Example 31

Preparation of Dry Powder Containing *Bifidobacteria Infantis* and MCT Oil with TPGS Appropriate quantities of the raw materials were weighed for the 88.50 g batch of Solid MCT oil as shown below in Table 12.

TABLE 12

Preparation of Solid MCT oil

| Ingredient | %/serving before evaporation | g/batch |
|---|---|---|
| Vitamin E TPGS | 2.58 | 2.28 |
| MCT Oil | 97.42 | 86.22 |
| Total | 100 | 88.50 |

Appropriate quantities of the raw materials were weighed for the 500 g batch as shown below in Table 13.

TABLE 13

Preparation of *Bifidobacteria infantis*, Lactoferrin and MCT Oil Preparation

| Ingredient | %/serving before evaporation | g/batch | %/serving after evaporation |
|---|---|---|---|
| Water | 57.500 | 287.5 | 0 |
| KHCO₃ | 3.333 | 16.667 | 7.84 |
| Cluster Dextrin | 6.367 | 31.833 | 14.98 |
| SFAE | 4.250 | 21.25 | 10.00 |
| Saladizer ® emulsifier | 0.067 | 0.333 | 0.16 |
| Lactoferrin | 6.187 | 30.933 | 14.56 |
| *Bifidobacteria Infantis* | 4.667 | 23.333 | 10.98 |
| Solid MCT Oil | 17.630 | 88.15 | 41.48 |
| Totals | 100 | 500 | 100 |

The water phase was prepared by weighing the appropriate amounts of water, Saladizer® emulsifier, Cluster Dextrin, SFAE and KHCO₃ and then mixing at a temperature not more than 50° C.

The solid MCT oil was prepared by weighing the appropriate amounts of TPGS and MCT oil and dissolving the TPGS in the MCT oil at 60° C.

The oil phase was prepared by weighing the appropriate amounts of MCT solid oil, *Bifidobacteria infantis* and lactoferrin. Then, the *Bifidobacteria infantis* and lactoferrin were mixed into the solid MCT oil solution at no more than 40° C.

The emulsion was prepared by adding the oil phase to the water phase, slowly while mixing at low to medium RPM using an Arde Barinco Mixer Type 74D (Serial No. L-1274) until the mixture is homogeneous, or approximately 5 minutes. The emulsion was allowed to cool in a cooler to 30° C.

The emulsions were then spray dried into dry powders. The dry powder was prepared using a standard spray dryer equipped with a rotary atomizer nozzle or a standard spray nozzle. Alternatively, a fluid bed dryer or box dryer can be used. The pre-spray emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature no more than 175° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry power in water at a 1:3 or 1:1 powder to water ratio (e.g., 30-50 g powder was dissolved in 100 g of water) and spray drying a second time. The powders were then sifted/filtered using a 60-80 micron mesh screen.

Some pre-spray emulsions required the addition of extra water (i.e., evaporation water) as a processing aid to make the emulsion thinner and able to pass through the dryer pump more easily. The extra water was added to the pre-spray emulsion at 35° C. and was evaporated during the spray dry process, along with the rest of the water in the pre-spray emulsion. The resulting powder was cooled to 35° C. and packaged into appropriate containers.

Example 32

Preparation of Dry Powder Containing
*Bifidobacterium Longum* Bifilon 50T and MCT Oil
with TPGS Appropriate quantities of the raw materials were weighed for the 53 g batch of Solid MCT oil as shown below in Table 14.

TABLE 14

Preparation of Solid MCT oil

| Ingredient | %/serving before evaporation | g/batch |
|---|---|---|
| Vitamin E TPGS | 2.58 | 1.37 |
| MCT Oil | 97.42 | 51.63 |
| Total | 100 | 53.00 |

Appropriate quantities of the raw materials were weighed for the 300 g batch as shown below in Table 15.

TABLE 15

Preparation of *Bifidobacterium longum* Bifilon 50T, Lactoferrin and MCT Oil Preparation

| Ingredient | %/serving before evaporation | g/batch | %/serving after evaporation |
|---|---|---|---|
| Water | 57.500 | 172.5 | 0 |
| KHCO$_3$ | 3.333 | 10 | 7.84 |
| Cluster Dextrin | 6.367 | 19.1 | 14.98 |
| SFAE | 4.250 | 12.75 | 10.00 |
| Saladizer ® emulsifier | 0.067 | 0.2 | 0.16 |
| Lactoferrin | 6.187 | 18.56 | 14.56 |
| *Bifidobacterium Longum* Bifilon 50T | 4.667 | 14.0 | 10.98 |
| Solid MCT Oil | 17.630 | 52.89 | 41.48 |
| Totals | 100 | 300 | 100 |

The water phase was prepared by weighing the appropriate amounts of water, Saladizer® Emulsifier®, Cluster Dextrin, SFAE and KHCO$_3$ and then mixing at a temperature not more than 55° C.

The solid MCT oil was prepared by weighing the appropriate amounts of TPGS and MCT oil and dissolving the TPGS in the MCT oil at 60° C.

The oil phase was prepared by weighing the appropriate amounts of MCT solid oil, *Bifidobacterium longum* Bifilon 50T and lactoferrin. Then, *Bifidobacterium longum* Bifilon 50T and lactoferrin were mixed into the solid MCT oil solution at no more than 40° C.

The emulsion was prepared by adding the oil phase to the water phase, slowly while mixing at low to medium RPM using an Arde Barinco Mixer Type 74D (Serial No. L-1274) until the mixture is homogeneous, or approximately 5 minutes. The emulsion was allowed to cool in a cooler to 30° C.

The emulsions were then spray dried into dry powders. The dry powder was prepared using a standard spray dryer equipped with a rotary atomizer nozzle or a standard spray nozzle. Alternatively, a fluid bed dryer or box dryer can be used. The pre-spray emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature no more than 175° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry power in water at a 1:3 or 1:1 powder to water ratio (e.g., 30-50 g powder was dissolved in 100 g of water) and spray drying a second time. The powders were then sifted/filtered using a 60-80 micron mesh screen.

Some pre-spray emulsions required the addition of extra water (i.e., evaporation water) as a processing aid to make the emulsion thinner and able to pass through the dryer pump more easily. The extra water was added to the pre-spray emulsion at 35° C. and was evaporated during the spray dry process, along with the rest of the water in the pre-spray emulsion. The resulting powder was cooled to 35° C. and packaged into appropriate containers.

Example 33

Preparation of Dry Powder Containing
*Lactobacillus rhamnosus* GG (Sold Under
Trademark Probio-Tec® LGG®) and MCT Oil with
TPGS Appropriate quantities of the raw materials were weighed for the 106.0 g batch of Solid MCT oil as shown below in Table 16.

TABLE 16

Preparation of Solid MCT oil

| Ingredient | %/serving before evaporation | g/batch |
|---|---|---|
| Vitamin E TPGS | 2.58 | 2.73 |
| MCT Oil | 97.42 | 103.27 |
| Total | 100 | 106.0 |

Appropriate quantities of the raw materials were weighed for the 600 g batch as shown below in Table 17.

TABLE 17

Preparation of *Lactobacillus rhamnosus*, Lactoferrin and MCT Oil Preparation

| Ingredient | %/serving before evaporation | g/batch | %/serving after evaporation |
|---|---|---|---|
| Water | 57.500 | 345.0 | 0 |
| KHCO$_3$ | 3.333 | 20 | 7.84 |
| Cluster Dextrin | 6.367 | 38.2 | 14.98 |
| SFAE | 4.250 | 25.5 | 10.00 |
| Saladizer ® emulsifier ® | 0.067 | 0.4 | 0.16 |
| Lactoferrin | 6.187 | 37.12 | 14.56 |
| *Lactobacillus rhamnosus* GG 3.5E+11 (350B) | 4.667 | 28.0 | 10.98 |
| Solid MCT Oil | 17.630 | 105.78 | 41.48 |
| Totals | 100 | 600 | 100 |

The water phase was prepared by weighing the appropriate amounts of water, Saladizer® Emulsifier®, Cluster Dextrin, SFAE and KHCO$_3$ and then mixing at a temperature not more than 55° C.

The solid MCT oil was prepared by weighing the appropriate amounts of TPGS and MCT oil and dissolving the TPGS in the MCT oil at 60° C.

The oil phase was prepared by weighing the appropriate amounts of MCT solid oil, *Lactobacillus rhamnosus* GG (sold under that tradmarks Probio-Tec® LGG®) and lactoferrin. Then, the *Lactobacillus rhamnosus* GG and lactoferrin were mixed into the solid MCT oil solution. The oil phase then was passed through a filter.

The emulsion was prepared by adding the oil phase to the water phase, slowly while mixing at low to medium RPM using an Arde Barinco Mixer Type 74D (Serial No. L-1274) until the mixture is homogeneous, or approximately 5 minutes. The emulsion was allowed to cool in a cooler to 30° C.

The emulsions were then spray dried into dry powders. The dry powder was prepared using a standard spray dryer equipped with a rotary atomizer nozzle or a standard spray nozzle. Alternatively, a fluid bed dryer or box dryer can be used. The pre-spray emulsion was added to a tank and mixed with a mixer when necessary to keep the liquid homogenous during the spray drying process. The liquid was then pumped to the top of the spray dryer (GEA Niro, Denmark) and sprayed through a nozzle atomizer into the spray dryer, typically kept at a temperature no more than 175° C. When the spray dryer was equipped with a fluid bed, the liquid was sprayed through a rotary atomizer at lower temperatures into the spray dryer. Water then evaporated and pooled at the top of the dryer, while the powder collected at the floor bottom of the dryer, where it was recovered. After recovering the powder, some powders were rewet or instantized by redissolving the dry power in water at a 1:3 or 1:1 powder to water ratio (e.g., 30-50 g powder was dissolved in 100 g of water) and spray drying a second time. The powders were then sifted/filtered using a 60-80 micron mesh screen.

Some pre-spray emulsions required the addition of extra water (i.e., evaporation water) as a processing aid to make the emulsion thinner and able to pass through the dryer pump more easily. The extra water was added to the pre-spray emulsion at 35° C. and was evaporated during the spray dry process, along with the rest of the water in the pre-spray emulsion. The resulting powder was cooled to 35° C. and packaged into appropriate containers.

Since modifications will be apparent to those of skill in this art, it is intended that this invention be limited only by the scope of the appended claims.

What is claimed is:

1. An emulsion composition, comprising:
    a) an agent for delivery, wherein the agent is a probiotic;
    b) a delivery vehicle associated with the agent, wherein the delivery vehicle is selected from among a micelle, inverse micelle, liposome, cubosome and a mixture thereof; and
    c) a mucoadhesive protein associated with the delivery vehicle and/or agent,
   wherein:
    the mucoadhesive protein is present at a concentration of about 1%, by weight, up to about 50% of the total weight of the composition;
    the mucoadhesive protein is selected from among the family of transferrins and the family of mucin proteins, whereby the composition can adsorb to the mucosa for effecting systemic delivery of the agent;
    the mucoadhesive protein is associated with the delivery vehicle and/or the agent via a chemical or physical bond;
    the composition is formulated as an emulsion and is formulated for mucosal delivery to the oral or gastro-intestinal tract mucosa; and
    the emulsion comprises an oil phase, and a polar phase comprising a polar protic solvent other than water, whereby the emulsion does not contain water.

2. The composition of claim 1, wherein the agent is dissolved in the oil phase or is dissolved in the polar protic solvent phase.

3. The composition of claim 1, wherein the polar protic solvent is selected from among polar protic alcohols and glycols.

4. The composition of claim 1, wherein the polar protic solvent is glycerin.

5. The composition of claim 1, wherein the composition comprises a surface active agent selected from among one or more of a polyethylene glycol (PEG)-derivative of vitamin E, polysorbate-80 and phosphatidylcholine.

6. The composition of claim 1, wherein the composition comprises a surface active agent that is a tocopheryl polyethylene glycol succinate (TPGS) or a mixture of the TPGS and a polysorbate.

7. The composition of claim 6, wherein the surface active agent is a high dimer PEG-derivative of vitamin E mixture that comprises TPGS dimer and TPGS monomer and that comprises at least 25 wt% water-soluble dimer.

8. The composition of claim 6, wherein the amount of surface active agent is at least 0.1% to 30%, by weight, of the composition.

9. The composition of claim 1, wherein the mucoadhesive protein is a transferrin.

10. The composition of claim 1, wherein the mucoadhesive protein is lactoferrin.

11. The composition of claim 1, wherein the amount of mucoadhesive protein, by weight of the composition, is 1% to 50% of the total weight of the composition.

12. The composition of claim 1, wherein the amount of mucoadhesive protein, by weight, is 1% to 5% of the total weight of the composition.

13. The composition of claim 1, where the total amount of polar protic solvent is from 5% to 95%, 30% to 95%, 40% to 75%, or 10% to 90%, by weight, of the composition.

14. The composition of claim 1, comprising two polar protic solvents, wherein:
    neither is water;
    the solvents are benzyl alcohol and glycerin;

glycerin is in an amount between 30% and 70% or 60% and 70%, by weight, of the composition; and the benzyl alcohol is in an amount of 1% to 10%, by weight, of the composition.

15. The composition of claim 1, wherein the oil phase comprises a medium chain triglyceride (MCT).

16. The composition of claim 7, wherein the TPGS contains up to 75%, 70%, 69%, 62%, 55%, 50%, 45%, 40%, or 35% dimer or 29%-69%, inclusive, by weight, of dimer; and/or contains less than 70%, 65%, 63%, 62%, or 61%, by weight, of the TPGS monomer.

17. The composition of claim 7, wherein the amount of dimer is greater than 29 wt% and the total amount of dimer and monomer in the TPGS mixture is greater than 95%, 96%, 97%, 98%, or 99%, by weight.

18. The composition of claim 1, comprising glutathione or calcitonin or a probiotic.

19. The composition of claim 1, wherein the agent for delivery is a probiotic selected from *Bifidobacteria* or *Lactobacillus*.

20. A method for mucosal delivery of an agent or use of the composition of claim 1 for mucosal delivery of an agent, comprising contacting the composition with a mucosal surface of a subject, whereby the agent is delivered into the circulatory system of the subject.

21. A method of treating a subject or providing a supplement or use of a composition for treating or supplementing the diet of a subject, comprising administering a composition of claim 1 to the subject.

* * * * *

UNITED STATES PATENT AND TRADEMARK OFFICE
CERTIFICATE OF CORRECTION

PATENT NO. : 10,213,490 B2
APPLICATION NO. : 15/461389
DATED : February 26, 2019
INVENTOR(S) : Bromley et al.

It is certified that error appears in the above-identified patent and that said Letters Patent is hereby corrected as shown below:

In the Specification

At Column 9, Line 14, please replace "HO–CH$_2$CH(OH)CH$_2$.OH" with
—HO–CH$_2$CH(OH)CH$_2$–OH—;

At Column 22, Line 52, please replace "g D-Galactosyl" with —β D-Galactosyl—;

At Column 35, Line 3, please replace "1%-45%" with —1%-15%—.

In the Claims

At Column 90, Lines 1-26, please replace Claim 1 with the following amended claim:
1. An emulsion composition, comprising:
    a) an agent for delivery, wherein the agent is a probiotic;
    b) a delivery vehicle associated with the agent, wherein the delivery vehicle is selected from among a micelle, inverse micelle, liposome, cubosome, and a mixture thereof; and
    c) a mucoadhesive protein associated with the delivery vehicle and/or agent, wherein:
        the mucoadhesive protein is present at a concentration of about 1%, by weight, up to about 50% of the total weight of the composition;
    the mucoadhesive protein is selected from among the family of transferrins and the family of mucin proteins, whereby the composition can adsorb to the mucosa for effecting systemic delivery of the agent;
    the mucoadhesive protein is associated with the delivery vehicle and/or the agent via a chemical or physical bond;
    the composition is formulated as an emulsion and is formulated for mucosal delivery to the oral or gastrointestinal tract mucosa; and
    the emulsion comprises an oil phase, and a polar phase comprising a polar protic solvent other than water, whereby the emulsion does not contain water.

Signed and Sealed this
Twenty-first Day of May, 2019

Andrei Iancu
*Director of the United States Patent and Trademark Office*

At Column 90, Lines 60-62, please replace Claim 13 with the following amended claim:

13. The composition of claim 1, wherein the total amount of polar protic solvent is from 5% to 95%, 30% to 95%, 40% to 75%, or 10% to 90%, by weight, of the composition.